(12) United States Patent
Ensoli

(10) Patent No.: US 9,630,995 B2
(45) Date of Patent: Apr. 25, 2017

(54) METHOD OF IMPROVING IMMUNE FUNCTION IN HIV-INFECTED SUBJECTS ON HAART BY ADMINISTERING HIV-1 TAT

(75) Inventor: Barbara Ensoli, Rome (IT)

(73) Assignee: VAXXIT SRL, Rome (IT)

( * ) Notice: Subject to any disclaimer, the term of this patent is extended or adjusted under 35 U.S.C. 154(b) by 60 days.

(21) Appl. No.: 13/636,118

(22) PCT Filed: Mar. 21, 2011

(86) PCT No.: PCT/EP2011/001606
§ 371 (c)(1),
(2), (4) Date: Nov. 15, 2012

(87) PCT Pub. No.: WO2011/113618
PCT Pub. Date: Sep. 22, 2011

(65) Prior Publication Data
US 2013/0058973 A1 Mar. 7, 2013

(30) Foreign Application Priority Data
Mar. 19, 2010 (GB) .................................. 1004656.3

(51) Int. Cl.
*C07K 14/16* (2006.01)
*A61K 39/21* (2006.01)
*C07K 14/005* (2006.01)
*A61K 39/12* (2006.01)
*A61K 39/00* (2006.01)

(52) U.S. Cl.
CPC ............ *C07K 14/005* (2013.01); *A61K 39/12* (2013.01); *A61K 39/21* (2013.01); *A61K 39/00* (2013.01); *A61K 2039/545* (2013.01); *A61K 2039/57* (2013.01); *C07K 14/163* (2013.01); *C12N 2740/16311* (2013.01); *C12N 2740/16322* (2013.01); *C12N 2740/16334* (2013.01)

(58) Field of Classification Search
CPC .................. C07K 14/163; A61K 39/21; C12N 2740/16311
See application file for complete search history.

(56) References Cited

U.S. PATENT DOCUMENTS

2009/0142319 A1   6/2009   Eck et al.

FOREIGN PATENT DOCUMENTS

| WO | WO-98/17309 | 4/1998 |
| WO | WO-2005/039631 | 5/2005 |
| WO | WO-2005/090391 | 9/2005 |

OTHER PUBLICATIONS

Scadden, D. T., 2003, Stem cells and immune reconstitution in AIDS, Blood Reviews 17:227-231.*
Bekker, V., et al., Aug. 2006, Persistent humoral immune defect in highly activ antiretroviral therapy-treated children with HIV-1 infection: loss of specific antibodies against attenuated vaccine strains and natural viral infection, Pediatrics 118:e315-e322.*
Gallo, R. C., Nov. 2005, The end or the beginning of the drive to an HIV-preventive vaccine: a view from over 20 years, The Lancet 366:1894-1898.*
Letvin, N., Dec. 2006, Progress and obstacles in the development of an AIDS vaccine, Nature Rev. Immunol. 6:930-939.*
Price, P., et al., 2001, Immune dysfunction and immune restoration disease in HIV patients given highly active antiretroviral therapy, J. Clin. Virol. 22:279-287.*
Aiuti, F., andn I. Mezzaroma, 2006, Failure to reconstitute CD4+ T-cells despite suppression of HIV replication under HAART, AIDS Reviews 8:88-97.*
Ensoli, B., et al., Oct. 2008, The therapeutic phase I trial of the recombinant native HIV-1 Tat protein, AIDS 22(18):2207-2217.*
Longo, O., et al., Feb. 2009, Phase I therapeutic trial of the HIV-1 Tat protein and long term follow-up, Vaccine 27:3306-3312.*
Greenough, T. C., et al., 2008, Safety and immunogenicity of recombinant poxvirus HIV-1 vaccines in young adults on highly active antiretroviral therapy, Vaccine 26:6883-6893.*
Longo, O., et al., 2009, Phase I therapeutic trial of the HIV-1 Tat protein and long term follow-up, Vaccine 27:3306-3312.*
Abgrall et al. (2001) "Incidence and Risk Factors for Toxoplasmic Encephalitis in Human Immunodeficiency Virus-infected Patients Before and During the Highly Active Antiretroviral Therapy Era," Clin. Infect. Dis. 33:1747-1755.
Ahlers and Belyakov (2010) "Memories that Last Forever: Strategies for Optimizing Vaccine T-Cell Memory," Blood 115:1678-1689.
Allen et al. (2000) "Tat-Specific Cytotoxic T Lymphocytes Select for SIV Escape Variants during Resolution of Primary Viraemia," Nature 407:386-390.
Andersson et al. (2005) "The Prevalence of Regulatory T Cells in Lymphoid Tissue is Correlated with Viral Load in HIV-Infected Patients," J. Immunol. 174:3143-3147.
Apoil et al. (2005) "FOXP3 mRNA Levels are Decreased in Peripheral Blood CD4+ Lymphocytes from HIV-Positive Patients," J. Acquir. Immune. Defic. Syndr. 39:381-385.
Ariumi et al. (2006) "The Integrase Interactor 1 (INI1) Proteins Facilitate Tat-Mediated Human Immunodeficiency Virus Type 1 Transcription," Retrovirology 3:47.
Arnsten et al., (2007) "Decreased Bone Mineral Density and Increased Fracture Risk in Aging Men with or at Risk for HIV Infection," AIDS 21:617-623.
Baker et al. (2008) "CD4+ Count and Risk of Non-AIDS Diseases Following Initial Treatment for HIV Infection," AIDS 22:841-848.
Barillari et al. (1992) "Effects of Cytokines from Activated Immune Cells on Vascular Cell Growth and HIV-1 Gene Expression. Implications for AIDS-Kaposi's Sarcoma Pathogenesis." J. lmmunol. 149:3727-3734.
Barnett et al. (2001) "The Ability of an Oligomeric Human Immunodeficiency Virus Type a (HIV-1) Envelope Antigen to Elicit Neutralizing Antibodies against Primary HIV-1 Isolates is Improved Following Partial Deletion of the Second Hypervariable Region," J. Virol. 75:5526-5540.
Battegay et al. (2006) "Immunological Recovery and Antiretroviral Therapy in HIV-1 Infection," Lancet Infect. Dis. 6:280-287.

(Continued)

*Primary Examiner* — Jeffrey Parkin
(74) *Attorney, Agent, or Firm* — Morrison & Foerster LLP

(57) ABSTRACT

Native Tat, when administered to patients with HIV infection, or who are otherwise immunocompromised, is capable of restoring immune functions so as to recognize recall antigens, and to inhibit replication and key signs of HIV disease and other persistent infections and/or their progression.

28 Claims, 15 Drawing Sheets

(56) References Cited

OTHER PUBLICATIONS

Bellino et al. (2009) "Parallel Conduction of the Phase I Preventive and Therapeutic Trials Based on the Tat Vaccine Candidate," Reviews on Recent Clinical Trials 4:195-204.
Biancotto et al. (2008) "HIV-1 Induced Activation of CD4+ T cells Creates New Targets for HIV-1 Infection in Human Lymphoid Tissue Ex Vivo," Blood 111:699-704.
Birx et al. (1990) "Induction of Interleukin-6 During Human Immunodeficiency Virus Infection," Blood 76:2303-2310.
Bonnet et al. (2005) "Opportunistic Infections as Causes of Death in HIV-Infected Patients in the HAART Era in France," Scand. J. Infect. Dis. 37:482-487.
Borsetti et al. (2009) "Containment of Infection in Tat Vaccinated Monkeys after Rechallenge with a Higher Dose of SHIV89. 6P(cy243)," Viral Immunol 22:117-124.
Buonaguro et al. (1992) "Effects of the Human Immunodeficiency Virus Type 1 Tat Protein on the Epression of Inflammatoy Cytokines," J. Virol. 66:7159-7167.
Buonaguro et al. (1994) "The Human Immunodeficiency Virus Type 1 Tat Protein Transactivates Tumor Necrosis Factor Beta Gene Expression Through a TAR-Like Structure," J. Virol. 68:2677-2682.
Burgi et al. (2005) "Incidence and Risk Factors for the Occurrence of Non-AIDS-Defining Cancers among Human Immunodeficiency Virus-Infected Individuals," Cancer 104:1505-1511.
Butto et al. (2003) "Sequence Conservation and Antibody Cross-Recognition of Clade B Human Immunodeficiency Virus (HIV) Type 1 Tat Protein in HIV-1 Infected Italians, Ugandans, and South Africans," J. Infect. Dis. 188:1171-1180.
Buzon et al. (2010) "HIV-1 Replication and Immune Dynamics are Affected by Raltegravir Intensification of HAART-Suppressed Subjects," Nat. Med. 16:460-465.
Byrnes et al. (2008) "Immune Activation and IL-12 Production During Acute/Early HIV Infection in the Absence and Presence of Highly Active, Antiretroviral Therapy," J. Leukoc. Biol. 84:1447-1453.
Cafaro et al. (1999) "Control of SHIV-89.6P-Infection of Cynomolgus Monkeys by HIV-1 Tat Protein Vaccine," Nat. Med. 5:643-650.
Cafaro et al. (2000) "SHIV89.6P Pathogenicity in Cynomolgus Monkeys and Control of Viral Replication and Disease Onset by Human Immunodeficiency Virus Type 1 Tat Vaccine," J. Med. Primatol. 29:193-208.
Cafaro et al. (2001) "Vaccination with DNA Containing Tat Coding Sequences and Unmethylated CpG Motifs Protects Cynomolgus Monkeys Upon Infection with Simian/Human Immunodeficiency Virus (SHIV89.6P)," Vaccine 19:2862-2877.
Cafaro et al. (2010) "Impact of Viral Dose and Major Histocompatibility Complex Class IB Haplotype on Viral Outcome in Mauritian Cynomolgus Monkeys Vaccinated with Tat upon Challenge with Simian/Human Immunodeficiency Virus SHIV89.6P," J. Virol. 84:8953-8958.
Caputo et al. (2009) "HIV-1 Tat-Based Vaccines: An Overview and Perspectives in the Field of HIV/AIDS Vaccine Development," Int. Rev. Immunol. 28:285-334.
Chang et al. (1995) "Regulation of Cellular Gene Expression and Function by the Human Immunodeficiency Virus Type 1 Tat Protein," J. Biomed. Sci 2:189-202.
Chang et al. (1997) "HIV-1 Tat Protein Exits from Cells Via a Leaderless Secretory Pathway and Binds to Extracellular Matrix-Associated Heparan Sulfate Proteoglycans Through its Basic Region," AIDS 11:1421-1431.
Chehimi et al. (2007) "Baseline Viral Load and Immune Activation Determine the Extent of Reconstitution of Innate Immune Effectors in HIV-1-Infected Subjects Undergoing Antiretroviral Treatment," J. Immunol. 179:2642-2650.
Chomont et al. (2009) "HIV Reservoir Size and Persistence are Driven by T Cell Survival and Homeostatic Proliferation," Nat. Med. 15:893-900.
Curotto De Lafaille and Lafaille (2009) "Natural and Adaptive Foxp3+ Regulatory T Cells: More of the Same or a Division of Labor?" Immunity 30:626-635.
Deeks (2009) "Immune Dysfunction, Inflammation, and Accelerated Aging in Patients on Antiretriviral Therapy," Top HIV Med. 17:118-123.
Deeks et al. (2009) "HIV Infection, Antiretroviral Treatment, Ageing, and Non-AIDS Related Morbidity," BMJ 338:a3172.
Delaugerre et al. (2010) "Time Course of Total HIV-1 DNA and 2-Long-Terminal Repeat Circles in Patients with Controlled Plasma Viremia Switching to a Raltegravir-ContainingRegimen," ANRS 138 Study Group. AIDS 24:2391-2395.
Desquilbet, et al. (2007) "HIV-1 Infection is Associated with an Earlier Occurrence of a Phenotype Related to Frailty," J. Gerontol. A Biol. Sci Med. Sci 62:1279-1286.
Effros et al. (2008) "Aging and Infectious Diseases: Workshop on HIV Infection and Aging: What is Known and Future Research Directions," Clin. Infect. Dis. 47:542-553.
Eggena et al. (2005) "Depletion of Regulatory T Cells in HIV Infection is Associated with Immune Activation," J. Immunol. 174:4407-4414.
Eigen et al. (1988) "Statistical Geometry in Squence Space: A Method of Quantitative Comparitive Sequence Analysis," Proc. Natl. Acad. Sci. 85:5913-5917.
Emilie et al. (1990) "Production of Interleukins in Human Immunodeficiency Virus-1-Replicating Lymph Nodes," J. Clin. Invest. 86:148-159.
Ensoli et al. (1990) "Tat Protein of HIV-1 Stimulates Growth of Cells Derived from Kaposi's Sarcoma Lesions of AIDS Patients," Nature 344:84-86.
Ensoli et al. (1993) "Release, Uptake, and Effects of Extracellular Human Immunodeficiency Virus Type 1 Tat Protein on Cell Growth and Viral Transactivation," J. Virol. 67:277-287.
Ensoli et al. (1994) "Synergy Between Basic Fibroblast Growth Factor and HIV-1 Tat Protein in Induction of Kaposi's Sarcoma," Nature 371:674-680.
Ensoli et al. (2005) "Vaccines Based on the Native HIV Tat Protein and on the Combination of Tat and the Structural HIV Protein Variant ΔV2 Env," Microbes and Infection 7(4):1392-1399.
Ensoli et al. (2006) "Candidate HIV-1 Tat Vaccine Development: from Basic Science to Clinical Trials," AIDS 20:2245-2261.
Ensoli et al. (2008) "The Therapeutic Phase I Trial of the Recombinant Native HIV Tat Protein," AIDS 22:2207-2209.
Ensoli et al. (2009) "The Preventive Phase I Trial with the HIV-1 Tat-Based Vaccine," Vaccine 28:371-378.
Ensoli et al. (2010) "Therapeutic Immunization with HIV-1 Tat Reduces Immune Activation and Loss of Regulatory T-Cells and Improves Immune Function in Subjects on HAART," PLoS ONE 5:e13540.
Faller et al. (2009) "IL-7 and the HIV Tat Protein Act Synergistically to Down-Regulate CD127 Expression on CD8 T Cells," Int. Immunol. 21:203-216.
Fanales-Belasio et al. (2002) "Native HIV-1 Tat Protein Targets Monocyte-Derived Dendritic Cells and Enhances their Maturation, Function, and Antigen-Specific T Cell Responses," J. Immunol. 168:197-206.
Fanales-Belasio et al. (2009) "HIV-1 Tat Addresses Dendritic Cells to Induce a Predominant Th1-Type Adaptive Immune Response that Appears Prevalent in the Asymptomatic Stage of Infection," J. Immunol. 182:2888-2897.
Finkel et al. (1995) "Apoptosis Occurs Predominantly in Bystander Cells and not in Productively Infected Cells of HIV- and SIV-infected Lymph Nodes," Nat. Med. 1:129-134.
Fry et al. (2001) "Interleukin-7: Master Regulator of Peripheral T-cell Homeostasis?" Trends Immunol. 22:564-571.
Furco et al. (2008) " Restoration of Toxoplasma Gondii-Specific Immune Responses in patients with AIDS Starting HAART," AIDS 22:2087-2096.
Furtado et al. (1999) "Persistence of HIV-1 Transcription in Peripheral-Blood Mononuclear Cells in Patients Receiving Potent Antiretroviral Therapy," N. Engl. J. Med. 340:1614-1622.
Gandhi et al. (2010) "The Effect of Raltegravir Intensification on Low-Level Residual Viremia in HIV-Infected Patients on

(56) References Cited

OTHER PUBLICATIONS

Antiretroviral Therapy: A Randomized Controlled Trial," AIDS Clinical Trials Group A5244 Team. PLoS Med. 7:e1000321.
Gathe et al. (2010) "Phase 3 Trials of Vicriviroc in Treatment-Experienced Subjects Demonstrate Safety but not Significantly Superior Efficacy over Potent Background Regimens Alone," Abstract from 17th Conference on Retroviruses and Opportunistic Infections.
Gavioli et al. (2004) "HIV-1 Tat Protein Modulates the Generation of Cytotoxic T Cell Epitopes by Modifying Proteasome Composition and Enzymatic Activity," J. Immunol. 173:3838-3843.
Gavioli et al. (2008) "The Tat Protein Broadens T Cell Responses Directed to the HIV-1 Antigens Gag and Env: Implications for the Design of New Vaccination Strategies Against Aids," Vaccine 26:727-737.
Gil et al. (2003) "Contribution to Characterisation of Oxidative Stress in HIV/AIDS Patients," Pharmacol. Res. 47:217-224.
Glencross et al. (2008) "CD8/CD38 Activation Yields Important Clinical Information of Effective Antiretroviral Therapy: Findings from the First year of the CIPRA-SA Cohort," Cytometry B Clin. Cytom. 74 Suppl 1:S131-S140.
Goldstein (1996) "HIV-1 Tat Protein as a Potential AIDS Vaccine," Nat. Med. 1:960-964.
Gougeon (2003) "Apoptosis as an HIV Strategy to Escape Immune Attack," Nat. Rev. Immunol. 3:392-404.
Graf et al. (2011) "Elite Suppressors Harbor Low Levels of Integrated HIV DNA and High Levels of 2-LTR Circular HIV DNA Compared to HIV+ Patients On and Off HAART," PLoS Pathog. 7(2):e1001300:1-12.
Grinspoon et al. (2008) "State of the Science Conference: Initiative to Decrease Cardiovascular Risk and Increase Quality of Care for Patients Living with HIV/AIDS: Executive Summary," Circulation 118:198-210.
Hazenberg et al. (2003) "Persistent Immune Activation in HIV-1 Infection is Associated with Progression to AIDS," AIDS 17:1881-1888.
Ho et al. (1993)"Circulating HIV-Specific CD8+ Cytotoxic T Cells Express CD38 and HLA-DR Antigens," Immunol. 150:3070-3079.
Ho et al. (2006) "Two Overrepresented B Cell Populations in HIV-Infected Individuals Undergo Apoptosis by Different Mechanisms," Proc. Natl. Acad. Sci. USA 103:19436-19441.
Hoffmann et al. (2007) "Evolving Characteristics of Toxoplasmosis in Patients Infected with Human Immunodeficiency Virus-1: Clinical Course and Toxoplasma Gondii-Specific Immune Responses," Clin. Microbiol. Infect. 13:510-515.
Houzet et al. (2007) "Fully-Spliced HIV-1 RNAs are Reverse Transcribed with Similar Efficiencies as the Genomic RNA in Virions and Cells, but More Efficiently in AZT-Treated Cells," Retrovirology 4:30.
Hsue et al. (2004) "Clinical Features of Acute Coronary Syndromes in Patients with Human Immunodeficiency Virus Infection," Circulation 109: 316-319.
Hull et al. (2009) "Epidemiology of Treatment Failure: A Focus on Recent Trends," Curr. Opin. HIV AIDS 4:467-473.
Hunt (2007) "Role of Immune Activation in HIV Pathogenesis," Curr. HIV/AIDS Rep 4:42-47.
Hunt et al. (2003) "T Cell Activation is Associated with Lower CD4+ T Cell Gains in Human Immunodeficiency Virus-Infected Patients with Sustained Viral Suppression During Antiretroviral Therapy," J. Infect. Dis. 187:1534-1543.
Hunt et al. (2006) "The Independent Effect of Drug Resistance on T Cell Activation in HIV Infection," AIDS 20:691-699.
Imamichi et al. (2011) "HIV-1 Viruses Detected During Episodic Blips Following IL-7 Administration are Similar to the Viruses Present Before and After IL-7 Therapy," AIDS 25:159-164.
Jiao et al. (2009) "The Decrease of Regulatory T Cells Correlates with Excessive Activation and Apoptosis of CD8+ T Cells in HIV-1-Infected Typical Progressors, but not in Long-Term Non-Progressors," Immunology 128:e366-e375.

Jones and Perelson (2007) "Transient Viremia, Plasma Viral Load, and Reservoir Replenishment in HIV-Infected Patients on Antiretroviral Therapy," J. Acquir. Immune. Defic. Syndr. 45:483-493.
Kelley et al. (2009) "Incomplete Peripheral CD4+ Cell Count Restoration in HIV-Infected Patients Receiving Long-Term Antiretroviral Treatment," Clin. Infect. Dis. 48:787-794.
Kelly et al. (2008) "Human Macrophages Support Persistent Transcription from Unintegrated HIV-1 DNA," Virology 372:300-312.
Kirk et al. (2007) "HIV Infection is Associated with an Increased Risk for Lung Cancer, Independent of Smoking," Clin. Infect. Dis. 45:103-110.
Koesters et al. (2006) "IL-7R α Expression on CD4+ T Lymphocytes Decreases with HIV Disease Progression and Inversely Correlates with Immune Activation," Eur. J. Immunol. 36:336-344.
Kolber (2008) "CD38+CD8+T-Cells Negatively Correlate with CD4 Central Memory Cells in Virally Suppressed HIV-1-Infected Individuals," AIDS 22:1937-1941.
Lambotte et al. (2000) "Detection of Infectious HIV in Circulating Monocytes from Patients on Prolonged Highly Active Antiretroviral Therapy," J. Acqui. Immune Defic. Syndr. 23:114-119.
Lassen et al. (2004) "Analysis of Human Immunodeficiency Virus Type 1 Transcriptional Elongation in Resting CD4+ T Cells in Vivo," J. Virol. 78:9105-9114.
Lassen et al. (2006) "Nuclear Retention of Multiply Spliced HIV-1 RNA in Resting CD4+ T Cells," PLoS. Pathog. 2(7)e68:0650-0661.
Lee et al. (1999) "Epitope Mapping of CCR5 Reveals Multiple Conformational States and Distinct but Overlapping Structures Involved in Chemokine and Coreceptor Function," J. Biol. Chem. 274:9617-9626.
Liang et al. (2004) "Spliced Human Immunodeficiency Virus Type 1 RNA is Reverse Transcribed into cDNA Within Infected Cells," AIDS Res. Hum. Retroviruses 20:203-211.
Longo et al. (2009) Phase I Therapeutic Trial of the HIV-1 Tat Protein and Long Term Follow-up, Vaccine 27:3306-3312.
Luft and Remington (1992) "Toxoplasmic Encephalitis in AIDS," Clin. Infect. Dis. 15:211-222.
Maggiorella et al. (2004) "Long-Term Protection Against SHIV89.6P Replication in HIV-1 Tat Vaccinated Cynomolgus Monkeys," Vaccine 22:3258-3269.
Margolis (2011) "Eradication Therapies for HIV Infection: Time to Begin Again," AIDS Res. Hum. Retriviruses [Epub ahead of print].
Martinez-Picado (2010) "Hiv-1 Replication and Immune Dynamics are Impacted by Raltegravir Intensification of HAART-Suppressed Patients," CROI Abstract 100LB.
Matsuyama et al. (1991) "Cytokines and HIV Infection: Is AIDS a Tumor Necrosis Factor Disease'?" AIDS 5:1405-1417.
Mazzucchelli et al. (2008) "Development of Regulatory T Cells Requires IL-7R alpha Stimulation by IL-7 or TSLP," Blood 112:3283-3292.
Miller et al. (2008) "Human Effector and Memory CD8+ T Cell Responses to Smallpox and Yellow Fever Vaccines," Immunity 28:710-722.
Monforte et al. (2008) "HIV-Induced Immunodeficiency and Mortality from AIDS-Defining and Non-AIDS-Defining Malignancies," AIDS 22:2143-2153.
Mozos et al. (2007) "Redistribution of FOXP3-Positive Regulatory T Cells from Lymphoid Tissues to Peripheral Blood in HIV-Infected Patients," J. Acquir. Immune. Defic. Syndr. 46:529-537.
Mullis and Faloona. (1987) "Specific Synthesis of DNA In Vitro via a Polymerase-Catalyzed Chain Reaction," Methods Enzymol. 155:335-350.
Natarajan et al. (1999) "HIV-1 Replication in Patients with Undetectable Plasma Virus Receiving HAART. Highly Active Antiretroviral Therapy," Lancet 353:119-120.
Nettles and Kieffer (2006) "Update on HIV-1 Viral Load Blips," Curr. Opin. HIV. AIDS 1:157-161.
O'Connor et al. (2002) "Acute Phase Cytotoxic T Lymphocyte Escape is a Hallmark of Simian Immunodeficiency Virus Infection," Nat. Med. 8:493-499.
Odden et al. (2007) "Cystatin C Level as a Marker of Kidney Function in Human Immunodeficiency Virus Infection: the FRAM Study," Arch. Intern. Med. 167:2213-2219.

(56) References Cited

OTHER PUBLICATIONS

Oswald-Richter et al. (2004) "HIV Infection of Naturally Occurring and Genetically Reprogrammed Human Regulatory T-Cells," PLoS Biol. 2:0955-0966.
Oyaizu et al. (1993) "Accelerated Apoptosis in Peripheral Blood Mononuclear Cells (PBMCs) from Human Immunodeficiency Virus Type-1 Infected Patients and in CD4 Cross-Linked PBMCs from Normal Individuals," Blood 82:3392-3400.
Palmer et al. (2008) "Low-Level Viremia Persists for at Least 7 Years in Patients on Suppressive Antiretroviral Therapy," Proc. Natl. Acad. Scie. U.S.A. 105:3879-3884.
Pollard (1994) "The In Vivo Isotopic Labeling of Proteins for Polyacrylamide Gel Electrophoresis," Methods Mol. Biol. 32:67-72.
Potter et al. (2007) "Preserved Central Memory and Activated Effector Memory CD4+ T-Cell Subsets in Human Immunodeficiency Virus Controllers: an ANRS EP36 Study," J. Virol. 81:13904-13915.
Rayne et al. (2010) "Phosphatidylinositol-(4,5)-biphosphate Enables Efficient Secretion of HIV-1 Tat by Infected T-Cells," EMBO J 29:1348-1362.
Re et al. (1995) "Effect of Antibody to HIV-1 Tat Protein on Viral Replication In Vitro and Progression of HIV-1 Disease In Vivo," J. Acquir. Immune. Defic. Syndr. Hum. Retrovirol. 10:408-416.
Re et al. (2001) "Antibodies Against Full-Length Tat Protein and some Low-Molecular-Weight Tat-Peptides Correlate with Low or Undetectable Viral Load in HIV-1 Seropositive Patients," J. Clin. Virol. 21:81-89.
Reigadas et al. (2010) "Evolution of 2-Long Terminal Repeat (2-LTR) Episomal HIV-1 DNA in Raltegravir-Treated Patients and in In Vitro Infected Cells," J. Antimicrob. Chemother. 65:434-437.
Reiss et al. (1990) "Speed of Progression to AIDS and Degree of Antibody Response to Accessory Gene Products of HIV-1," J. Med. Virol. 30:163-168.
Reiss et al. (1991) "Contribution of Antibody Response to Recombinant HIV-1 Gene-Encoded Products NEF, REV, TAT, and Protease in Predicting Development of AIDS in HIV-1-Infected Individuals," J. Acquir. Immune. Defic. Syndr. 4:165-172.
Remoli et al. (2006) "Intracellular HIV-1 Tat Protein Represses Constitutive LMP2 Transcription Increasing Proteasome Activity by Interfering with the Binding of IRF-1 to STAT1," Biochem. J. 396:371-380.
Rethi et al. (2005) "Loss of IL-7R alpha is Associated with CD4 T-Cell Depletion, High Interleukin-7 Levels and CD28 Down-Regulation in HIV Infected Patients," AIDS 19:2077-2086.
Rezza et al. (2005) "The Presence of Anti-Tat Antibodies is Predictive of Long-Term Nonprogression to AIDS or Severe Immunodeficiency: Findings in a Cohort of HIV-1 Seroconverters," J. Infect. Dis. 191:1321-1324.
Richman et al. (2009) "The Challenge of Finding a Cure for HIV Infection," Science 323:1304-1307.
Rodman et al. (1993) "Epitopes for Natural Antibodies of Human Immunodeficiency Virus (HIV)-Negative (Normal) and HIV-Positive Sera are Coincident with Two Key Functional Sequences of HIV Tat Protein," Proc. Natl. Acad. Sci. USA 90:7719-7723.
Rouse et al. (2006) "Regulatory T Cells in Virus Infections," Immunol. Rev. 212:272-286.
Saez-Cirion et al. (2007) "HIV Controllers Exhibit Potent CD8 T Cell Capacity to Suppress HIV Infection Ex Vivo and Peculiar Cytotoxic T Lymphocyte Activation Phenotype," Proc. Natl. Acad. Sci. USA 104:6676-6781.
Savarino et al. (1999) "Effects of the Human CD38 Glycoprotein on the Early Stages of the HIV-1 Replication Cycle," FASEB J. 13:2265-2276.
Schroecksnadel et al. (2008) "Quality of Life and Immune Activation in Patients with HIV-Infection," Brain Behav. Immun. 22:881-889.
Smith et al. (2004) "Is Antiretroviral Treatment of Primary HIV Infection Clinically Justified on the Basis of Current Evidence?," AIDS 18:709-718.
Srivastava et al. (2003) "Purification, Characterization, and Immunogenicity of a Soluble Trimeric Envelope Protein Containing a Partial Deletion of the V2 Loop Derived from SF162, an R5-Tropic Human Immunodeficiency Virus Type 1 Isolate," J. Virol 77:11244-11259.
Szabo et al. (2004) "Evaluation of an Automated Instrument for Viability and Concentration Measurements of Cryopreserved Hematopoietic Cells," Lab Hematol. 10:109-111.
Timothy et al. (2010) "Maraviroc Intensification for Suboptimal CD4+ Cell Response Despite Sustained Virologic Suppression: ACTG 5256," Abstract from 17th Conference on Retroviruses and Opportunistic Infections.
Toschi et al. (2001) "Activation of Matrix-Metalloproteinase-2 and Membrane-type-1-Matrix-Metalloproteinase in Endothelial Cells and Induction of Vascular Permeability In Vivo by Human Immunodeficiency Virus-1 Tat Protein and Basic Fibroblast Growth Factor," Mol. Biol. Cell 12:2934-2946.
Valdez et al. (2002) "Limited Immune Restoration After 3 Years' Suppression of HIV-1 Replication in Patients with Moderately Advanced Disease," AIDS 16:1859-1866.
Van Baalen et al. (1997) "Human Immunodeficiency Virus Type a Rev- and Tat-Specific Cytotoxic T Lymphocyte Frequencies Inversely Correlate with Rapid Progression to AIDS," J. Gen. Virol. 78:1913-1918.
Venet et al. (1992) "Cytotoxic T Lymphocyte Response Against Multiple Simian Immunodeficiency Virus[4] (SIV) Proteins in SIV-Infected Macaques," J. Immunol. 148:2899-2908.
Wang et al. (2005) "IL-7 is a Potent and Proviral Strain-Specific Inducer of Latent HIV-1 Cellular Reservoirs of Infected Individuals on Virally Suppressive HAART," J. Clin. Invest. 115:128-137.
Weber et al. (2006) "Liver-Related Deaths in Persons Infected with the Human Immunodeficiency Virus: the D:A:D Study," Arch. Intern. Med. 166:1632-1641.
Weiss et al. (1989) "HIV Infection is Associated with the Spontaneous Production of Interleukin-1 (IL-1) In Vivo and with an Abnormal Release of IL-1 Alpha In Vitro," AIDS 3:695-699.
Welles et al. (1996) "Prognostic Value of Plasma Human Immunodeficiency Virus Type 1 (HIV-1) RNA Levels in Patients with Advanced HIV-1 Disease and with Little or No Prior Zidovudine Therapy. AIDS Clinical Trials Group Protocol 116A/116B/117 Team," J. Infect. Dis. 174:696-703.
Wilkin et al. (2010) "Maraviroc Intensification for Suboptimal CD4+ Cell Response Despite Sustained Virologic Suppression: ACTG 5256," Abstract 285 CROI, San Francisco Feb. 16-19, 2010.
Wu and Marsh (2001) "Selective Transcription and Modulation of Resting T Cell Activity by Preintegrated HIV DNA" Science 293:1503-1506.
Wu and Marsh (2003) "Early Transcription from Nonintegrated DNA in Human Immunodeficiency Virus Infection," J. Virol. 77:10376-10382.
Zagury et al. (1998) "Antibodies to the HIV-1 Tat Protein Correlated with Nonprogression to AIDS: A Rationale for the Use of Tat Toxoid as an HIV-1 Vaccine," J. Hum. Virol. 1:282-292.
Zhang et al. (1999) "Quantifying Residual HIV-1 Replication in Patients Receiving Combination Antiretroviral Therapy," N. Engl. J. Med. 340:1605-1613.
Zhu et al. (2002) "Evidence for Human Immunodeficiency Virus Type 1 Replication In Vivo in CD14(+) Monocytes and its Potential Role as a Source of Virus in Patients on Highly Active Antiretroviral Therapy," J. Virol. 76:707-716.
Chun et al., "Gene expression and viral production in latently infected, resting $CD4^+$ T cells in viremic versus aviremic HIV-infected individuals," PNAS (2003) 100(4):1908-1913.
Graziosi et al., "Kinetics of human immunodeficiency virus type 1 (HIV-1) DNA and RNA synthesis during primary HIV-1 infection," PNAS (1993) 90:6405-6409.
HIV-1 TAT Vaccines, Clinical Trial ISST-001, retrieved from the Internet Feb. 10, 2015, 3 pages.
Ho et al., "Measuring reversal of HIV-1 latency ex vivo using cells from infected individuals," PNAS (2014) (19):6860-6861.

(56) References Cited

OTHER PUBLICATIONS

Monini et al., "HIV-1 Tat Promotes Integrin-Mediated HIV Transmission to Dendritic Cells by Binding Env Spikes and Competes Neutralization by Anti-HIV Antibodies," PLoS ONE (2012) 7(11):e48781, 23 pages.
Ramratnam et al., "The decay of the latent reservoir of replication-competent HIV-1 is inversely correlated with the extent of residual viral replication during prolonged anti-retroviral therapy," Nature Medicine (2000) 6(1):82-85.
Appay et al., "Immune activation and inflammation in HIV-I infection: causes and consequences," J Pathol (2008) 214:231-241.
Autran et al., "Greater viral rebound and reduced time to resume antiretroviral therapy after therapeutic immunization with the ALVAC-HIV vaccine (vCP1452)," AIDS (2008) 22(11):1313-1322.
Autran et al., "Positive effects of combined antiretroviral therapy on CD4+ T cell homeostasis and function in advanced HIV disease," Science (1997) 277:112-116.
Brenchley et al., "HIV disease: fallout from a mucosal catastrophe," Nature Immunology (2006) 7(3):235-239.
Chantratita et al., "Delayed progression to AIDS in volunteers treated with long-term HIV-1 immunogen (REMUNE) therapy in Thailand," HIV Medicine (2004) 5:317-325.
Chomont et al., "HIV reservoir size and persistence are driven by T cell survival and homeostatic proliferation," Nature Medicine (2009) 15(8):893-901.
Chun et al., "Persistence of HIV in Gut-associated lymphoid tissue despite long-term antiretroviral therapy," JID (2008) 197:714-720.
Deeks, "Shock and Kill," Nature (2012) 487:439-440.
Dinoso et al., "Treatment intensification does not reduce residual HIV-1 viremia in patients on highly active antiretroviral therapy," PNAS (2009) 106(23):9403-9408.
Egan, "Current prospects for the development of a therapeutic vaccine for the treatment of HIV type 1 infection," AIDS Research and Human Retroviruses (2004) 20(8):794-806.
Emery et al., "Randomized, placebo-controlled, phase I/IIa evaluation of the safety and immunogenicity of fowlpox virus expressing HIV gag-pol and interferon-? in HIV-1 infected subjects," Human Vaccines (2005) 1(6):232-238.
Emery et al., "Influence of IFN co-expression on the safety and antiviral efficacy of recombinant fowlpox virus HIV therapeutic vaccines following interruption of antiretroviral therapy," Human Vaccines (2007) 3(6):260-267.
Fernandez-Cruz et al., "The potential role of the HIV-1 immunogen (Remune) as a therapeutic vaccine in the treatment of HIV infection," Expert Rev Vaccines (2003) 2(6):739-752.
Fletcher et al., "Persistent HIV-1 replication is associated with lower antiretroviral drug concentrations in lymphatic tissues," PNAS (2014) 111(6):2307-2312.
Gray et al., "Overview of STEP and Phambili trial results: two phase IIb test of concept studies investigating the efficacy of MRK ad5 gag/pol/nef sub-type B HIV vaccine," Curr Opin HIV AIDS (2010) 5(5):357-361.
Jacobson et al., "Evidence that intermittent structured treatment interruption, but not immunization with ALVAC-HIV vCP1452, promotes host control of HIV replication: the results of AIDS clinical trials group 5068," JID (2006) 194:623-632.
Jiang et al., "Plasma levels of bacterial DNA correlate with immune activation and the magnitude of immune restoration in persons with antiretroviral-treated HIV infection," JID (2009) 199:1177-1185.
Jiao et al., "The decrease of regulatory T cells correlates with excessive activation and apoptosis of CD8+ T cells in HIV-1-infected typical progressors, but not in long-term non-progressors," Immunology (2009) 128(1 pt 2):e366-375.
Joos et al., "HIV rebounds from latently infected cells, rather than from continuing low-level replication," PNAS (2008) 105(43):16725-16730.
Kiepiela et al., "CD8+ T-cell responses to different HIV proteins have discordant association with viral load," Nature Medicine (2007) 13(1):46-53.
Kilby et al., "A randomized, partially blinded phase 2 trial of antiretroviral therapy, HIV-Specific immunizations, and interleukin-2 cycles to promote efficient control of viral replication (ACTG A5024)," JID (2006) 194:1672-1676.
Kinloch-De Loes et al., "Impact of therapeutic immunization on HIV-1 viremia after discontinuation of antiretroviral therapy initiated during acute infection," JID (2005) 192:607-617.
Koup et al., "The quest for a T cell-based immune correlate of protection against HIV: a story of trials and errors," Immunology (2011) 11:65-70.
Lederman et al., "Residual Immune Dysregulation Syndrome in Treated HIV infection," Adv. Immunol. (2013) 119:51-83.
Levy et al., "Immunological and virological efficacy of a therapeutic immunization combined with interleukin-2 in chronically HIV-1 infected patients," AIDS (2005) 19:279-286.
Lorenzo-Redondo et al., "Persistent HIV-1 replication maintains the tissue reservoir during therapy," Nature (2016) 530:51-56.
Margolis, "Mechanisms of HIV Latency: an Emerging Picture of Complexity," Curr HIV/AIDS Rep (2010) 7:37-43.
McMichael et al., "The immune response during acute HIV-1 infection: clues for vaccine development," Nat Rev Immunol. (2010) 10(1):11-23.
Mohri et al., "Increased Turnover of T Lymphocytes in HIV-1 Infection and Its Reduction by Antiretroviral Therapy," J. Exp. Med. (2001) 194(9):1277-1287.
Moir and Fauci, "B cells in HIV infection and disease," Nat Rev Immunol. (2009) 9(4):235-245.
Munier and Kelleher, "Acutely dysregulated, chronically disabled by the enemy within: T-cell responses to HIV-1 infection," Immunology and Cell Biology (2007) 85:6-15.
Oxenius et al., "Sitmulation of HIV-specific cellular immunity by structured treatment interruption fails to enhance viral control in chronic HIV Infection," PNAS (2002) 99(21):13747-13752.
Sedaghat et al., "Limits on Replenishment of the Resting CD4+T Cell Reservoir for HIV in Patients on HAART," PLoS Pathogens (2007) 3(8):e122, 1165-1174.
Siliciano et al., "Long-term follow-up studies confirm the stability of the latent reservoir for HIV-1 in resting CD4+ T cells," Nature Medicine (2003) 9(6):727-728.
Streeck et al., "Immunological and Virological Impact of Highly Active Antiretroviral Therapy Initiated during Acute HIV-1 Infection," The Journal of Infectious Diseases (2006) 194:734-739.
Virgin and Walker, "Immunology and the elusive AIDS vaccine," Nature (2010) 464:224-231.
Yukl and Wong, "Blood and Guts and HIV: Preferential HIV Persistence in GI Mucosa," The Journal of Infectious Diseases (2008) 197:640-642.
Buzon et al., "HIV-1 replication and immune dynamics are affected by raltegravir intensification of HAART-suppressed subjects," Nat Med (2010) 16(4):460-465.
Ensoli et al., "The preventive phase I trial with the HIV-1 Tat-based vaccine," Vaccine (2009) 28(2):371-378.
Ensoli et al., "Therapeutic immunization with HIV-1 Tat reduces immune activation and loss of regulatory T-cells and improves immune function in subjects on HAART," PLoS One (2010) 5(11):e13540, 29 pages.
Ensoli et al., "Vaccines based on the native HIV Tat protein and on the combination of Tat and the structural HIV protein variant DeltaV2 Env," Microbes Infect (2005) 7(14):1392-1399.
Gavioli et al., "The Tat protein broadens T cell responses directed to the HIV-1 antigens Gag and Env: implications for the design of new vaccination strategies against AIDS," Vaccine (2008) 26(5):727-737.
International Preliminary Report on Patentability and Written Opinion for PCT/EP2011/001606, dated Sep. 25, 2012, 8 pages.
International Search Report for PCT/EP2011/001606, mailed Aug. 19, 2011, 5 pages.
Maggiorella et al., "Long-term protection against SHIV89.6P replication in HIV-1 Tat vaccinated cynomolgus monkeys," Vaccine (2004) 22(25-26):3258-3269.

(56) References Cited

OTHER PUBLICATIONS

Rezza et al., "The presence of anti-Tat antibodies is predictive of long-term nonprogression to AIDS or severe immunodeficiency: findings in a cohort of HIV-1 seroconverters," J Infect Dis (2005) 191(8):1321-1324.

* cited by examiner

METHOD OF IMPROVING IMMUNE FUNCTION IN HIV-INFECTED SUBJECTS ON HAART BY ADMINISTERING HIV-1 TAT

CROSS-REFERENCE TO RELATED APPLICATIONS

This application is a U.S. National Phase Application of International Patent Application No. PCT/EP2011/001606 having an international filing date of Mar. 21, 2011, which claims priority to United Kingdom Patent Application No. 1004656.3 filed Mar. 19, 2010, the disclosures of which are herein incorporated by reference in their entirety.

FIELD OF THE INVENTION

The present invention relates to the treatment of individuals with disorders of the immune system, and substances for use in such treatment.

INTRODUCTION

Human immunodeficiency virus/acquired immunodeficiency syndrome (HIV/AIDS) represents a challenging health problem with a worldwide impact, particularly in developing countries. The use of antiretroviral drugs in the last 20 years has changed the expectancy and quality of life of HIV infected individuals. However, in spite of virus-suppressing drug intervention, key signs of AIDS progression, including persistent immune activation, CD4 T cell and B cell decay, and loss of immune functions, are only partially reverted by highly active anti-retroviral therapy (HAART) and are also associated with increased risk of non-AIDS defining illnesses and causes of death (i.e. tumours, cardiovascular diseases, liver failure, kidney failure, central nervous system disorders, including encephalitis such as *toxoplasma* encephalitis, persistent infections, etc.), and early ageing, representing constant problems in HIV clinical management (1-23). The term immune activation is used herein to refer to chronic stimulation of the immune system.

Without being bound by theory, the high turnover of immune cells can lead to a decrease and even complete disappearance of previously established immune responses. Antigens against which immunity has been generated are termed 'recall' antigens. Once lost, there is no known means to re-establish immunity against recall antigens.

HAART involves treatment with multiple antiretroviral agents, with the aim of both blocking virus replication and of avoiding the development of drug resistance. However, although this therapy suppresses HIV replication to the point where no virus can be detected in blood, it only partially reverts the immune activation and dysfunction that characterise AIDS progression. In fact, residual virus replication is detected in most patients receiving HAART. This originates from viral reservoirs, which include latently infected CD4+ T cells, monocyte-macrophages, dendritic cells, natural killer (NK) cells, hematopoietic stem cells, mast cells, several cell types in the central nervous system, and other cells, which cells harbour integrated proviral DNA and maintain unintegrated DNA expressing regulatory genes (24-34). This demonstrates that viral proteins are still produced even when the individual is undergoing "successful" therapy (35).

In addition, there is evidence that cells harbour archival HIV proviruses, which have not undergone the selective pressure by the anti-viral immune response and/or by HAART treatment. These proviruses do not usually give rise to viral particles, although they can express viral transcripts (24-35). In this regard, peripheral blood CD4+ lymphocytes harbouring latent proviruses (36), termed transitional memory cells, proliferate in response to interleukin-7 (IL-7) without apparent induction of viral replication. As a result, these latently infected cells can persist indefinitely, constituting a virus reservoir which is insensitive to the attack of the anti-viral immune response and/or HAART treatment, save in the case of viral replication, for example, which can occur upon T cell activation.

Other, long-living, non-dividing cell reservoirs harbouring latent proviruses have also been reported (24-34). Taken together, these reservoirs appear to be the cause of the persistent immune activation and dysfunction observed in HAART, and pose an apparently insurmountable obstacle to HIV elimination (35).

Thus, complete elimination of HIV in infected individuals remains a relevant problem of HIV treatment. Drugs have been developed to increase virus control and to reduce chronic immune activation. In particular, HAART intensification by Raltegravir, an inhibitor of virus integration, is accompanied by reduction of integrated HIV proviral DNA and by the increase in 2-LTR circle episomal DNA (unintegrated proviral DNA) in the absence of relevant changes in total HIV proviral DNA, as well as by a reduction of immune activation (37, 38). This suggests again that active viral replication occurs, even under effective HAART, and is a cause of aberrant immune activation, a key sign of the disease. On the other hand, those HIV-1 infected individuals known as Elite Suppressor (39), who control HIV infection in the absence of drugs and do not progress, have a lower content of integrated provirus (viral reservoir), a higher content of 2-LTR unintegrated DNA and lower immune activation as compared to HAART-treated individuals.

Thus, viral gene products and/or virus-induced host factors such as pro-inflammatory cytokines are still produced even under "successful" antiretroviral therapy, and may exert a positive pressure on virus gene expression, as suggested by the frequent occurrence of "blips" of virus replication and persistent residual viraemia, as well as by the appearance of mutated and drug-resistant viruses during HAART (virological failure). In this regard, an increased production of multispliced transcripts encoding HIV regulatory proteins such as Tat, that is known to activate viral and cellular gene expression, has been detected in vitro under antiretroviral treatment, suggesting that these factors may continue to stimulate HIV gene expression as well as the expression of cytokines and other cellular genes, even in the absence of detectable virus replication in blood (53, 54). This, in turn, can result in further increase of HIV gene expression and continued immune stimulation, which can establish a vicious cycle that ultimately leads to persistent immune activation, loss of regulatory T cells (T-regs), immune dysfunction, inflammation and clinical manifestations.

In particular, expression of Tat during effective HAART is supported by results of anti-Tat antibody seroconversion in treated patients (57). Of note, HIV-1 Tat binds the integrase interactor-1 (INI-1), a chromatin remodelling factor which enhances Tat transcriptional activity (58). Since INI-1 is known to bind HIV integrase and to stimulate its activity, Tat binding to the INI-1/HIV integrase complex may facilitate HIV DNA integration into the host genome, as well as HIV gene expression, maintenance of the viral reservoir and, ultimately, immune activation.

Accordingly, therapeutic interventions that do not specifically target the virus, such as CCR5 antagonists, are being explored in association with conventional virus-targeting drugs in clinical trials, with the aim of reducing chronic immune dysregulation and restoring CD4$^+$ T cells and immune functions.

It was expected that treatment with the CCR5 receptor antagonists, Maraviroc or Vicrimiroc, would have helped boost levels of CD4$^+$ T cells and increase immune functions, and reduce latent infection. However, the literature shows that these CCR5 receptor antagonists only partially reduce immune activation in a generic and non-specific-fashion, and neither of the desired effects was observed. Levels of CD4$^+$ T cells decrease slightly, and an increase in latent infection is observed. In addition, Maraviroc reduces central memory T cells and increases effector memory T cells (61), an effect that does not counteract that of HIV infection (62, 63), thereby indicating a lack of restoration of immune functions.

In addition to this approach, cytokines are also being used with HAART as therapeutic strategies to improve immune functions, as well as to induce the activation of latent proviruses, thus rendering the virus sensitive to HAART, with the goal of reducing the virus reservoir, to attack the archival provirus, and to achieve virus elimination. As mentioned above, proviral DNA (i.e., integrated and non-replicating) is preferentially detected in a subset of memory T cells, termed transitional memory T cells, which proliferate in response to IL-7, which is increased in infected people, ensuring persistence of a cell reservoir resistant to HAART, as no virus is produced during the IL-7-driven homeostatic proliferation, posing an apparently insurmountable obstacle to virus elimination (36). In this context, IL-7 was found to be effective at inducing proviral reactivation in vitro from resting CD4+ T lymphocytes from HIV-1-infected patients on suppressive HAART (64). However, only low level viremia was induced by the administration of IL-7 to patients, likely reflecting a transient induction or release of the current virus without attacking the archival provirus, since the plasma virus detected was indistinguishable from the viral quasispecies present prior to or after IL-7 treatment. Of importance, the episodic blips did not have any substantial impact on the pattern of PBMC proviral DNA, and the provirus population present prior to treatment persisted (65). Thus, treatment with recombinant human IL-7 failed at inducing production from previously silent reservoirs and cannot be considered an effective tool to eliminate the virus.

On the other hand, IL-7 is considered a key cytokine in T cell homeostasis, acting both during thymopoiesis and in the periphery, promoting naive T cell proliferation and survival as well as the maintenance of memory cells (66). In addition, it has been shown that IL-7R signaling is absolutely required for normal development of regulatory T cells (67). Thus, much expectation has been placed on the therapeutic use of IL-7 to improve thymic output and broaden the T cell repertoire in lymphopenic clinical settings, including HIV infection. It is noteworthy that HIV-1 infection is associated with high levels of circulating IL-7, levels increasing in lymphopenic states because of a compensatory feedback loop (68), but with a decreased expression of the IL-7 receptor α-chain (IL-7Rα) on T cells. This directly correlates with CD4 depletion and immune activation (69), and with the appearance of numerous B cell defects in individuals with advancing HIV disease, including immature-transitional B cells (70). In this context, it has been shown that Tat is capable of binding to the IL-7 receptor α-chain (IL-7Rα) and of inducing its internalization and degradation, resulting in a down-regulation of IL-7Rα expression on T cells (71). Thus, Tat modulation of the IL-7/IL-7R pathway functions might be associated with the Treg, T and B cell defects and immune dysfunction observed in HIV infection.

T-regs are decreased in HIV infected patients even under HAART (72, 73). In this regard, US Patent Application No. 20090142319 discloses a method for producing ex vivo CD4$^+$CD25$^+$ nTreg cells comprising enriching CD4$^+$CD25$^+$ regulatory T cells in a sample and expanding the population of the enriched CD4+CD25+ regulatory T cells while treating the enriched cells with a PI-3K inhibitor. None has yet to demonstrate an increase of T-regs in vivo.

Toxoplasmic encephalitis, a life-threatening infection of the CNS by *Toxoplasma gondii*, represents the most common cause of focal neurological disease in patients with AIDS (74, 75). Although HAART is able to partially restore *T. gondii*-specific immune responses in patients with advanced HIV-infection, this infection persists also under effective HAART treatment (76). Furthermore, increased anti-*T. gondii* antibody titres in HAART-treated subjects are predictive of the occurrence of toxoplasmic encephalitis. In particular, anti-*T. gondii* IgG antibody titres ≥150 IU/mL are predictive of infection reactivation and occurrence of encephalitis (77).

The HIV-1 Tat protein is a regulatory protein produced early after infection, which plays key roles in HIV replication and AIDS pathogenesis. In HIV-1 infected individuals, the presence of a humoral immune response to Tat is associated with a reduced risk of disease progression. In natural infection, however, anti-Tat antibodies are produced by only a very small fraction of individuals, predominantly in the asymptomatic stage with similar frequencies in different geographical regions, which harbour different HIV-1 subtypes. In contrast, high titres of antibodies are produced against virtually all other regulatory and structural viral gene products (92).

The development of such a limited antibody response against Tat is peculiar, and may depend on the predominant induction of Th1 T-cell polarisation seen during the generation of the anti-Tat adaptive immune response (93, 94), and this may play a role in disease pathogenesis by acting as a mechanism for eluding or diverting the anti-viral immune response. However, when present, cellular and antibody responses to Tat have been found to exert a protective role, namely to control virus replication and to delay progression to disease, both in human and nonhuman primates.

Thus, it is not known why the majority of those infected with HIV do not develop any humoral immunity against Tat, but it is known that the few who do have a considerably better quality of life and often remain asymptomatic.

We have developed a translational program based on the native HIV-1 Tat protein (100). Tat has been studied closely, and observations and/or properties of the active molecule include: i. very early production and extracellular release after infection, and key roles in both the virus life cycle and AIDS pathogenesis (50, 51, 78-85); ii. correlation of anti-Tat immune responses with low or no progression to AIDS in natural infection; iii. specific targeting and uptake of Tat into dendritic cells with induction of cell maturation and Th1 polarisation; iv. modulation of the immunoproteasome leading to altered CTL epitope hierarchy and broadening of cellular responses against heterologous antigens (101-103); and v. high degree of cross-clade immune recognition (91).

Currently, there is no means to prevent the key signs of AIDS progression in infected individuals, nor of the non-AIDS-related illnesses and causes of death, including tumours, cardiovascular, liver and kidney disease, central nervous system disorders, such as encephalitis, persistent infections etc., and the early ageing, which represent critical problems in the clinical management of HIV-related disease. As noted above, there is currently no known means to eliminate or reduce the viral reservoir or to halt immune activation, or to restore normal immune functions in infected individuals, and there is no known means to restore immunity against heterologous antigens including recall antigens or against persistent infections which continue to be present and/or to reactivate during HAART, such as toxoplasmosis, which can lead to encephalitis.

Surprisingly, it has now been found that Tat can save, or restore, a disequilibrated, or dysregulated, immune system in a patient, especially where the disequilibrium accompanies persistent or chronic infection, particularly by HIV. What is particularly surprising is that patients that have been so treated can not only regain some or all of a diminished or lost response to an antigen to which they had previously been exposed, but that HIV patients that are so treated actually build an immune response to HIV and can even eliminate, or eradicate, the virus, with this effect reaching even the virus reservoirs that have so far proven intractable to treatment.

SUMMARY OF THE INVENTION

Accordingly, in a first aspect, the present invention provides native Tat, or a molecule having the immunological properties of native Tat, for use in partially or completely restoring immunocompetence in immunocompromised individuals.

In an alternative aspect, the present invention provides native Tat, or a molecule having the immunological properties of native Tat, for use in countering the immune effects of HIV infection.

As used herein, the term, 'immune effects' means one or more effects on a patient caused directly, or indirectly, by changes to the immune system of the patient resulting from HIV infection.

DETAILED DESCRIPTION

Tat administered to HIV-infected patients is capable of slowing or preventing key signs of AIDS progression, and/or inhibiting and even reversing immune activation, increasing CD4 T cells, B cells, T-regs and central memory T cells, reducing effector memory T cells and/or restoring immune responses against heterologous antigens, including recall antigens, and persistent infections. This has the additional advantage of ameliorating the non-AIDS defining illnesses and causes of death and early ageing, due to the oxidative stress from the dysregulated immune system and/or to the reactivation of other persisting and/or latent pathogens. Administration of Tat to HIV-infected individuals is also accompanied by a reduction of integrated proviral DNA and by an increase of 2-LTR episomal DNA circles, thereby providing the means to reduce viral reservoirs and to eliminate the virus. This is consistent with the reduced amount of proviral DNA and reduced diversity of HIV quasispecies in infected subjects after Tat administration, which indicates a purging of archival proviral DNA first infecting the subject.

'Immunocompetence' is taken as the ability of the immune system of the individual to respond to any challenge by raising a response to new antigens and recognising antigens to which the individual has previously been exposed (recall antigens). An immunocompromised individual is one that typically has a persistent infection, particularly an HIV infection, or who has elevated levels of immune activation, which may also be caused by persistent infection, or who is otherwise in need of restoration of immune function. Restoration of immune function, also referred to as immune reconstitution, is usually a significant part of the restoration of immunocompetence, and may involve restoring the balance of immune cells in the system, including raising levels of $CD4^+$ T cells, the ratio $CD4^+/CD8^+$ T cells, and or T-regs or B cells, for example, or increasing central memory T cells, or reducing effector memory T cells and/or decreasing the amounts of $CD38^+$ $CD8^+$ T cells and/or biochemical/serum markers of immune activation.

In a further aspect, the present invention provides native Tat, or a molecule having the immunological properties of native Tat, for use in restoring immunity to heterologous antigens, including recall antigens and antigens from one or more persistent infections, in an immunocompromised individual.

There is further provided native Tat, or a molecule having the immunological properties of native Tat, for use in slowing, inhibiting, or blocking one or more key signs and/or symptoms of the progression of HIV infection, particularly where said signs and/or symptoms are selected from the group consisting of: persistent immune activation, CD4 T cell decay, reduction of B cells, T-regs and central memory T cells, increase of effector memory T cells, loss of immune functions, and occurrence of non-AIDS defining clinical manifestations, including reactivation of latent infections (i.e. toxoplasmosis) and early ageing.

There is further provided native Tat, or a molecule having the immunological properties of native Tat, for use in reducing levels of immune activation, particularly when related to persistent infections, especially HIV infections.

There is further provided native Tat, or a molecule having the properties of native Tat, for use in increasing $CD4^+$ T cells, or other circulating lymphocytes such as B cells, in persistent infections, particularly HIV infections.

There is further provided native Tat, or a molecule having the properties of native Tat, for use in increasing levels of regulatory T cells, particularly when related to persistent infections, especially HIV infections.

There is further provided native Tat, or a molecule having the properties of native Tat, for use in increasing levels of peripheral blood cell viability, particularly when related to persistent infections, especially HIV infections.

There is further provided native Tat, or a molecule having the properties of native Tat, for use in increasing levels of immune responses related to persistent infections, particularly HIV infections.

There is further provided native Tat, or a molecule having the immunological properties of native Tat, for use in reducing levels of inflammation and reactivation related to chronic diseases/infections, particularly HIV infections.

There is further provided native Tat, or a molecule having the immunological properties of native Tat, for use in inducing anti-pathogen and antiviral responses, particularly anti-HIV responses.

There is further provided native Tat, or a molecule having the immunological properties of native Tat, for use in reducing susceptibility to infections, particularly HIV infections. This aspect includes use to reduce the reactivation of persistent infections. Without being bound by theory, it is believed that this effected by increasing CD38+CD4+ T cells, and the present invention extends to native Tat, or a molecule having the immunological properties of native Tat, for use in increasing CD38+CD4+ T cells.

There is further provided native Tat, or a molecule having the immunological properties of native Tat, for use in increasing central memory T cells and/or reducing effector memory T cells for immune reconstitution and repopulation of lymphoid tissues.

There is further provided native Tat, or a molecule having the immunological properties of native Tat, for inducing antibodies capable of HIV elimination and/or immune restoration.

There is still further provided native Tat, or a molecule having the immunological properties of native Tat, for inducing restoration of B cell responses and antibody repertoire against one or more of recall antigens, persistent infections and new infections.

There is still further provided native Tat, or a molecule having the immunological properties of native Tat, for use in reducing integrated viral DNA, in increasing 2-LTR episomal DNA circles and/or to reduce the virus reservoir, especially to eliminate the virus.

In a further aspect, the present invention provides native Tat, or a molecule having the immunological properties of native Tat, for use in reducing or eliminating HIV infection, optionally including reduction of proviral DNA, and/or virus integration, and/or increase of unintegrated viral DNA, and/or reduction of spreading of infection to new target cells, and/or reducing the number of infected cells replicating the virus.

There is still further provided native Tat, or a molecule having the immunological properties of native Tat, for blocking the establishment of infection and a viral reservoir and/or blocking or inhibiting virus integration.

There is further provided native Tat, or a molecule having the immunological properties of native Tat, for use in blocking or inhibiting integration of a pathogen, preferably a virus, especially HIV, in the host genome and/or increasing unintegrated forms of said pathogen or HIV.

There is further provided native Tat, or a molecule having the immunological properties of native Tat, for use in reducing the viral reservoir. This has the advantage of reducing the need, simplifying, and/or avoiding anti-retroviral treatment.

There is further provided native Tat, or a molecule having the immunological properties of native Tat, for use in eliminating or inhibiting HIV infection and/or symptoms or need of anti-retroviral therapy.

There is further provided native Tat, or a molecule having the immunological properties of native Tat, for blocking or inhibiting immune activation and/or key signs/symptoms of HIV disease, including reduction of viral reservoir or increase of unintegrated proviral DNA.

For the avoidance of doubt, where the expression 'and/or' is used, the present invention envisages the embodiments so linked as separate embodiments that may also be present together, thereby providing said embodiments individually and as a combination.

There is further provided native Tat, or a molecule having the immunological properties of native Tat, for use as immune therapy to eliminate or reduce HIV infection. This has the advantage of reducing or avoiding the need for anti-retroviral therapy.

There is still further provided native Tat, or a molecule having the immunological properties of native Tat, for blocking or inhibiting the development of virus-drug resistance.

There is still further provided native Tat, or a molecule having the immunological properties of native Tat, for blocking or inhibiting virus escape from anti-Env antibodies.

Where the expressions 'blocking or inhibiting', 'eliminate or reduce', and related expressions, are used herein, then it is preferred that the embodiment or aspect concerned inhibits or reduces completely, or substantially completely, as appropriate.

There is still further provided a vaccine comprising an immunologically effective amount of native Tat, or a molecule having the immunological properties of native Tat, for use in countering the immune effects of HIV infection. There is also provided such a vaccine for use in partially or completely restoring immunocompetence in immunocompromised individuals.

There is still further provided native Tat, or a molecule having the immunological properties of native Tat, for use in place of cytokines, especially IL-7, for immunorestoration and/or HIV elimination and/or reducing the need for drugs.

There is still further provided native Tat, or a molecule having the immunological properties of native Tat, for use in blocking or inhibiting reactivation of infection, particularly HIV infection, and/or persistent infections, such as by bacteria, viruses, protozoa, and/or fungi, particularly toxoplasmosis and HAART-resistant infections.

The native Tat or molecule is preferably one that, on administration, gives rise to an immune response, including but not limited to, anti-Tat antibodies, that recognises native Tat. It is preferred that this response has one or more of the following effects, whether by administration of native Tat or the molecule having Tat immunological properties, wherein each effect represents a separate embodiment, or may be achieved in combination with one or more other effects:

a i) countering the immune effects of HIV infections, and/or b i) partially or completely restoring immunocompetence in immunocompromised individuals, and/or c i) in restoring immunity to heterologous antigens, especially recall antigens, in an immunocompromised individual, and/or d i) in slowing, inhibiting, or blocking one or more key signs and/or symptoms of the progression of HIV infection, particularly where said symptoms are selected from the group consisting of: persistent immune activation, CD4 T cell decay, reduction of B cells, T-regs and central memory T cells, increase of effector memory T cells, loss of immune functions, and occurrence of non-AIDS clinical manifestations including reactivation of latent infections (i.e. toxoplasmosis) and early ageing, and/or e i) in reducing levels of immune activation, particularly when related to persistent infections, especially HIV infections, where viral reservoirs represent a relevant obstacle in HIV elimination, and/or f i) in increasing $CD4^+$ T cells, or other circulating lymphocytes such as B cells, in persistent infections, particularly HIV infections, and/or g i) in increasing levels of regulatory T cells, particularly when related to persistent infections, especially HIV infections, and/or h i) in increasing levels of peripheral blood cell viability, particularly when related to persistent infections, especially HIV infections, and/or i i) in increasing levels of immune responses related to persistent infections, particularly HIV infections, and/or j i) in reducing levels of inflammation and reactivation related to chronic diseases/infections, particularly HIV infections, and/or k i) in inducing anti-pathogen and anti-viral responses, particularly anti-HIV responses, and/or
l i) in reducing susceptibility to infections or the reactivation of persistent infections, particularly HIV infections, and/or
m i) in increasing central memory T cells and/or reducing effector memory T cells for immune reconstitution and repopulation of lymphoid tissues, and/or
n i) in elimination of HIV, and/or
o i) in immune restoration, and/or
p i) in inducing restoration of B cell responses and antibody repertoire against recall antigens, persistent infections or new infections, and/or
q i) in reducing integrated viral DNA, in increasing 2-LTR episomal DNA circles and/or to reduce the virus reservoir and/or eliminating the virus over time, and/or
r i) in eliminating or reducing HIV infection, especially including reduction of proviral DNA, and/or virus integration, and/or increase of unintegrated viral DNA, and/or reduction of spreading of infection to new target cells, and/or reduction of number of infected cells replicating the virus, and/or
s i) in blocking or inhibiting the establishment of infection and a viral reservoir and/or block or inhibiting virus integration, and/or
t i) in blocking or inhibiting integration of a pathogen, preferably a virus, especially HIV, in the host genome and/or increasing unintegrated forms of said pathogen, and/or
u i) in reducing the viral reservoir, such as to reduce the need, to simplify, and/or to avoid anti-retroviral treatment, and/or
v i) in elimination or reducing HIV infection/symptoms and/or need for anti-retroviral therapy, and/or
w i) in blocking or reducing immune activation and/or key signs/symptoms of HIV disease, especially including reduction of viral reservoir or increase of unintegrated proviral DNA, and/or
x i) immune therapy to eliminate or reduce HIV infection or reducing or avoiding the need of anti-retroviral therapy, and/or
y i) in blocking or reducing development of virus-drug resistance, and/or
z i) in blocking or reducing virus escape from anti-Env antibodies, and/or
a ii) which antibody or molecule is effective in the production of an Env vaccine in a preventative and/or therapeutic setting, and/or b ii) which antibody or molecule is used in place of a cytokine, especially IL-7, for immunorestoration and/or HIV elimination and/or reducing need of drugs, and/or c ii) in blocking or inhibiting reactivation of infection, particularly HIV infection, and/or persistent infections, such as bacteria, viruses, protozoa, and/or fungi, for example toxoplasmosis and HAART-resistant infections.

Preferred embodiments and aspects are as follows:

i. Native Tat, or a molecule having the immunological properties of native Tat, for use in countering the immune effects of HIV infections.

ii. Native Tat, or a molecule having the immunological properties of native Tat, for use in partially or completely restoring immunocompetence in immunocompromised individuals.

iii. Native Tat, or a molecule having the immunological properties of native Tat, for use in restoring immunity to heterologous antigens, including recall antigens, in an immunocompromised individual.

iv. Native Tat, or a molecule having the immunological properties of native Tat, for use in slowing, inhibiting, or blocking one or more key signs of the progression of HIV infection, particularly where said signs are selected from the group consisting of: persistent immunoactivation, loss of regulatory T-cells, CD4 T cell decay, loss of central memory T cells, increase of effector memory T cells, loss of immune functions, non-AIDS defining illnesses such as cardiovascular, liver, and kidney, early aging, and other conditions caused by oxidative stresses. Other preferred signs include loss of B cells, and illness of the central nervous system.

v. Native Tat, or a molecule having the immunological properties of native Tat, for use in reducing levels of immunoactivation related to immune disorders and/or to persistent infections (bacteria, viruses, protozoa, fungi), particularly HIV infections.

vi. Native Tat, or a molecule having the properties of native Tat, for use in increasing CD4+ T cells, or other circulating lymphocytes, such as B cells, immune disorders and/or in persistent infections, particularly HIV infections.

vii. Native Tat, or a molecule having the properties of native Tat, for use in increasing levels of regulatory T cells related to immune disorders and/or to persistent infections, particularly HIV infections.

viii. Native Tat, or a molecule having the properties of native Tat, for use in increasing levels of peripheral blood cell viability related to immune disorders and/or persistent infections, particularly HIV infections.

ix. Native Tat, or a molecule having the properties of native Tat, for use in increasing levels of immune responses related to immune disorders and/or persistent infections, particularly HIV infections.

x. Native Tat, or a molecule having the immunological properties of native Tat, for use in reducing levels of inflammation related to chronic diseases/infections, particularly HIV infections.

xi. Native Tat, or a molecule having the immunological properties of native Tat, for use in inducing anti-pathogen and antiviral responses, particularly by increasing CD38+ HLA-DR+CD8+ T cells, particularly anti-HIV responses.

xii. Native Tat, or a molecule having the immunological properties of native Tat, for use in reducing susceptibility to infections, particularly by increasing CD38+CD4+ T cells, particularly HIV infections.

xiii. Native Tat, or a molecule having the immunological properties of native Tat, for use in increasing central memory T cells and/or reducing effector memory T cells for immune reconstitution and repopulation of lymphoid tissues.

viv. A method for countering the immune effects of HIV infection, comprising administering a physiologically effective amount of native Tat, or a molecule having the immunological properties of native Tat, to a patient in need thereof.

xv. A method for partially or completely restoring immunocompetence in an immunocompromised individual, comprising administering a physiologically effective amount of native Tat, or a molecule having the immunological properties of native Tat, to an individual in need thereof.

xvi. A method for restoring immunity to heterologous antigens, including recall antigens, in an immunocompromised individual, comprising administering a physiologically effective amount of native Tat, or a molecule having the immunological properties of native Tat, to an individual in need thereof.

xvii. A method for slowing, inhibiting, or blocking one or more key signs of the progression of HIV infection, particularly where said signs are selected from the group consisting of: persistent immunoactivation, reduction of central memory T cells, increase of effector memory T cells, loss of regulatory T-cells, CD4 T cell decay, loss of immune functions, non-AIDS defining illnesses such as cardiovascular, liver, and kidney, early aging, and other conditions caused by oxidative stresses. Other preferred signs include loss of B cells, and illness of the central nervous system.

xviii. A method for reducing levels of immunoactivation related to immune disorders and/or to persistent infections, particularly HIV infections, comprising administering a physiologically effective amount of native Tat, or a molecule having the immunological properties of native Tat, to an individual in need thereof.

xix. A method for increasing levels of circulating lymphocytes, such as B cells, and/or CD4 T cells in the presence of persistent infections, particularly HIV infections, comprising administering an effective amount of native Tat, or a molecule having the properties of native Tat, to an individual in need thereof.

Particularly preferred aspects and embodiments include:

I. Native Tat, or a molecule having the immunological properties of native Tat, for use in partially or completely restoring immunocompetence in an immunocompromised individual, especially where the individual has a persistent infection, and particularly where the persistent infection is an HIV infection.

II. The restoration preferably comprises restoration of immunity, in part or in whole, to at least one recall antigen. The recall antigen is preferably associated with an existing infection of the individual, but may also be to a previous infection.

III. The restoration of immunocompetence is preferably effective to counter the immune effects of HIV infection.

IV. Native Tat, or a molecule having the immunological properties of native Tat, for use in slowing, inhibiting, or blocking, one or more key signs and/or symptoms of the progression of HIV infection, particularly where said signs are selected from the group consisting of: immune activation; loss of regulatory T-cells, CD4 T cells, B cells, and/or central memory T cells; increase of effector memory T cells; loss of immune functions; occurrence of non-AIDS defining illnesses, such as cardiovascular, liver, kidney, and/or central nervous system disorders, including encephalitis, early aging, and other conditions caused by oxidative stresses; persistent infections, such as toxoplasmosis; and combinations thereof.

V. The restoration of immunocompetence preferably comprises reducing levels of immune activation and/or reactivation, especially where said activation and/or reactivation are related to immune disorders and/or to persistent infections, said infections being optionally selected from the group consisting of: bacteria, viruses, protozoa, fungi, HIV, toxoplasmosis, HAART-resistant infections, and combinations thereof.

VI. Native Tat, or a molecule for use according to any preceding claim, wherein said restoration comprises increasing CD4+ T cells, especially regulatory T cells, or other circulating lymphocytes, such as B cells.

VII. The use of the invention where levels of inflammation and reactivation associated with chronic infection are reduced.

VIII. The use of the invention where an anti-pathogen response is induced, and wherein the individual has a chronic infection of the pathogen, especially where the pathogen is HIV.

IX. The use of the invention where antibodies are induced that are capable of HIV eradication.

X. The restoration preferably comprises the restoration of: B cell responses; antibody repertoire against recall antigens, including persistent infections; and the ability to respond to new infections.

XI. The use of the invention preferably comprises enabling the immune system of the individual to reduce integrated viral DNA, and/or increase of 2-LTR episomal DNA circles, and/or inhibit the infection of new target cells, and/or in reducing the number of infected cells replicating the virus, preferably all.

XII. The use of the invention preferably comprises enabling the immune system of the individual to block or inhibit the establishment of infection and to block or inhibit the establishment of viral reservoirs and/or to block virus integration and/or to increase unintegrated forms of virus, wherein the virus is HIV.

XIII. The native Tat, or a molecule having the immunological properties of native Tat, in a form capable of generating an anti-Tat response in an individual infected with HIV, in combination with an Env vaccine, for use in treating an HIV infection. The Env vaccine may be administered before, after, or with the Tat or molecule which, in turn, is preferably in the form of a vaccine. One or more boosters of either or both vaccines may be administered.

XIV. The native Tat, or a molecule having the immunological properties of native Tat, in the form of a vaccine.

It will be appreciated that the native Tat of the present invention is biologically active Tat. Native Tat may be produced recombinantly, for instance. The specific and preferred example is that from HTLV-III strain, clone BH-10. It may, for instance be produced in *E. coli* and may be purified by DEAE and Heparin Sepharose chromatography. As described in WO 2005/090391, the Tat is preferably recognisable by a monoclonal antibody directed against the CCR5 second extracellular loop described by (104), and indeed is preferably capable of binding a region on the virus Envelope (Env) comprising residues 301-419 of gp120.

Other preferred aspects and embodiments of the invention may be found in the accompanying claims.

A molecule having the immunological properties of native Tat is one that, on administration, gives rise to an immune response that recognises native Tat. Typically, such a molecule will be a part of native Tat, or is synthetic Tat, corresponding to part or all of the native Tat molecule, or comprising one or more modifications well known in the art, such as mutation, replacements, deletions, insertions or inversions. This applies equally to a nucleotide sequence, if used together with an expression vehicle. However, it is generally preferred to administer the Tat as an amino acid sequence, or protein in a medicinal form suitable for human use.

The invention further provides anti-Tat molecules for use, for example, as passive immunization. Such vaccines are referred to as passive vaccines, and may be used in similar circumstances to those in which native Tat is used, as above, where the immediate presence of anti-Tat molecules is desired or required. Such molecules include, but are not limited to, anti-Tat antibodies and Tat-recognising antibody chains and fragments thereof, and constructs comprising one or more Tat-binding regions thereof, which may be synthetic.

In the vaccine formulation form, the vaccine may comprise as much Tat as desired, preferably at least 1 µg and up to about 100 µg or 150 µg, but greater or lesser amounts may be used, as desired. A preferred range is 5 µg to 120 µg, and more preferably 20 µg to 60 µg, preferably 20 µg to 50 µg. Amounts in the region of 30 µg have been found to work well. The vehicle may be anything appropriate, according to medicinal chemistry practise, such as buffered saline, and other formulation ingredients, such as isotonic agents, excipients, adjuvants and others may be employed, if desired, although it is not generally necessary to use adjuvants when administering Tat.

The vaccine may be administered in any suitable manner, such as intraperitoneal, intramuscular, intravenous, intradermal, intranasal, oral, such as mucosal or parenteral. A preferred route is intradermal.

The vaccine may be administered once, and is preferably followed by a second booster shot. More preferably, the vaccine is administered at least three times, with a suitable interval, typically ranging from two weeks to several months between shots. Multiple doses, each about one month apart, have been found to be useful, and a three or five dose vaccination regimen over two or four months, respectively, each dose being a month apart, has been found to be useful. The treatments of the present invention are particularly appropriate to individuals infected with HIV, whether they are symptomatic or asymptomatic, in the presence or absence of therapy. Even those with severe infections may be treated, provided that their immune systems have not been completely deleted and unable to regenerate.

The present invention is suitable to counter the immunological effects of HIV infection, especially in combination with other therapy, particularly antiretroviral therapy, and especially HAART. Together with HAART, there appears to be synergy, and especially good results are achieved.

The present invention can reduce the virus reservoir and slow down or even prevent the key signs of AIDS progression, including persistent or elevated immune activation, loss of immune function, such as depletion of $CD4^+$ cells, B cells, T-regs and central memory T cells as well as the occurrence of non-AIDS defining illnesses and especially accelerated ageing.

The present invention is also capable of reducing the elevated levels of markers of immune activation, especially levels of CD38 on CD8 T cells and biochemical markers. It also leads to increases in levels of $CD4^+$ T cells and other circulating lymphocytes, including B cells and regulatory T cells.

Importantly, administration of Tat can restore immune responses to heterologous antigens, including recall antigens, regardless of origin, as demonstrated herein.

For all of the various uses of the present invention, administration form and dosage regime are the generally the same, although the skilled physician may vary the parameters as appropriate.

The present invention further provides a method for countering the immune effects of HIV infection, comprising administering a physiologically effective amount of native Tat, or a molecule having the immunological properties of native Tat, to a patient in need thereof.

By physiologically effective is meant an amount that will stimulate an immune response, either alone, or in combination with one or more subsequent booster shots.

Patients, or individuals being treated, are preferably mammalian, more preferably apes, and most preferably humans.

In an alternative aspect, the present invention provides a method for partially or completely restoring immunocompetence in an immunocompromised individual, comprising administering native Tat, or a molecule having the immunological properties of native Tat, to an individual in need thereof.

In a further aspect, the present invention provides a method for restoring immunity against heterologous antigens, including recall antigens in an immunocompromised individual, comprising administering native Tat, or a molecule having the immunological properties of native Tat, to an individual in need thereof.

In a further aspect, the present invention provides a method for slowing or stopping key signs of AIDS progression and non-AIDS illnesses in HIV infected individuals, comprising administering native Tat, or a molecule having the immunological properties of native Tat, to an individual in need thereof.

In a further aspect, the present invention provides a method for reducing levels of immune activation related to persistent infections, particularly HIV infections, comprising administering native Tat, or a molecule having the immunological properties of native Tat, to an individual in need thereof.

In a further aspect, the present invention provides a method for increasing $CD4^+$ T cells, or other circulating lymphocytes, such as B cells, related to immune disorders and/or to persistent infections, particularly HIV infections, comprising administering native Tat, or a molecule having the immunological properties of native Tat, to an individual in need thereof.

In a further aspect, the present invention provides a method for increasing levels of regulatory T cells related to immune disorders and/or to persistent infections, particularly HIV infections, comprising administering native Tat, or a molecule having the immunological properties of native Tat, to an individual in need thereof.

In a further aspect, the present invention provides a method for increasing levels of peripheral blood cell viability related to immune disorders and/or persistent infections, particularly HIV infections, comprising administering native Tat, or a molecule having the immunological properties of native Tat, to an individual in need thereof.

In a further aspect, the present invention provides a method for increasing levels of immune responses related to immune disorders and/or persistent infections, particularly HIV infections, comprising administering native Tat, or a molecule having the immunological properties of native Tat, to an individual in need thereof.

In a further aspect, the present invention provides a method for reducing levels of inflammation and reactivation related to chronic diseases/infections, particularly HIV infections, comprising administering native Tat, or a molecule having the immunological properties of native Tat, to an individual in need thereof.

In a further aspect, the present invention provides a method for inducing anti-pathogen and antiviral responses, particularly anti-HIV responses, comprising administering native Tat, or a molecule having the immunological properties of native Tat, to an individual in need thereof.

In a further aspect, the present invention provides a method for reducing susceptibility to infections, or the reactivation of persistent infections, particularly HIV infections, comprising administering native Tat, or a molecule having the immunological properties of native Tat, to an individual in need thereof.

In a further aspect, the present invention provides a method for increasing central memory T cells and/or reducing effector memory T cells for immune reconstitution and repopulation of lymphoid tissues, comprising administering native Tat, or a molecule having the immunological properties of native Tat, to an individual in need thereof.

In a further aspect, the present invention provides a method for inducing antibodies capable of HIV elimination and/or immune restoration, comprising administering native Tat, or a molecule having the immunological properties of native Tat, to an individual in need thereof.

In a further aspect, the present invention provides a method for inducing restoration of B cell responses and antibody repertoire against recall antigens, persistent infections or new infections, comprising administering native Tat, or a molecule having the immunological properties of native Tat, to an individual in need thereof.

In a further aspect, the present invention provides a method for reducing integrated viral DNA, in increasing 2-LTR episomal DNA circles and/or to reduce the virus reservoir and to eliminate the virus, comprising administering native Tat, or a molecule having the immunological properties of native Tat, to an individual in need thereof.

In a further aspect, the present invention provides a method for promoting elimination of HIV infection, including reduction of proviral DNA, and/or virus integration, and/or increase of unintegrated DNA and/or reducing spreading of infection to new target cells, and/or reducing the number of infected cells replicating the virus, comprising administering native Tat, or a molecule having the immunological properties of native Tat, to an individual in need thereof.

In a further aspect, the present invention provides a method for blocking the establishment of infection and a viral reservoir and/or blocking virus integration, comprising administering native Tat, or a molecule having the immunological properties of native Tat, to an individual in need thereof.

In a further aspect, the present invention provides a method for blocking integration of HIV or other pathogens in the host genome and/or increasing unintegrated forms of HIV or other pathogens including viruses, comprising administering native Tat, or a molecule having the immunological properties of native Tat, to an individual in need thereof.

In a further aspect, the present invention provides a method for reducing the viral reservoir and reducing the need, simplifying, and/or avoiding anti-retroviral treatment, comprising administering native Tat, or a molecule having the immunological properties of native Tat, to an individual in need thereof.

In a further aspect, the present invention provides a method for elimination of HIV infection/symptoms or need of anti-retroviral therapy, comprising administering native Tat, or a molecule having the immunological properties of native Tat, to an individual in need thereof.

In a further aspect, the present invention provides a method for blocking immune activation and/or key signs/symptoms of HIV disease, including reduction of viral reservoir or increase of unintegrated proviral DNA, comprising administering native Tat, or a molecule having the immunological properties of native Tat, to an individual in need thereof.

In a further aspect, the present invention provides a method of immune therapy to eliminate HIV infection or to reduce or avoid the need for anti-retroviral therapy, comprising administering native Tat, or a molecule having the immunological properties of native Tat, to an individual in need thereof.

In a further aspect, the present invention provides a method for blocking development of virus-drug resistance, comprising administering native Tat, or a molecule having the immunological properties of native Tat, to an individual in need thereof.

In a further aspect, the present invention provides a method for blocking virus escape from anti-Env antibodies, comprising administering native Tat, or a molecule having the immunological properties of native Tat, to an individual in need thereof.

In a further aspect, the present invention provides a method for making an effective Env vaccine in both the preventative and/or therapeutic setting, comprising administering native Tat, or a molecule having the immunological properties of native Tat, to an individual in need thereof.

In a further aspect, the present invention provides a method for substitution of cytokines, including IL-7, for immunorestoration and/or HIV elimination and/or reducing need of drugs, comprising administering native Tat, or a molecule having the immunological properties of native Tat, to an individual in need thereof.

In a further aspect, the present invention provides a method for blocking reactivation of infection, particularly HIV infection, and persistent infections, such as bacteria, viruses, protozoa, and/or fungi, especially toxoplasmosis and HAART-resistant infections, comprising administering native Tat, or a molecule having the immunological properties of native Tat, to an individual in need thereof.

In a further aspect, the present invention provides a method for inducing anti-Tat antibodies for countering the immune effects of HIV infection, comprising administering native Tat, or a molecule having the immunological properties of native Tat, to an individual in need thereof.

In a further aspect, the present invention provides a method for inducing anti-Tat antibodies, for partially or completely restoring immunocompetence in immunocompromised individuals, comprising administering native Tat, or a molecule having the immunological properties of native Tat, to an individual in need thereof.

In a further aspect, the present invention provides a method for inducing anti-Tat antibodies, for restoring immunity to heterologous antigens, including recall antigens, in an immunocompromised individual, comprising administering native Tat, or a molecule having the immunological properties of native Tat, to an individual in need thereof.

There is further provided a method for inducing anti-Tat antibodies, for slowing, inhibiting, or blocking one or more key symptoms of the progression of HIV infection, particularly where said symptoms are selected from the group consisting of: persistent immune activation, CD4 T cell decay, reduction of B cells, T-regs and central memory T cells, increase of effector memory T cells, loss of immune functions, and occurrence of non-AIDS clinical manifestations including reactivation of latent infections (i.e. Toxoplasmosis) and early ageing, comprising administering native Tat, or a molecule having the immunological properties of native Tat, to an individual in need thereof.

There is further provided a method for inducing anti-Tat antibodies, for reducing levels of immune activation, particularly when related to persistent infections, especially HIV infections, where viral reservoirs represent a relevant obstacle in HIV elimination, comprising administering native Tat, or a molecule having the immunological properties of native Tat, to an individual in need thereof.

There is further provided a method for inducing anti-Tat antibodies, for increasing CD4+ T cells, or other circulating lymphocytes such as B cells, in persistent infections, particularly HIV infections, comprising administering native Tat, or a molecule having the immunological properties of native Tat, to an individual in need thereof.

There is further provided a method for inducing anti-Tat antibodies, for increasing levels of regulatory T cells, particularly when related to persistent infections, especially HIV infections, comprising administering native Tat, or a molecule having the immunological properties of native Tat, to an individual in need thereof.

There is further provided a method for inducing anti-Tat antibodies, for increasing levels of peripheral blood cell viability, particularly when related to persistent infections, especially HIV infections, comprising administering native Tat, or a molecule having the immunological properties of native Tat, to an individual in need thereof.

There is further provided a method for inducing anti-Tat antibodies, for increasing levels of immune responses related to persistent infections, particularly HIV infections, comprising administering native Tat, or a molecule having the immunological properties of native Tat, to an individual in need thereof.

There is further provided a method for inducing anti-Tat antibodies, for reducing levels of inflammation and reactivation related to chronic diseases/infections, particularly HIV infections, comprising administering native Tat, or a molecule having the immunological properties of native Tat, to an individual in need thereof.

There is further provided a method for inducing anti-Tat antibodies, for inducing anti-pathogen and antiviral responses, particularly by increasing CD38+HLA-DR+ CD8+ T cells, particularly anti-HIV responses, comprising administering native Tat, or a molecule having the immunological properties of native Tat, to an individual in need thereof.

There is further provided a method for inducing anti-Tat antibodies, for reducing susceptibility to infections or their reactivation, particularly HIV infections, comprising administering native Tat, or a molecule having the immunological properties of native Tat, to an individual in need thereof.

There is further provided a method for inducing anti-Tat antibodies, for increasing central memory T cells and/or reducing effector memory T cells for immune reconstitution and repopulation of lymphoid tissues, comprising administering native Tat, or a molecule having the immunological properties of native Tat, to an individual in need thereof.

There is further provided a method for inducing anti-Tat antibodies capable of HIV elimination and/or immune restoration, comprising administering native Tat, or a molecule having the immunological properties of native Tat, to an individual in need thereof.

There is further provided a method for inducing anti-Tat antibodies, for inducing restoration of B cell responses and antibody repertoire against recall antigens, persistent infections or new infections, comprising administering native Tat, or a molecule having the immunological properties of native Tat, to an individual in need thereof.

In a further aspect, the present invention provides a method for reducing integrated viral DNA, in increasing 2-LTR episomal DNA circles and/or to reduce the integrated proviruses (virus reservoir) and/or to eliminate the virus upon time, and/or to eliminate and/or reduce the need of drugs, comprising administering native Tat, or a molecule having the immunological properties of native Tat, to an individual in need thereof.

In a further aspect, the present invention provides a method for inducing anti-Tat antibodies, for promoting elimination of HIV infection, including reduction of proviral DNA, and/or virus integration, and/or increase of unintegrated viral DNA, and/or reduction of spreading of infection to new target cells, and/or reduction of the number of infected cells actively replicating the virus, comprising administering native Tat, or a molecule having the immunological properties of native Tat, to an individual in need thereof.

There is further provided a method for inducing anti-Tat antibodies, for blocking the establishment of infection and a viral reservoir and/or block virus integration, comprising administering native Tat, or a molecule having the immunological properties of native Tat, to an individual in need thereof.

There is further provided a method for inducing anti-Tat antibodies, for blocking integration of HIV or other pathogens in the host genome and/or increasing unintegrated forms of HIV or other pathogens including viruses, comprising administering native Tat, or a molecule having the immunological properties of native Tat, to an individual in need thereof.

There is further provided a method for inducing anti-Tat antibodies, for reducing the viral reservoir and reducing the need, simplifying, and/or avoiding anti-retroviral treatment, comprising administering native Tat, or a molecule having the immunological properties of native Tat, to an individual in need thereof.

There is further provided a method for inducing anti-Tat antibodies, for elimination of HIV infection/symptoms or need of anti-retroviral therapy, comprising administering native Tat, or a molecule having the immunological properties of native Tat, to an individual in need thereof.

There is further provided a method for inducing anti-Tat antibodies, for blocking immune activation and key signs/symptoms of HIV disease, including reduction of viral reservoir or increase of unintegrated proviral DNA, comprising administering native Tat, or a molecule having the immunological properties of native Tat, to an individual in need thereof.

There is further provided a method for inducing anti-Tat antibodies, for use as immune therapy to eliminate HIV infection or reducing or avoiding the need of anti-retroviral therapy, comprising administering native Tat, or a molecule having the immunological properties of native Tat, to an individual in need thereof.

There is further provided a method for inducing anti-Tat antibodies, for blocking development of virus-drug resistance, comprising administering native Tat, or a molecule having the immunological properties of native Tat, to an individual in need thereof.

There is further provided a method for inducing anti-Tat antibodies, for blocking virus escape from anti-Env antibodies, comprising administering native Tat, or a molecule having the immunological properties of native Tat, to an individual in need thereof.

There is further provided a method for inducing anti-Tat antibodies, to enhance an Env vaccine, comprising administering native Tat, or a molecule having the immunological properties of native Tat, to an individual in need thereof and who is receiving said Env vaccine. There is also provided native Tat, or a molecule having the immunological properties of native Tat, for use to induce anti-Tat antibodies to enhance the therapeutic effects of an Env vaccine.

There is further provided a method for inducing anti-Tat antibodies, for substitution of cytokines, including IL-7, for immunorestoration and/or HIV elimination and/or reducing need of drugs, comprising administering native Tat, or a molecule having the immunological properties of native Tat, to an individual in need thereof.

There is further provided a method for inducing anti-Tat antibodies, for blocking reactivation of infection, particularly HIV infection, and persistent infections (bacteria, viruses, protozoa, fungi), including toxoplasmosis and HAART-resistant infections, comprising administering native Tat, or a molecule having the immunological properties of native Tat, to an individual in need thereof.

Figure 1:
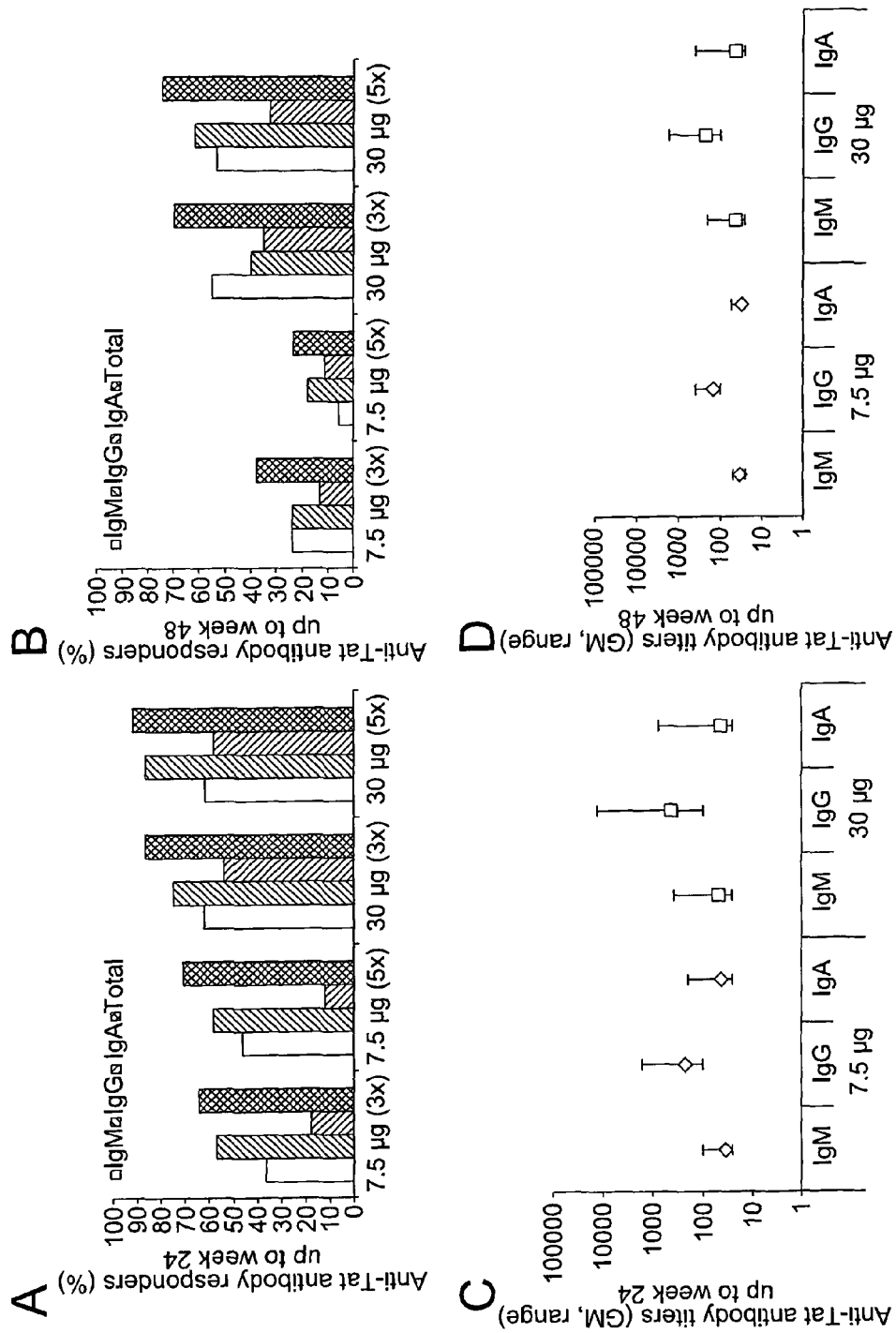
FIG. 1 shows anti-Tat humoral immune responses after Tat immunization.

Previous preclinical animal studies have demonstrated that vaccination with native, biologically active, Tat protein is safe, and elicits broad and specific immune responses, which induce in monkeys long-term protection against pathogenic virus challenge (105-110). Based on these data, phase I placebo-controlled clinical trials were conducted with the recombinant, biologically active, Tat protein in both seronegative and seropositive asymptomatic individuals. Results indicated that immunisation with Tat is safe and induces a strong and balanced immune response in both uninfected and infected individuals (100, 111-115). In particular, in HIV-infected asymptomatic individuals, intradermal immunisation with Tat (given 5 times monthly), in the absence of adjuvant, not only induced functional antibodies, but also partially reverted the marked Th1 polarisation of anti-Tat immunity seen in natural infection (100, 111-115), eliciting a more balanced Th1/Th2 immune response. Remarkably, the number of $CD4^+$ T cells had a statistically significant positive correlation with anti-Tat antibody titres, which persisted up to 144 weeks after the first immunisation (111, 113, 115).

Based on these results, a phase II study was performed with Tat (7.5 or 30 μg given intradermally without adjuvant either 3 or 5 times monthly), involving 160 HAART-treated individuals, negative for anti-Tat antibodies at baseline, with undetectable plasma viral load (viral <50 copies/ml in the last 6 months before enrolment), with $CD4^+$ T cell counts ≥200 cells/mL (see Methods and Table 1). Moreover, 88 individuals with the same characteristics, enrolled in a parallel observational study conducted in the same clinical centres, were used as a reference group (OBS) for intergroup comparison (see Methods and Table 2).

Our data indicate that therapeutic immunisation with Tat in HAART-treated and virologically-suppressed individuals is safe, generates both humoral and cellular Tat-specific immune responses but, most significantly, is capable of reverting signs of AIDS progression as indicated by the reduction of the viral reservoir and integrated HIV DNA, of immune activation and of effector memory T cells, the increase of $CD4^+$ T cells, T-regs, central memory T cells, and B cells, as well as the reduction of T cell dysfunction, and of the reactivation of persistent infections, such as *Toxoplasma gondii*, which are still present even under an effective antiretroviral treatment (3, 5, 6, 11, 13, 15-17, 21, 22). In fact, little or no changes of these parameters, or, more often, a further increase were observed in OBS subjects during follow-up, despite HAART-driven viral suppression in these subjects.

Tat immunisation significantly reduced immune activation, including $CD38^+/CD8^+$ T cells, while expanded regulatory T-cells ($CD4^+/CD25^+/FOXP3^+$). This was associated with reduction of serum β2-microglobulin, neopterin and total immunoglobulins, and correlated with anti-Tat antibody titres. A significant increase of peripheral blood cell viability, number and percentage of $CD4^+$ T cells, and B cells, and of the $CD4^+/CD8^+$ T cell ratio, as well as increases of central memory $CD4^+$ and $CD8^+$ T cells together with reduction of effector memory CD4 and CD8 T cells, and increases of $CD4^+$ and $CD8^+$ T cell responses against Env and recall antigens were also observed upon immunisation as compared to OBS. Moreover, reduction of integrated HIV DNA with a concomitant increase of unintegrated, 2-LTR episomal DNA circles, and reduction of high antibody titres, ≥150 IU/mL, against *Toxoplasma gondii*, which predict the occurrence of encephalitis, were also observed upon immunization as compared to OBS. For all above parameters, greater therapeutic effects were significantly seen in subjects immunised with 30 μg of Tat, especially in more compromised individuals.

In more detail, we have shown that therapeutic immunisation with Tat protein is capable of significantly reducing phenotypic and biochemical immune activation parameters that, at baseline, were still altered under HAART in both trial and OBS subjects. Of note, in the OBS group immune activation markers continued to increase and T-regs decreased during the observation period. In contrast, in Tat-immunised individuals, a significant reduction of $CD38^+/CD8^+$ T cells, which corresponded to the dose of Tat, was inversely related to anti-Tat IgA titres, as well as to the increase of PBMC viability. Without being bound by theory, this appears to suggest that cell death mechanisms, likely induced by the chronic immune activation (116-118), are blocked by Tat immunisation.

Increments of HLA-DR, either alone or in association with CD38, on CD8 T cells and of CD38 on CD4 T cells were also observed. This is advantageous, as CD8 T cells expressing HLA-DR and CD38 have been reported to possess optimal antiviral functionality (119, 120), and the higher expression of CD38 on $CD4^+$ T cells has been reported to reduce T cell susceptibility to HIV productive infection in vitro (121) and in lymph nodes (122).

Without being bound by theory, the mechanism for a such down-regulation of systemic immune activation appears to be related to the increments of the frequency and number of $CD4^+/CD25^+/FOXP3^+$ T-regs (123-128). This is more pronounced with higher doses, such as following the administration of a 30 µg dose of Tat. Such an increase, already apparent at 8 weeks after the first immunisation, became statistically significant at week 12, in our study, preceding and later on accompanying CD38 down-regulation on $CD8^+$ T cells. The increments of T-regs and the reduced immune activation upon Tat immunisation are both advantageous. T-regs, which are known to suppress immune activation, thus governing immune tolerance and termination of adaptive immune responses (72, 73), appear to be progressively reduced in HIV infected individuals, even under successful HAART (123-128), as also observed here in the OBS subjects. The decrease of regulatory T cells correlates with excessive activation and apoptosis of CD8+ T cells in HIV-1-infected typical progressors, but not in long-term non-progressors.

An increase or stability of the number of circulating lymphocytes was observed in immunised subjects as compared to OBS. In particular, the percentage of all Tat-immunised individuals experiencing $CD4^+$ T cell and B cell increases was significantly greater as compared to OBS subjects. When considering increases greater than 50 cells/µL, for example, Tat doses of around 10 µg and above, preferably 20 µg and above, especially about 30 µg, and at a regimen of 3 or more times monthly, are preferred. In addition, increase of central memory CD4 and CD8 T cells and a decrease of effector memory CD4 and CD8 T cells were also observed upon vaccination. In contrast, the opposite occurs upon HIV infection where they are, respectively, reduced and increased, and not restored by antiretroviral therapies or other therapies used in these patients. Without being bound by theory, this suggests that immunisation with Tat may promote the restoration of the physiological immune system functions and immune cell subsets distribution, and may induce repopulation of lymphoid organs such as lymph nodes and gut, which are depleted of central memory T cells by HIV infection (129).

In such a scenario, the increment or de novo appearance of cellular adaptive immune responses against HIV Env as well as to recall antigens, suggest that a restoration of key immune parameters is consistently taking place upon Tat immunisation. Indeed, the pattern of the expression of HLA-DR, either alone or in association with CD38 on $CD4^+$ and $CD8^+$ T cells in response to Tat immunisation, is consistent with that induced in the immunocompetent host by vaccination with heterologous antigens (130). Similarly, the reduction of high anti-*Toxoplasma gondii* antibodies (IgG), which predict pathogen reactivation and occurrence of encephalitis, which are still present in HAART-treated individuals, is consistent with that present in an immune competent host. Similarly, restoration of B cell responses and antibody repertoire against recall antigens, persistent infections or new infections is envisaged by the increase of B cell number and percentage and by the increase of all immune functions and by the immune restoration observed in vaccinated subjects.

It is a particular advantage of the present invention that immunisation with Tat can act in synergy with antiretroviral drugs to yield a restoration of homeostatic immune functions including the recovery of previously lost or dysfunctional immune responses. Indeed, the more dysregulated at baseline, the higher were the therapeutic effects of Tat immunisation (Table 7). It is of note that immunised subjects experienced a reduction of integrated proviral DNA with a concomitant increase of the episomal unintegrated viral DNA, which indicate that a reduction of the viral reservoir is taking place, representing a step toward virus elimination. In fact, a reduced proviral DNA and HIV quasispecie diversity is seen in infected subjects after immunisation, indicating a purging of the archival virus first infecting the individual, which, however, is unable to re-infect since the combined presence of anti-Tat and anti-Env antibodies blocks virus entry into cells and increases virus neutralisation blocking also virus escape mechanisms used by the virus to avoid the neutralising effects of anti-Env antibodies.

EXAMPLES

Methods
Study Design (T-002 and OBS T-002)

The therapeutic phase II study is a randomised, open label clinical trial of the recombinant, biologically active, HIV-1 Tat protein in anti-Tat antibody negative, HIV-1 chronically infected adult subjects of either gender, 18-55 years of age, with HAART-suppressed HIV-1 replication (levels of plasma viraemia <50 copies/mL in the last 6 months prior to the screening), with $CD4^+$ T cells counts ≥200 cells/µL. This study was directed at evaluating the immunogenicity (as a primary end-point) and the safety (as a secondary end-point) of the therapeutic immunisation based on the biologically active Tat protein (ClinicalTrials.gov n. NCT00751595), and it is conducted in the following 11 clinical centres in Italy: Policlinico of Modena; S. Raffaele and Sacco Hospital, Milan; Amedeo di Savoia Hospital, Turin; "Spedali Civili", Brescia; Arcispedale S. Anna, Ferrara; S. Maria Annunziata Hospital, Florence; IFO-San Gallicano, Rome; Policlinico of Bari, Bari; S.M. Goretti Hospital, Latina, Azienda Ospedaliera S. Gerardo, Monza.

Subjects were randomised into 2 arms, to receive 5 or 3 intradermal immunisations monthly, respectively; each arm was divided in two treatment groups receiving 7.5 or 30 µg of Tat, respectively. The study includes a 3 weeks screening period, a 16 or 8 weeks study treatment period, a 40 or 32 weeks post-immunisation follow-up period for the 3 or 5 immunisation schedules, respectively.

The ISS OBS T-002 (ClinicalTrials.gov n. NCT01024556) was designed as an observational study, to be conducted in parallel with the T-002 clinical trial in the same clinical centres, on HIV-1 infected HAART-treated adult subjects of either gender, ≥18 years of age, under successful HAART (chronic suppression of HIV infection with a plasma viraemia <50 copies/mL in the last 6 months) and a known $CD4^+$ T cell number at entry and nadir level of $CD4^+$ T cells. From the 116 subjects enrolled to date in the OBS T-002, which includes both anti-Tat antibody positive and negative patients at study entry, 88 individuals where anti-Tat antibody negative. This represents a reference group for all the evaluations performed in the T-002 trial.

Study Agent

Production and batch release of the Tat vaccine were performed by Diatheva-AVITECH, Fano (PU), Italy and Injectalia srl Pomezia (RM), Italy, respectively, according to Good Manufacturing Practices (GMP) and national and international legal requirements. The active substance of the Tat vaccine is the biologically active recombinant Tat protein (HTLV-III. strain, clone BH-10), produced in *E. coli* and purified by DEAE and Heparin Sepharose chromatography, as previously described (100, 111-115). The Tat vaccine was formulated in a suitable saline buffer, in the presence of 1% saccharose and 1% human serum albumin, and filled in 7.5 mL or 30 µg/0.5 mL vials, as previously described (100, 111-115).

Clinical and Laboratory Platforms

All clinical and laboratory activities, as well as psychosocial and behavioural assessments, were harmonised among the clinical centres according to Good Clinical Practice (GCP) procedures and by establishing standardised and integrated platforms (100, 111, 113-115). The immunological and virological testing was performed by the Core Laboratory for Immunology and Virology at the San Gallicano Hospital in Rome as a Joint Unit with ISS and validated upon international standard of quality (ISO 9000) (100).

Boards Supporting the T-002 Trial

The study has been supported by different independent boards: the Community Advisory Board (CAB) comprising the most representative Italian non-governmental organisations (NGOs) involved in all issues relating to HIV/AIDS; the Data Safety Monitoring Board (DSMB), constituted by experts in the fields of medicine and biomedical science for the specific field, the International Advisory Board (IAB), an independent committee of international experts in the virological/immunological field of AIDS and vaccine, with the aim of giving suggestions and advice on critical aspects of the trial (100, 111, 113-115).

Measurement of Serum Antibodies Against the Tat Protein

Anti-Tat antibodies were assessed by ELISA as previously described (91, 106, 113-115). Serum samples obtained at the indicated time points were diluted at 1:100 (for IgG) or at 1:25 (IgM and IgA). Titres were determined as the reciprocal of the sample dilution with absorbance values higher than cut-off value.

Assessment of IFN-γ, IL-2 and IL-4 Antigen-Specific Production by PBMC with the EliSpot Assay The EliSpot assay was performed as previously described (113-115), using commercial plates and kits for the determination of γ-IFN, IL-2 and IL-4 (all from R&D Systems, EL285, EL202, EL204, respectively), in response to Tat, Env or recall antigens. Briefly, $2.5 \times 10^5$ PBMC were plated in each well in RPMI 1640 containing 10% FBS in the presence of 4 distinct pools of Tat peptides [15-mers overlapping by 10 amino acids and spanning the entire Tat sequence (aa 1-102), 5 µg/mL each] (UFP Service, University of Ferrara, Italy), 2 distinct pools of Env peptides [15-mers overlapping by 10 amino acids and spanning the entire sequence, 5 µg/mL each] (Neosystem), *Candida* (5 µg/mL) (Nanogen Advanced Diagnostics), or a CEF peptide pool (2 µg/mL each) (Anaspec, 01036-05). Phytohemoagglutinin (PHA) at 2 µg/mL (OXOID S.p.A.) or medium alone were the positive and negative controls, respectively. After incubation at 37° C. in a humidified 5% $CO_2$ chamber (24 hrs for IFN-γ and 48 hrs for IL-2 and IL-4, respectively), plates were incubated at 4° C. overnight in the presence of the detection Ab. After a combined treatment with Streptavidin-AP and BCIP/NBT Chromogen and drying, positive cells were determined by an EliSpot Reader (AID ELISPOT Reader System). The tests were considered valid only when the positive controls (PHA) showed a number of SFC/well ≥100. IFN-γ EliSpot was considered positive only when the number of $SFC/10^6$ cells was ≥30, and fold increase over control was ≥3. The IL-2 and IL-4 EliSpot were considered positive only when fold increase was ≥3 (113-115).

Assessment of Antigen-Specific T-Cell Proliferation

The proliferative response to Tat protein (1-5 µg/mL) or peptides (2 µg/mL), HIV Env protein (5 µg/mL) (Fitzgerald), *Candida* (5 µg/mL) (Nanogen Advanced Diagnostics), or CEF peptide pool (2 µg/mL each) (Anaspec, 01036-05), was assessed by the CellTrace CFSE Cell Proliferation kit (Molecular probes™, Invitrogen) following the manufacturer's instructions. Briefly, Ficoll-purified PBMC ($3 \times 10^5$/ well) were stained with carboxyfluorescein diacetate, succinimidyl ester (CFSE) and incubated at 37° C. for 10 min in PBS [w/o $Ca^{2+}$ supplemented with 0.1% Foetal Bovine Serum (FBS)]. The staining was then quenched by the addition of 5 volumes of ice-cold culture media (5 min on ice) and cells were pelleted by centrifugation for 3 min at 1,500 rpm. After washing, CFSE-labelled cells were seeded in 96-well round-bottomed plates at $3.5 \times 10^5$ cells/100 µL/well and cultured for 6 days with the different antigens in 10% FBS. Cells were then washed with BD CellWash (BD Biosciences, San Jose, Calif. USA). After the addition of 100 µL EDTA 5 mM (Sigma-Aldrich, St. Louis, Mo. USA), cells were washed twice (BD CellWash) and incubated at 4° C. for 20 min with the following monoclonal antibodies: CD4, CD8, CD25, conjugated with APC-Cy7, PE-Cy7 and APC, respectively (BD Biosciences). After final washing, cells were processed by flow cytometry (FACSCanto, BD). The results were elaborated by the ModFit software (Verity Software House, INC.), subtracted of the background values, and then expressed as Proliferation Index (PI). Fold increase (FI) are calculated as the ratio of PI in the presence of the specific antigens versus the PI values of control samples. Proliferative responses were considered positive when FI was ≥2.

Assessment of Lymphocyte Cell Subsets in Peripheral Blood

PBMC phenotype was determined by using BD Multitest 6-color TBNK reagent with BD Trucount tubes (BD Biosciences). BD Multitest 6-color TBNK reagent contains FITC-labelled CD3, PE-labelled CD16 and CD56, PerCP-Cy5.5-labeled CD45, PE-Cy7-labelled CD4, APC-labelled CD19 and APC-Cy7-labelled CD8, respectively. Samples were processed by a FACSCanto flow cytometer (BD Biosciences) and data collected and analysed by the FACSCanto clinical software, which automatically compensates for all six fluorescences and creates all the necessary gates to assess both the percentages and the absolute numbers of T-helper cells ($CD3^+CD4^+$), T-cytotoxic cells ($CD3^+CD8^+$), B-cells ($CD19^+$) and NK cells ($CD16^+CD56^+CD3^-$), respectively.

Assessment of T Cell Activation Markers and Regulatory T Lymphocytes (T-Regs)

Fresh whole blood was stabilised at a 5:1 ratio with TransFix (Cytomark) for 2-7 days and used for determination of T cell surface activation marker expression with anti-CD8 FITC/CD38 PE/CD3 PerCP/HLA-DR APC (MultiTEST™ BD Biosciences) plus anti-CD4 APC-Cy7 monoclonal antibodies (BD Pharmingen), respectively. Fifty µL of TransFix-preserved blood were incubated with the antibody cocktail for 30 min in the dark. Red blood cells were lysed using a 1:10 BD FACS Lysing Solution (BD Biosciences). Cells were then washed twice and resuspended in 600 µL of FACS CellWash (BD Biosciences). Samples were then processed by a FACSCanto flow cytometer (BD Biosciences), and data collected and analysed using the FacsDiva software (BD Biosciences). Collective quadrant gates, based on HLA-DR and CD38 expression on CD4⁺ or CD8⁺ T cells, were established for gating HLA-DR⁺ and CD38⁺ cell populations, respectively.

For determination of CD25 expression and the identification of T-regs, PBMC were stained with the anti-human monoclonal antibodies APC-Cy7-labeled CD4, APC-labelled CD25 (BD Biosciences) and PE-labelled FOXP3 (eBioscience, San Diego, Calif.), respectively. Briefly, after surface staining with CD4 and CD25 monoclonal antibodies, cells were washed, fixed, permeabilised and stained with FOXP3 monoclonal antibody using the cell permeabilisation kit (eBioscience), according to the manufacturer's instructions. Cells were then acquired using a FACSCanto flow cytometer (BD Biosciences), and data collected and analysed using the FacsDiva software (BD Biosciences). To determine CD25 expression on total T cells, gating was performed on CD4-positive and on CD4-negative cells, respectively. For T-regs identification, gating was performed on CD4 T cells to examine CD25/FOXP3 doubly-positive cells, and then on CD4/CD25 to assess FOXP3 positive lymphocytes.

Measurement of Neopterin, β2-Microglobulin and Total Immunoglobulins

Determination of neopterin in serum samples was performed by a competitive Enzyme Immune Assay (EIA) using coated microtitre plates (BRAHMS, Berlin, Germany), as previously described (132). β2-microglobulin in plasma was measured by the immuno turbidometry method, using commercially available kit and a Cobas 6000 analyser (Roche-Hitachi Diagnostic). Measurements of total plasma IgM, IgG and IgA were performed as described previously (133) by kinetic nephelometry (IMMAGE® Immunochemistry System, Beckman Coulter Inc.), according to the manufacturer's instructions.

Assessment of PBMC Viability by Trypan Blue Dye Staining

In vitro cell viability was determined by Trypan Blue Dye Exclusion Method using the Vi-CELL™ XR Counter (Beckman Coulter), which allows measurement of both cell number and percentage of viable cells (134-136). PBMC were diluted 1:10 in DMEM 10% FCS and loaded on Vi-CELL™ XR Counter in duplicate. When the cell number was less than 50,000 µL, the counting procedure was repeated using a 1:5 dilution. The mean value of duplicate samples was considered for the determination of cell viability.

Assessment of Central Versus Effector Memory and Naive CD4 or CD8 T Cells in Peripheral Blood To identify central memory (CD45RA−/CD62L+), effector memory (CD45RA+/CD62L, and CD45RA−/CD62L−), and naive (CD45RA+/CD62L+) CD4 and CD8 T cells, PBMC were stained with a panel of directly conjugated monoclonal antibodies specific for the following T cell markers: CD3 (PerCP), CD4 (APC-Cy7), CD8 (APC), CD45RA (FITC), CD62L (PE). All the antibodies were obtained from BD Biosciences (MultiTEST™ BD Biosciences). Samples were processed by a FACSCanto flow cytometer (BD Biosciences) and data collected and analyzed by the FlowJo (Tree Star, Inc., Ashland, Oreg.) software.

The different T cell subsets were identified by hierarchical gating first on the lymphocyte population (morphological gating), then on CD3+ T cells, and subsequently on CD4+ or CD8+ T cells. Finally, collective quadrant gates based on CD45RA and CD62L expression on CD3+/CD4⁺ or CD3+/CD8⁺ T cell populations were established to identify the different CD45RA and CD62L subsets.

Determination of HIV-1 Viral Load in Plasma

HIV-1 RNA quantitation was performed by using the Amplicor HIV-1 Monitor Test, version 1.5, according to the manufacture's instructions (Roche Diagnostics SpA, cod. 21117750123) and by using an UltraSensitive procedure in which HIV-1 viral particles in plasma are concentrated by high speed centrifugation, followed by lysis of the particles and precipitation of the HIV-1 RNA. The UltraSensitive procedure gives a linear response from 50 to 100,000 HIV-1 RNA copies/mL (134-137). Results were concordant with those from the COBAS AmpliPrep/COBAS TaqMan HIV-1 Test, version 2.0, following the manufacture's instructions (Roche Diagnostics SpA, cod. 05212294 190 CAP-G/CTM HIV-1 v2.0), which gives a linear response from 20 to 10,000,000 HIV-1 RNA copies/mL.

Proviral DNA Assessment

Total HIV DNA as well as integrated and 2-LTR episomal DNA were determined in PBMC as previously described (37, 138-140).

Total RNA was extracted from 250 µL of plasma (QIAamp Viral RNA mini kit, Quiagen) and proviral DNA was extracted from 1×10⁶ PBMC (QIAamp DNA mini kit, Quiagen). Reverse transcription of the RNA sample (One step RT-PCR kit) was followed by a nested polymerase chain reaction (PCR) using primers targeting the first and second exon of the Tat gene. For proviral DNA, the sample was directly amplified by nested PCR using the same primers. Sequencing of the Tat gene was then performed by an automated 3100 Genetic Analyzer (Applied Biosystems Inc., Foster City, Calif.) with M13 Sequencing Primers and Big-Dye terminator cycle sequencing kit, as previously described (91). The predicted Tat protein sequence was then compared with that from HIV-1 clade B prototypic isolates BH-10 and HXB2.

Sequence Analysis

The mean values of divergence (genetic distances between time 0 and visit 16-23) within and among groups were estimated by the "bootstrap method" with 500 replicates using MEGA Program, version 3.1 (Poisson model with gamma of 2). The distance of the Tat sequences from vaccinees and placebo with respect to the BH10 and HXB2 prototypic sequences was elaborated according to the evolution model of Eigen (141).

Measurement of Serum Antibodies Against *Toxoplasma*

The presence of antibodies against *Toxoplasma* were assessed by Fluorescent Enzyme Immunometric System using the RAD *Toxoplasma* IgG or IgM kit (Codes RD056 and RD057, respectively by Radim SpA).

In particular, assay range for IgM detection is 0-700 IU/mL with a cut-off of 75-100 IU/mL; while for IgG the assay range is 0-265 IU/mL with a cut-off of 4-6 IU/mL.

In Vitro Neutralization of the Tat and Env Complex by Human Sera

Sera from HIV infected individuals diluted in PBS buffer (1:30), containing anti-Env binding antibodies (Abs) (titer range 3,200-25,600, as assessed on HIV-IIIB gp120) and negative or positive for anti-Tat binding Abs were added to the mixture containing trimeric ΔV2 Env (0.4 µM) and equimolar Tat protein (prepared as described above) or to trimeric ΔV2 Env alone for 1 hour at 37° C., and added to monocytes-derived dendritic cells (MDDC) to a 1:5 final dilution for 10 min.

MDDC were obtained by culturing monocytes for healthy donors for 6 days in medium containing GM-CSF (500 U/mL; R&D Systems, Minneapolis, USA) and IL-4 (1,000 U/mL; R&D Systems) (93). DC maturation was induced by LPS (1 µg/mL) (Sigma-Aldrich, Milano, Italy). MDDC phenotype was assessed by detection of specific surface markers (CD1a, CD 14, CD40, HLA-DR, CD83 and CD86) as described (93).

Since Tat activity is rapidly lost upon oxidation, the protein was resuspended, handled and tested for biological activity, as described previously (93). The protein samples were then added to MDDC ($2\times10^5$ cells/mL) to a 1:100 final dilution. Cells were then washed with cold medium and treated for 5 min at 37° C. with trypsin-EDTA (Life Technologies, Paisley, UK) to remove cell-surface bound protein. After fixation and permeabilization (Perm Solution, BD Biosciences), MDDC were stained with affinity-purified rabbit polyclonal anti-Tat IgG Ab (Diatheva, Fano, Italy) or rabbit IgG control Ab (ICN Biomedicals, Opera, Italy), followed by FITC-conjugated anti-rabbit Ig (Pierce, Rockford, Ill.). Fluorescence was analyzed by flow cytometry, and results were expressed as the percentage of positive cells as compared to isotype stained samples. The values from non-permeabilized cells were subtracted. In blocking experiments, prior to the addition of the proteins, MDDC were cultured at 4° C. for 2 h in the presence of mAbs directed against the $\alpha5\beta1$, $\alpha v1\beta3$ and $\alpha v\beta5$ integrins (10 μg/mL each) (Chemicon International, Temecula, Calif.), or control isotype (mouse IgG1, BD Biosciences).

Monomeric and trimeric wild-type or ΔV2-Env molecules from clade B SF162 HIV have been described elsewhere (142, 143). For Env uptake experiments, a fixed concentration of each Env molecule (3.52 μM in protein subunit) was incubated at 25° C. in degassed phosphate buffered saline alone or in the presence of increasing concentrations (0.2-48.6 μM) of biologically active Tat for 10 min. The protein samples were then added to MDDC ($2\times10^5$ cells/mL) to a 1:100 final dilution. Cells were then washed with cold medium and treated as described above for Tat uptake experiments, and stained with anti-gp120 (NeoMPS Strasbourg, France) or rabbit IgG control Ab (ICN Biomedicals, Opera, Italy), followed by FITC-conjugated anti-rabbit Ig (Pierce, Rockford, Ill.). For integrin blocking experiments, mAbs directed against the $\alpha5\beta1$, $\alpha v1\beta3$ and $\alpha v\beta5$ integrins were used as described above. Cells were then stained for intracellular Env.

Statistical Methods

Cochran-Armitage Trend test was used to compare frequencies of humoral responses. McNemar's test was used to compare pre-post immunization frequencies of cellular responses within treatment groups. Wilcoxon signed-rank test was applied to evaluate increase of cellular responses intensity. Student's t-test for paired data was used to assess the mean changes from baseline of activation markers, lymphocytic phenotypes and cell viability, after controlling normality assumption of variables distribution (Saphiro-wilk test). Multivariate regression model for repeated measures was applied on $CD38^+/CD8^+$ T cells (%) to all immunized subjects, to assess the potential relationships with the anti-Tat antibody titres (IgM, IgG, IgA), $CD8^+$ central memory (%) and anti-Tat induced cytokines (γIFN, IL-2 and IL-4).

All statistical tests were carried out at a two-sided 5% significance level. Analyses and data processing were performed using SAS® software (SAS Institute, Cary, N.C., USA).

Results

Therapeutic Immunisation with the Native HIV-1 Tat Protein Induces Specific Humoral and Cellular Immune Responses in HAART-Treated Individuals Therapeutic immunisation with Tat was safe, confirming data of phase I studies (79, 89-93), and induced both humoral and cellular immune responses with both Tat dosages (FIG. 1). In particular, the 30 μg dose was more potent at inducing total anti-Tat antibodies (anti-Tat Ab) and at generating Ab of the IgM, IgG and IgA subclasses (p=0.0267, p=0.0093 and p=0.0001, respectively) (FIG. 1A). This Tat dose was also the most effective at inducing a durable Ab response (p=0.0014), which was still present at approximately one year post-immunization (48 weeks), for both IgM and IgG subclasses (p=0.0057 and p=0.0045, respectively) (FIG. 1B). In contrast, peak Ab titres did not significantly differ between doses and only slightly decreased at 48 weeks (FIG. 1 C, D).

Figure 2:
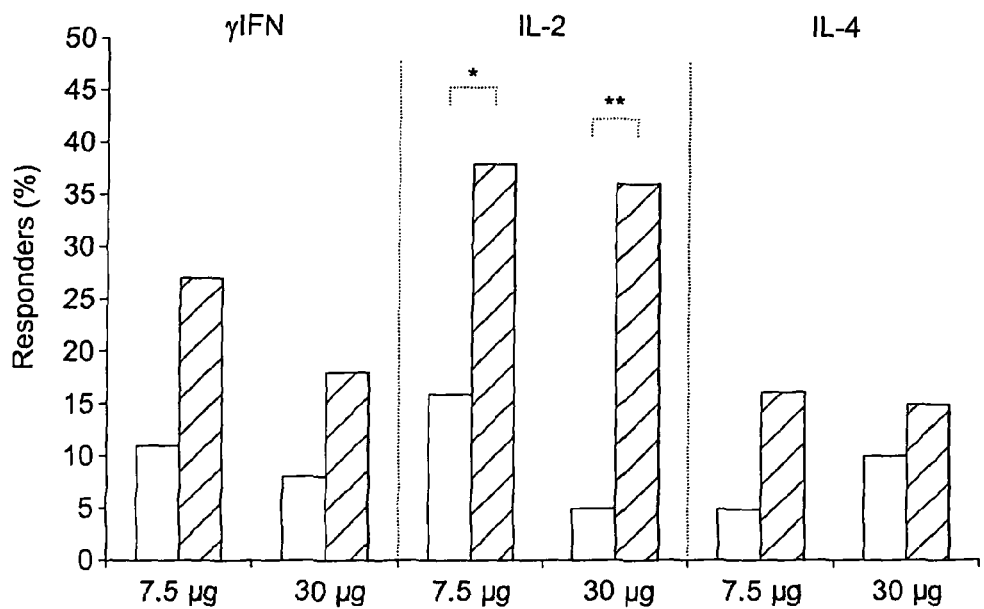
FIG. 2 shows anti-Tat cellular immune responses after Tat immunization.
Figure 2:
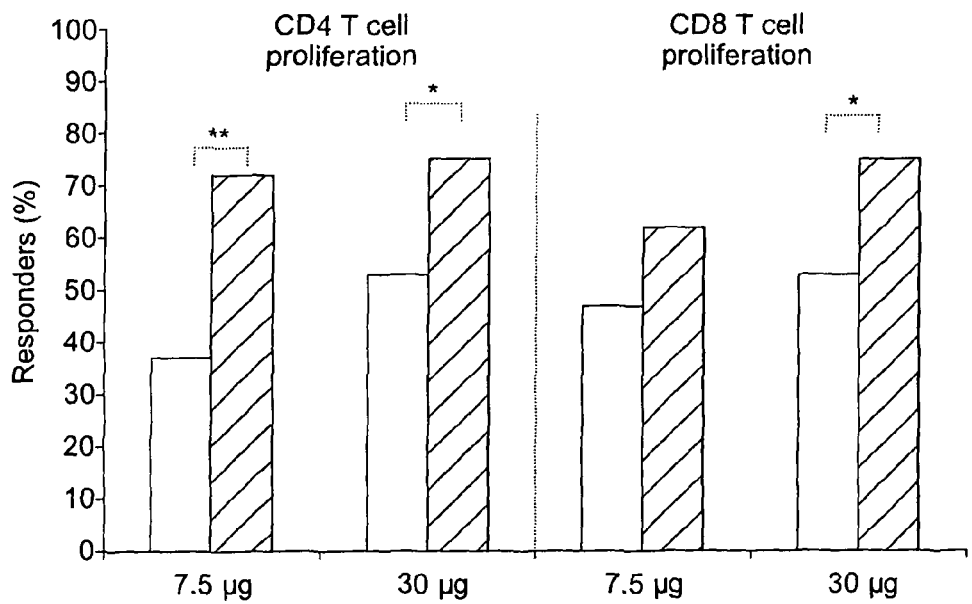

Both Tat doses induced specific cellular responses (FIG. 2 A-B and Table 3). A cumulative analysis of the T cell responses (up to 48 weeks after immunization) indicated an increase in the percentage of responders for production of IL-2 (p=0.0325 and p=0.0013 at Tat 7.5 or 30 μg, respectively) and, to a lesser extent, IFN-γ and IL-4, as well as of Tat-specific $CD4^+$ (p=0.0045 at Tat 7.5 μg, p=0.0325 at Tat 30 μg) and $CD8^+$ T cell proliferation (v0.0325 at Tat 30 μg). No relevant differences were observed between 3 or 5 immunizations.

The assessment of the cellular immune responses to Tat in the OBS subjects revealed an increase of the percentage of responders in terms of both specific cytokines production, except for IL-2 production, and particularly of $CD8^+$ T cell proliferation. An increase in the peak values of cytokine production and T cell proliferation was also detected in OBS (Table 4 and 10).

Immunisation with Tat Downregulates Phenotypic and Biochemical Markers of Immune Activation and Increases Regulatory T-Cell (T-Regs) Markers To investigate further the effect of therapeutic immunisation with Tat, key parameters of AIDS pathogenesis and progression used to evaluate HAART efficacy were monitored. These included cellular (CD25, CD38, HLA-DR) and biochemical (serum β2-microglobulin, neopterin and total immunoglobulins) immune activation markers, as well as the percentage and the number of T-regs, which are known to exert a suppressive effect on immune activation (72, 73). Baseline values of these parameters were determined at study entry in subjects of both the trial and the OBS studies. No relevant differences at baseline were seen between the two Tat dosage groups of the trial, except for a few immunological markers between trial and OBS subjects (Table 5 and 6).

Since no differences were detected between the number of immunisations (3 or 5) with the same Tat dose (7.5 or 30 μg) the evaluation of immunological parameters was performed by stratifying results by Tat dosage. Results from trial subjects are shown up to 84 weeks versus baseline (week 0).

CD38 and HLA-DR Expression on $CD4^+$ and $CD8^+$ T Cells

Figure 4:
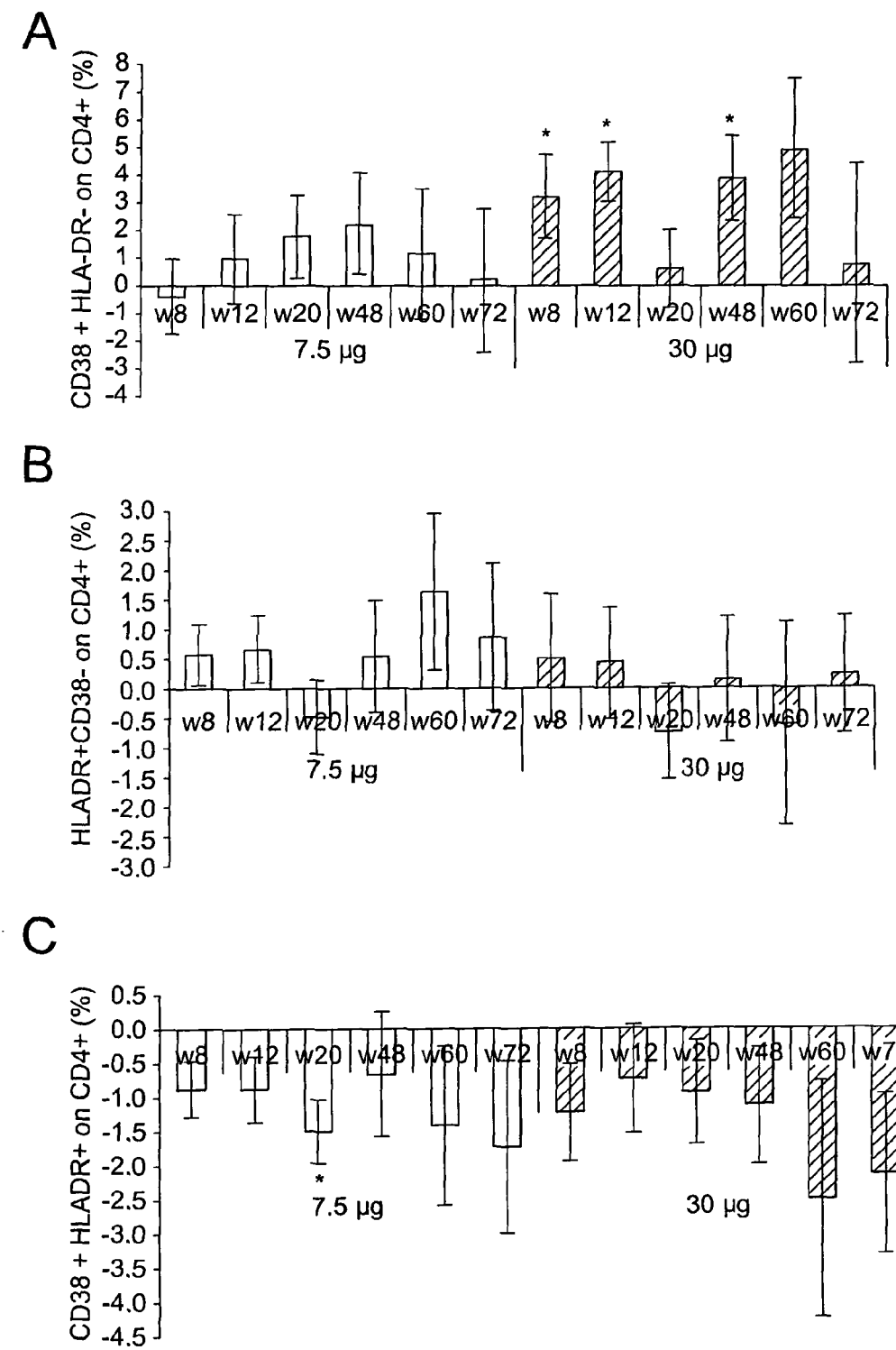
FIG. 4 shows the expression of activation markers on $CD4^+$ T cells after Tat immunization.

A down-regulation of CD38 expression, a key cellular marker of persistent immune activation, was observed on peripheral $CD8^+$ T cells from immunised subjects until week 72 and reached statistical significance at both Tat doses (FIG. 4 A).

Of note, longitudinal analysis of CD38 expression on $CD8^+$ T cells showed a significant correlation in its down-regulation with increasing anti-Tat IgA titres at the 30 μg Tat dose [$\log_{10}$ IgA: β=−5.8% (95% CI −11.1%; −0.5%) p=0.0332].

Figure 3:
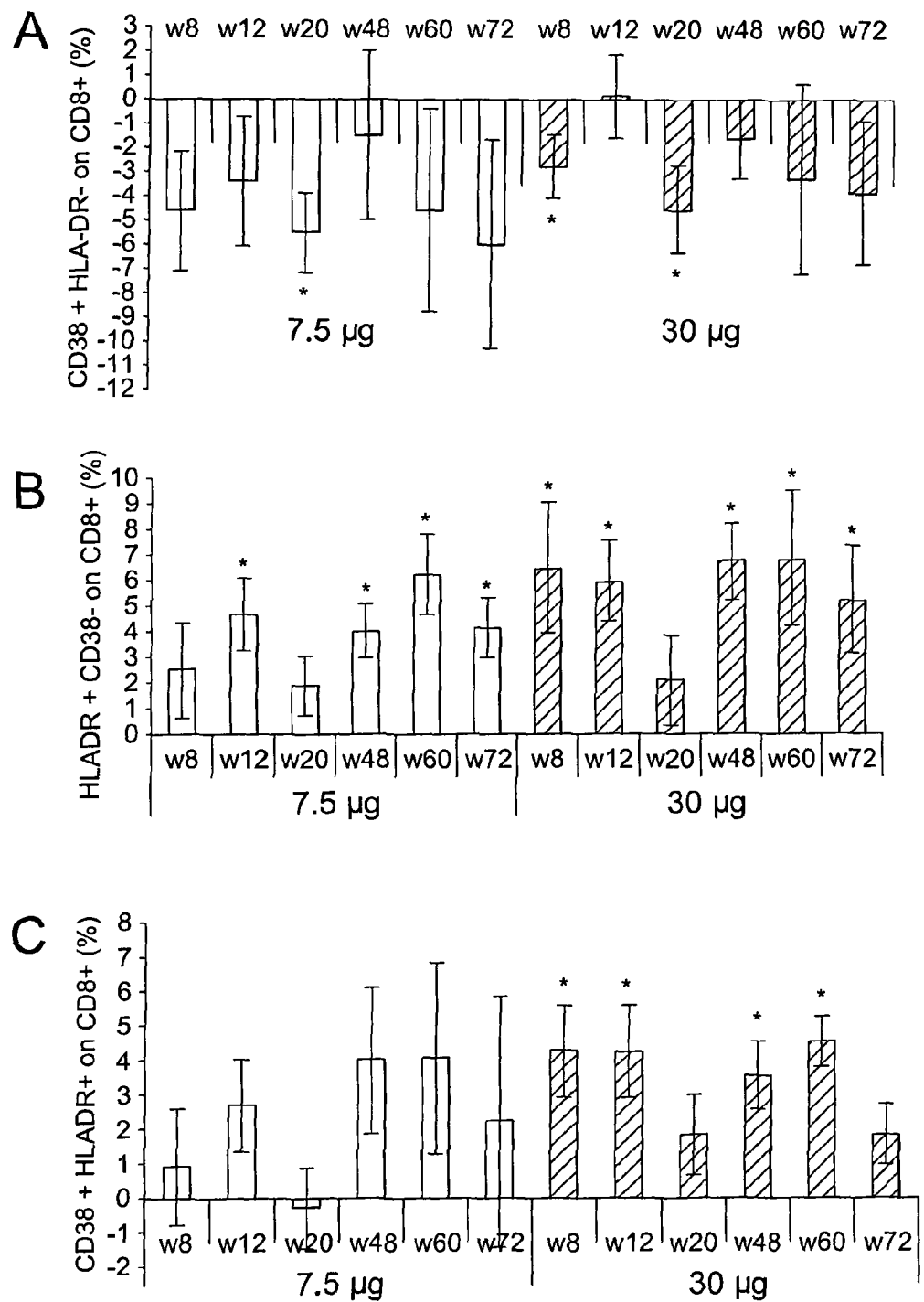
FIG. 3 shows the expression of activation markers on $CD8^+$ T cells after Tat immunization.

A significant increase of HLA-DR expression on $CD8^+$ T cells, either alone or in combination with CD38, was also measured at both Tat doses (FIG. 3, B-C). The average frequency of $CD38^+/HLA-DR^+$ doubly-positive $CD8^+$ T lymphocytes, which have been associated with potent antiviral activity (119, 120), remained significantly higher throughout the entire follow-up (FIG. 3 C). A decrease of CD38 expression on CD8+ T cells was observed during the follow-up in the OBS subjects (Table 10), in contrast, a decrease in the frequencies of singly-positive HLA-DR or doubly-positive CD38+/HLA-DR+ CD8+ T cells was observed in these subjects.

The modulation of the expression of the above markers was somewhat opposite on CD4+ T cells (FIG. 4, A-C). In particular, the percentage of CD38 singly-positive CD4+ T cells was significantly increased in immunised subjects, whereas a decrease was observed in OBS subjects (Table 10). Little changes in HLA-DR expression on CD4+ T cells were induced by immunisation, while its expression was significantly reduced in OBS individuals. Lastly, the frequencies of CD38+/HLA-DR+ doubly-positive CD4+ T lymphocytes in immunised subjects were reduced at all time points and at both Tat doses, a difference that reached statistical significance only at the 7.5 μg dose at week 20, while a small reduction was seen in OBS subjects (Table 10).

Overall, in immunised subjects the expression of HLA-DR and CD38 on both CD4+ and CD8+ T cell subsets was highly different than that recorded during the same time period in the OBS subjects; in particular, opposite changes in respect to baseline values were seen in most cases (FIGS. 3 and 4, Table 10).

Biochemical Markers of Immune Activation

Figure 5:
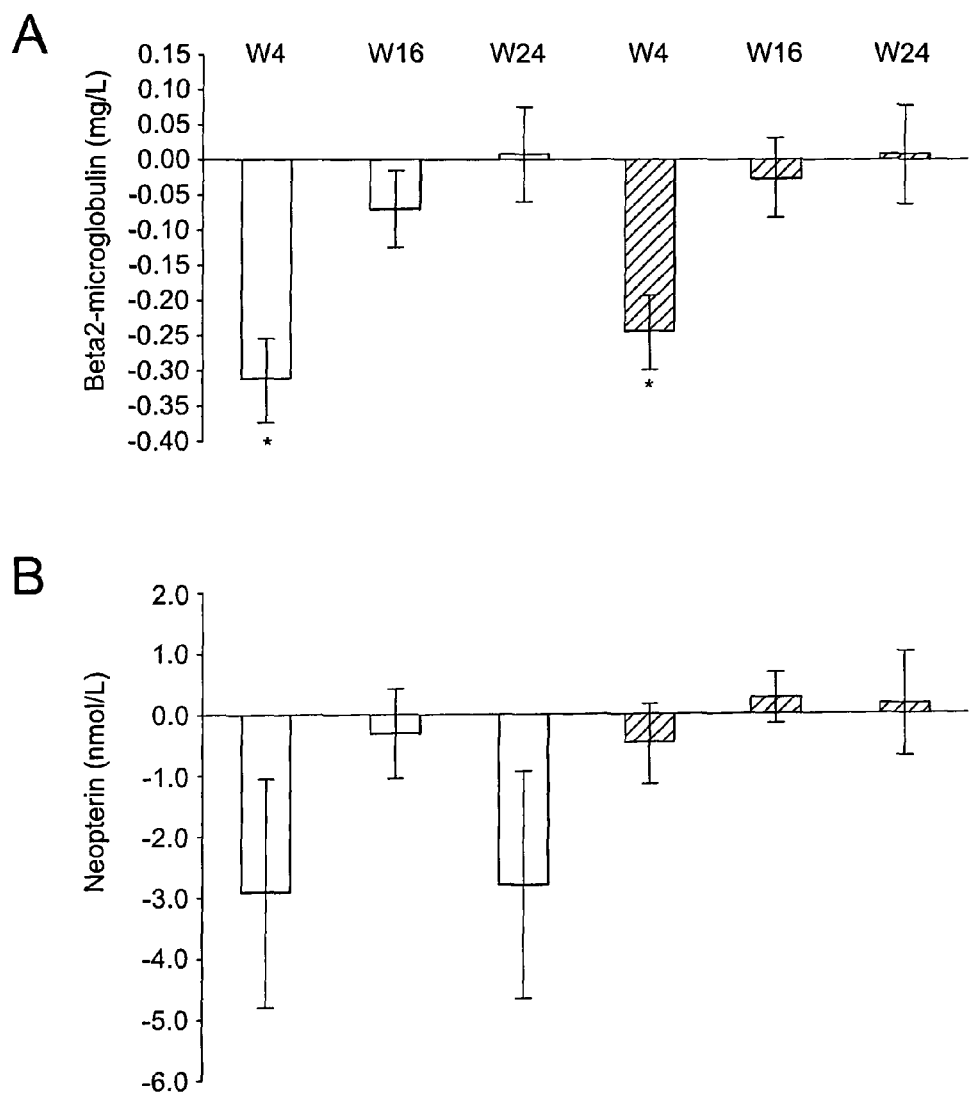
FIG. 5 shows the production of β2-microglobulin and neopterin after Tat immunization.
Figure 6:
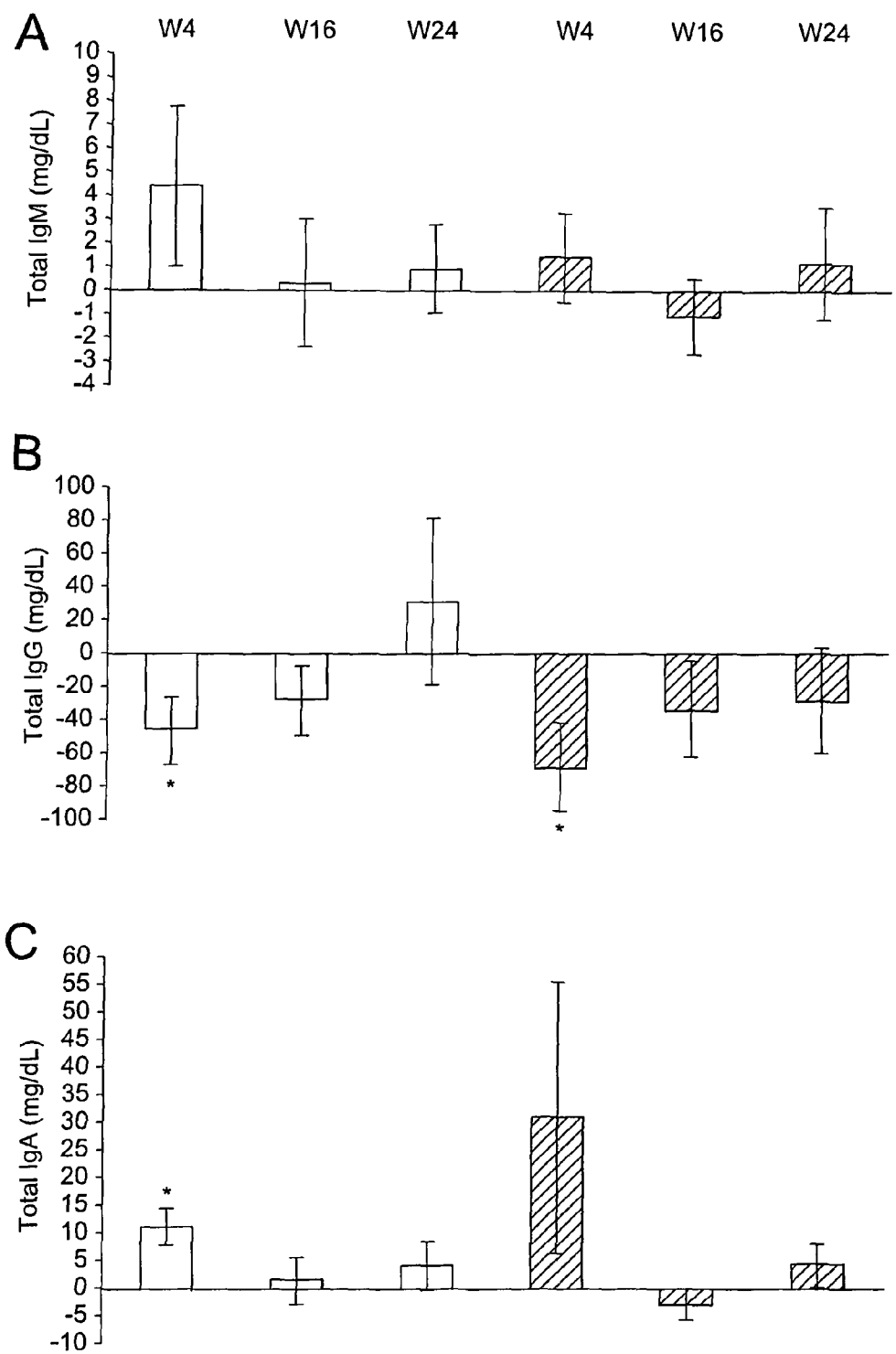
FIG. 6 shows the production of total Ig after Tat immunization.

The down-regulation of cellular markers of immune activation seen in immunised subjects was associated with a decrease in the serum levels of β2-microglobulin, neopterin and total immunoglobulins (Ig), which represent clinically relevant surrogate markers of systemic immune activation.

β2-microglobulin was reduced at both Tat doses at week 16 and 24, whereas in OBS subjects it increased at week 12 and decreased at week 24 as compared to baseline (FIG. 5 A and Table 10). Neopterin was more reduced in trial subjects as compared to OBS, but the reduction was small and did not reach statistical significance as compared to baseline values (FIG. 5 B and Table 10). Total Ig, and particularly IgG, were reduced in trial subjects and increased in OBS subjects as compared to baseline values (FIG. 6 and Table 10).

Of note, the reduction upon immunisation in the expression of phenotypic and biochemical immune activation markers was more evident in subjects with the highest values at baseline (Table 7). Conversely, the highest increase of T-regs was seen in individuals with the lowest values at baseline. For all these parameters, the changes observed upon immunisation were strongly significant and inversely correlated to baseline values (Table 7).

CD25 and FOXP3 Expression on CD4+ T Cells

Figure 7:
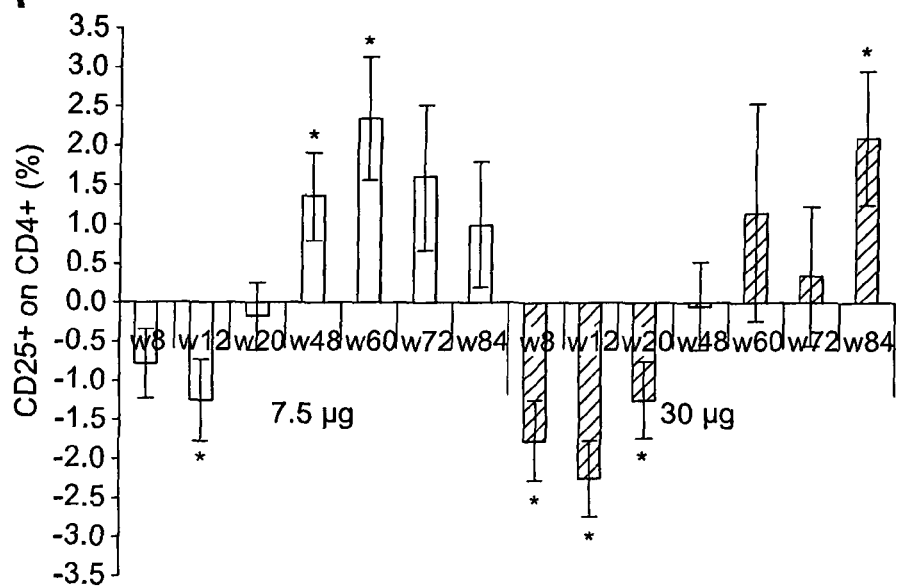
FIG. 7 shows CD25 and FOXP3 expression on $CD4^+$ T cells after Tat immunization.
Figure 7:
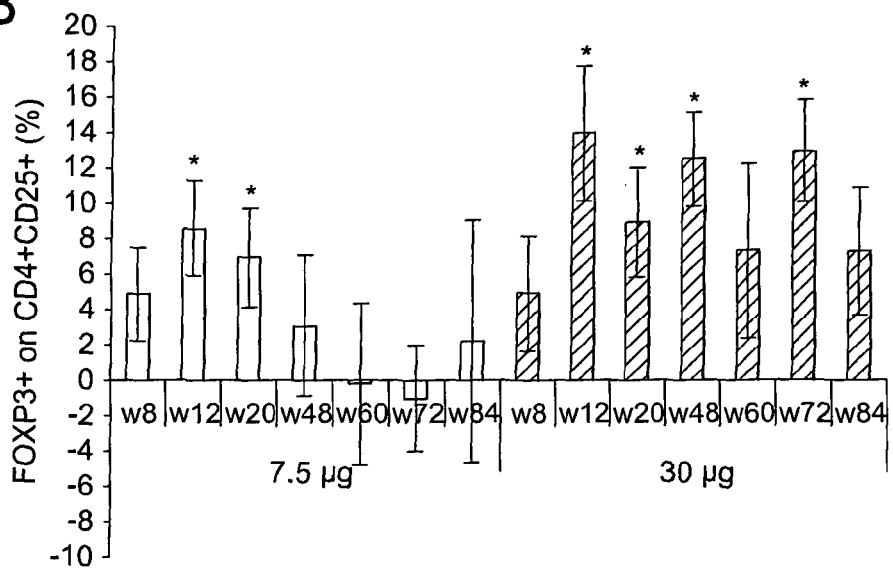
Figure 7:
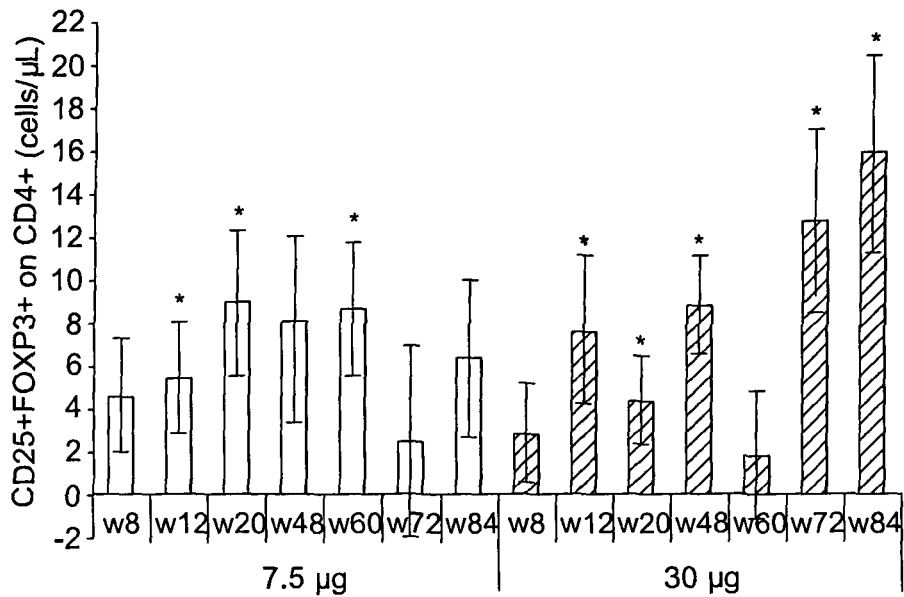
Figure 7:
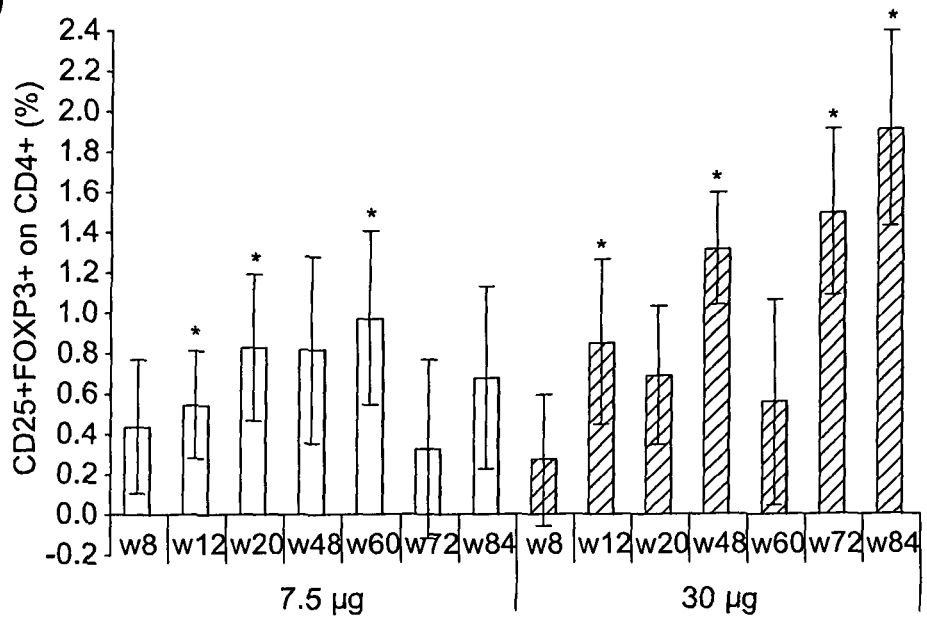

After Tat immunisation, the percentage of CD25+/CD4+ T cells markedly diminished as compared to baseline values until week 20 but increased significantly thereafter (FIG. 7 A). A significant increase in T-regs was observed (FIG. 7 B-D). In particular, the percentage of FOXP3 expression in the CD4+/CD25+ T cell subset as well as the percentage and absolute number of CD4+/CD25+/FOXP3+ T-regs had a significant and progressive increase at both Tat doses and up to week 84 (FIG. 7 B-D). In contrast, no relevant changes were observed in OBS subjects (Table 10).

Figure 8:
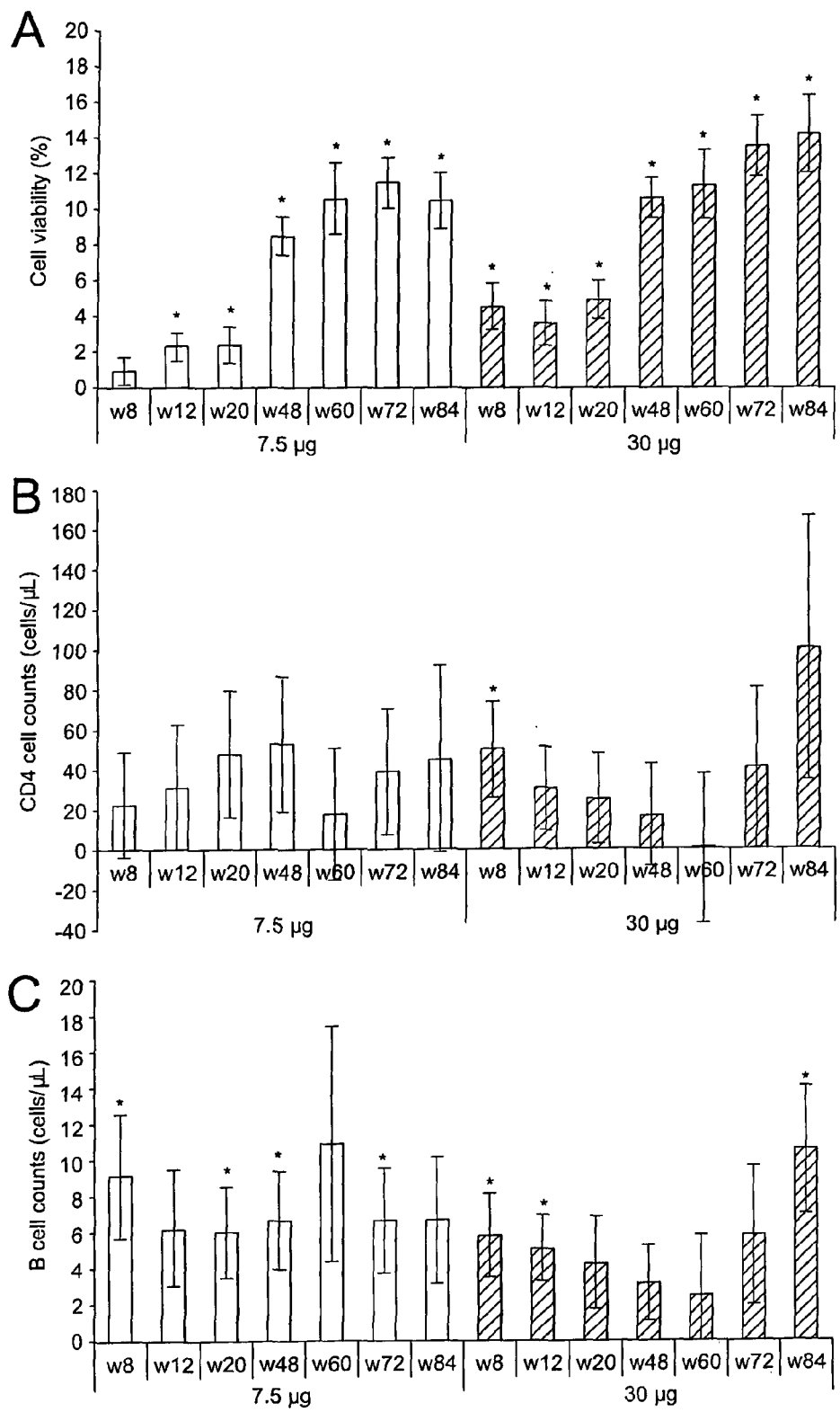
FIG. 8 shows the evaluation of PBMC viability, $CD4^+$ T cell and B cell counts after Tat immunization.

Immunisation with Tat Increases Peripheral Blood Mononuclear Cell (PBMC) Viability and the Number of CD4+ T Cells and B Cells PBMC viability in vitro is reduced by HIV infection (116-118). In contrast, significant increments of cell viability were seen in PBMC early after immunization with both Tat doses and particularly with 30 μg, which gave the most intense and persistent cell viability increase up to week 84 post-immunisation (FIG. 8 A). In contrast, cell viability increased at late time-points in OBS subjects. Of note, the increased cell viability was inversely related with its levels at baseline (r=−0.7, p<0.0001).

The CD4+ T cell number increased after Tat immunization, at all time-points and for both Tat doses (FIG. 8 B). Similarly, the B cell number also significantly increased upon immunisation with both Tat doses and at all time-points (FIG. 8 C). No relevant changes of the CD4+ T cell number were detected in OBS subjects, while a progressive loss of B cells was observed (Table 10).

Figure 9:
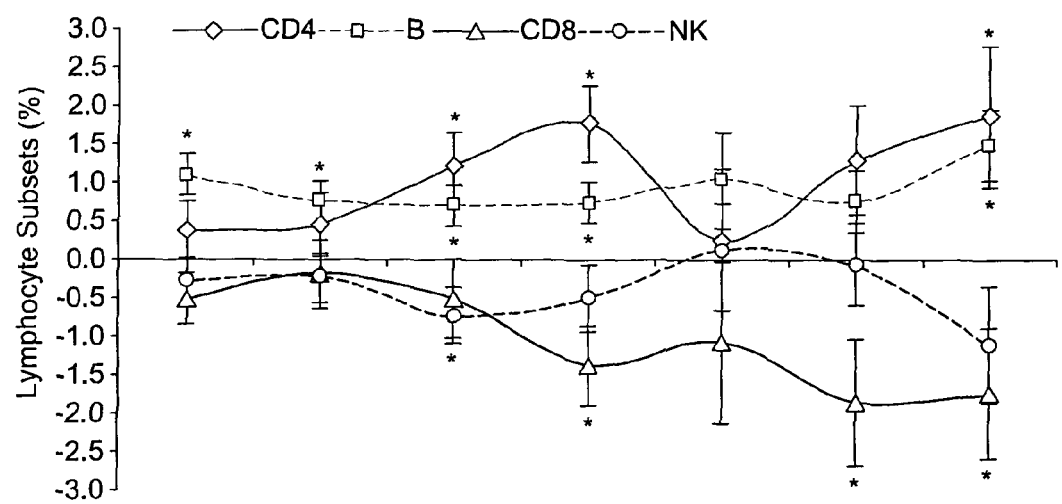
FIG. 9 shows the evaluation of the percentage of $CD4^+$, $CD8^+$, NK and B cells in all Tat-immunized subjects.

Immunization with Tat Increases the Percentage of CD4+ T Cells and B Cells and Reduces the Percentage of CD8+ and NK Cells Independently from the Type of HAART Regimen The determination of the percentage of lymphocyte subsets confirmed the increase of CD4+ T cells and B cells observed for the absolute values, showing significant increases of CD4+ T cells and B cells up to week 84 after the first immunization. In contrast, the percentage of NK and CD8+ T cells were significantly reduced (FIG. 9). As a consequence, the CD4/CD8 ratio progressively increased in immunized subjects. In the OBS subjects a moderate increase of the CD4+ T cell percentage and an overall stability or decrease of the B cell subset was detected (Table 10); a decreased of CD8+ T cells and a substantial stability of the NK subset was also observed.

Figure 10:
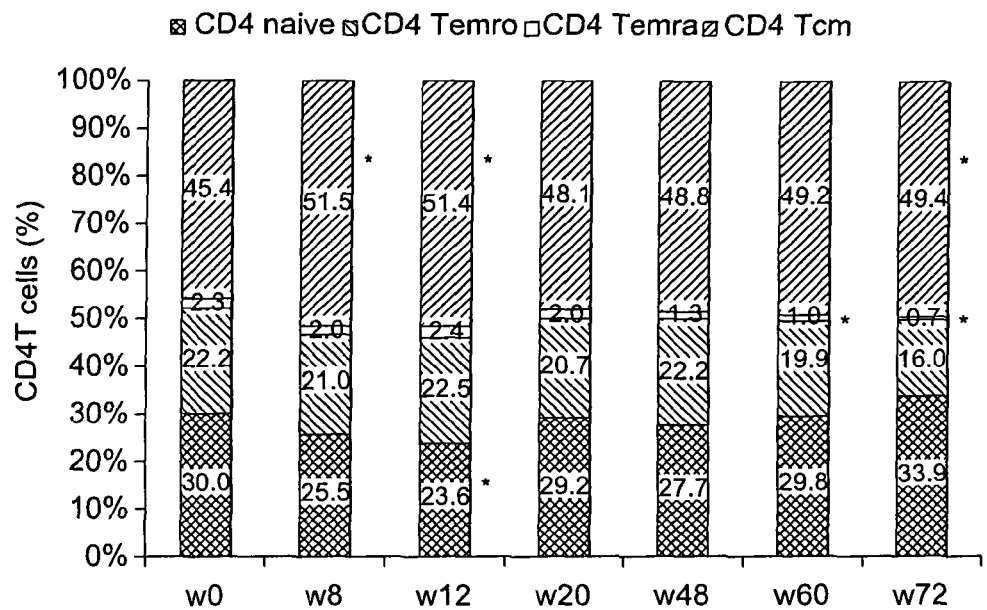
FIG. 10 shows the effect of Tat immunization on naïve, central and effector memory $CD4^+$ and $CD8^+$ T cells.
Figure 10:
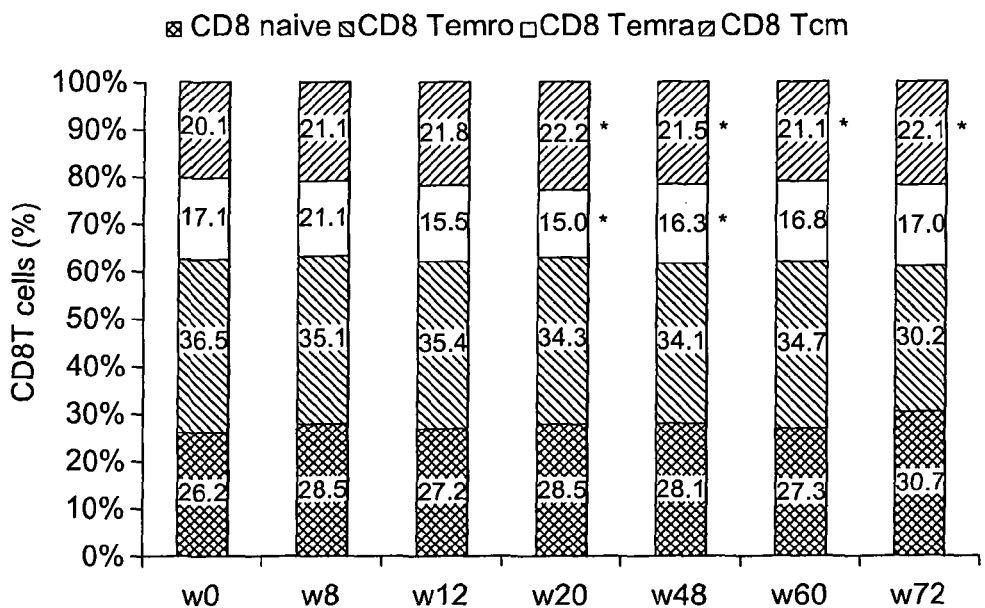

Immunization with Tat Increases Central Memory and Reduces Terminally-Differentiated Effector Memory CD4+ and CD8+ T Cells The percentage of central memory CD4+ and CD8+ T cells increased upon Tat immunization (FIG. 18). For CD4+ T cells, this finding was concomitant with a reduction of terminally-differentiated T cells (FIG. 10 A). For CD8+ T cells the earliest changes were observed for effector memory, in contrast, the increase in central memory was more evident at late time points (FIG. 10 B). In contrast a decrease in CD4+ and CD8+ central memory and an increase of effector memory was observed in OBS (Table 10).

This indicates, in contrast to CCR-5 inhibitors, that Tat immunisation counteracts the effects of HIV infection which leads to a loss of central memory T cells and to the increase of effector memory T cells (61). Since central memory T cells are localised in lymphoid tissues and are the central source for immune responses (62, 63), this suggests that therapeutic immunisation with Tat leads to a repopulation of lymphoid organs, thus reconstituting immune responses to antigens in the concept of immune homeostasis.

Figure 11:
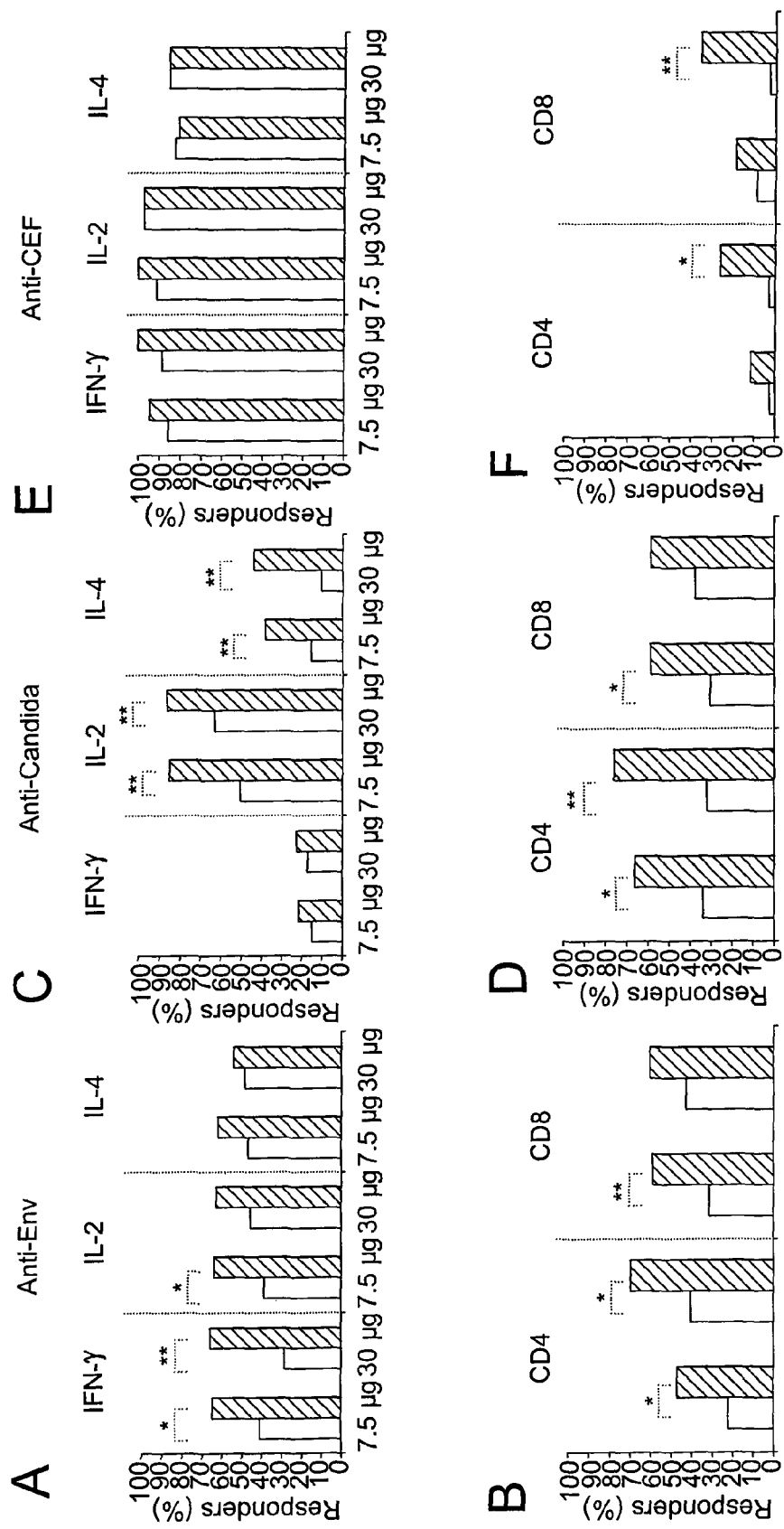
FIG. 11 shows cellular immune responses against Env or recall antigens after Tat immunization.

Immunisation with Tat Increases Cellular Responses to HIV Env and to Recall Antigens To verify whether the effects of therapeutic immunisation with Tat were accompanied by changes in key functions of adaptive immunity, T cell responses against HIV Env as well as against mycotic (*Candida*) and viral [Cytomegalovirus, Epstein Barr and influenza viruses (CEF)] recall antigens were determined by monitoring both Th1 and Th2 cytokine production and CD4+ and CD8+ T cell proliferation. An increase in both the percentage of responders and the intensity of the responses were found in subjects immunised with both Tat doses (FIG. 11). In particular, significant increases in the percentage of responders were found for IFN-γ and IL-2 responses against Env, and for IL-2 and IL-4 responses toward *Candida*, as well as for CD4+ and CD8+ T cell proliferation against both antigens (FIG. 11 A-D). Cytokine production by CEF was already present in most subjects with no difference after immunisation (FIG. 11 E).

In contrast, CD4+ and CD8+ T cell proliferation to CEF were very low at baseline and increased after immunisation particularly upon vaccination with 30 μg of Tat (FIG. 11 F). The intensity (peak values) of both cytokine production and proliferative responses to Env as well as to recall antigens including CEF were all significantly increased after immunisation as compared to baseline (Table 8).

In OBS subjects no changes were observed in cytokines production to Env, while the number of responders for CD4+ and CD8+ T cell proliferation against Env increased in the follow-up period (Table 10). The percentage of responders to *Candida* increased for IL-4 production as well as for CD4+ and CD8+ T cell proliferation. Increases in the percentage of responders to CEF were found for all cytokines, while no relevant changes were observed for lymphoproliferative responses. In addition, the intensity (peak values) of proliferative responses but not cytokine production to Env were increased, whereas for recall antigens both cytokine production and T cell proliferation were increased (Table 9). Overall, and in contrast to OBS subjects, in immunized subjects there was an increase of cytokine production to Env and *Candida* and of CD4+ and CD8+ T cell proliferation to CEF (FIG. 11 and table 10).

Correlations of Tat Immunization with Changes in T Cell Compartments

A multivariate regression analysis was used to assess the presence of potential correlations among the different parameters investigated after therapeutic immunization. A statistically significant inverse correlation was found between the percentage of CD38+/CD8+ T cells with anti-Tat IgA antibody titres (p=0.0309), CD8+ central memory T lymphocytes (p=0.0316), and with IL-2 production in response to Tat (p=0.0235), suggesting a direct relationship between the induction of anti-Tat specific IL-2 producing cells and increasing anti-Tat IgA titres with the expansion of CD8+ central memory T cells and the reduction of activated CD8+ effector T cells.

Proviral DNA, Virus Reservoir, HIV Elimination and Blocking of HIV Infection

Figure 12:
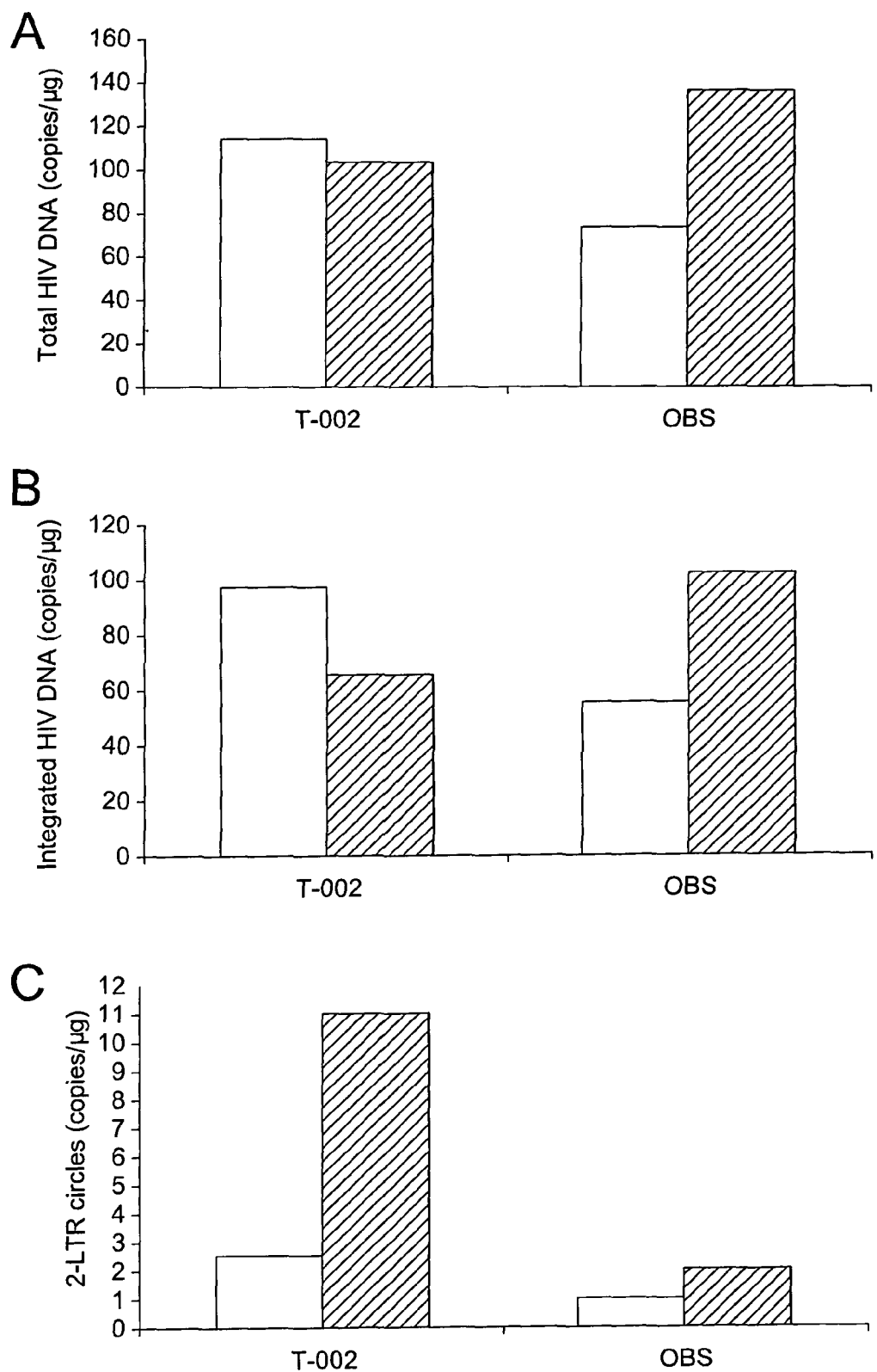
FIG. 12 shows proviral HIV DNA in subjects immunized with Tat and controls therefor.

Data up to 72 weeks on 4 subjects immunized with Tat showed a decrease of integrated HIV DNA and an increase of episomal 2-LTR DNA, while an increase of the integrated DNA and a stability of 2-LTR circles was observed in 3 patients of the OBS study (FIG. 12). These findings are comparable to what has been observed in Elite suppressor (39), and indicate that vaccination with Tat is reducing the virus reservoir, suggesting that Tat vaccination can eliminate the virus and substitute for or reduce the need of antiretroviral drugs. At the same time, data from asymptomatic HIV infected drug-naïve subjects vaccinated intradermally with Tat within the phase I trial indicate a reduction of total proviral DNA after vaccination, as compared with placebo (FIG. 13A) with a mild increase of plasma virus (FIG. 13B). This is associated with a reduced diversity of the tat nucleotide and amino acid sequence virus quasispecie as compared to placebo, both in the proviral DNA and in the plasma virus (FIG. 13C). Alltogether this strongly suggests that in vaccinees the virus reservoir (proviral DNA) is reducing and that the replicating virus is the archival virus first infecting the individuals, while in placebos virus diversity increases due to the expanding and escaping virus quasispecie. This suggested that no or little new infection occurs that is capable of maintaining a reservoir of more recent/current viruses. Indeed, the presence of anti-Tat antibodies in HIV-infected individuals blocks virus entry in dendritic cells and neutralizes the virus. This is indicated by the block of the entry of trimeric Env (as present on virus particle) into dendritic cells (typical cells necessary for establishment of virus infection which then become part of the virus reservoir) in the presence of the Tat protein with sera having both anti-Tat and anti-Env antibodies as compared to sera not having anti-Tat antibodies and for which the presence of Tat (that binds Env forming a new virus entry complex, which enters cells via integrin receptors, WO 2005/090391) further reduces neutralization increasing virus entry and escaping anti-Env antibodies (FIG. 14). Thus, the presence of anti-Tat antibodies in an HIV infected individual blocks infection of new target cells and the maintenance of the virus reservoir explaining the reduction of proviral DNA and the appearance of archival provirus even in the absence of HAART.

Toxoplasmosis

Results on vaccinees showed that, at baseline, 35% (37/107) had IgG antibodies anti-*Toxoplasma gondii* and that, of these, 22% (8/37) had IgG values greater than 150 IU/mL. In the OBS study, 28% of subjects had IgG anti-*T gondii* (9/32) at baseline and that, of these, 44% (4/9) had values greater than 150 IU/mL.

Antibody titres equal or above 150 IU/mL indicate reactivation of the pathogen and are known to be predictive of *Toxoplasma* encephalitis in HIV-infected subjects (131). Surprisingly, a statistically significant decrease of IgG levels was detected in vaccinees, particularly at the Tat 30 μg dose, while a very little decrease was observed in OBS subjects (Table 11). In addition, no reactivation was observed during follow-up in vaccinees, while in the OBS study three subjects became positive for IgG anti-T gondii during follow-up.

This indicates that the immune restoration (B, T cell and natural immune responses) can act against reactivation of persistent infections and their clinical manifestations and also against those still present in HAART-treated individuals.

Figure Legends

FIG. 1. Anti-Tat humoral immune responses. (A) Percentage of subjects developing anti-Tat IgM (white bar), IgG (left diagonal lines bar), IgA (right diagonal lines bar), or total anti-Tat Ab (squared bar), stratified by Tat dose and treatment groups. Responder frequency up to week 24 among groups was analyzed by the Cochran-Armitage Trend test (p=0.0267, p=0.0093 and p=0.0001 for IgM, IgG and IgA, respectively, p=0.0070 for total Ig). Tat 7.5 μg, 3×, n=28; Tat 7.5 μg, 5×, n=24; Tat 30 μg, 3×, n=24; Tat 30 μg, 5×, n=24 subjects, respectively. (B) Percentage of subjects positive for anti-Tat Ab at week 48 (Tat 7.5 μg, 3×, n=21; Tat 7.5 μg, 5×, n=17; Tat 30 μg, 3×, n=20; Tat 30 μg, 5×, n=21 subjects, respectively). Responder frequency among groups was analyzed as described above (p=0.0057 and p=0.0045 for IgM and IgG, respectively, p=0.0014 for total Ig). (C) Peak of anti-Tat IgM, IgG or IgA titres (geometric mean and range) up to 24 weeks after the first immunization from subjects positive for anti-Tat Ab (diamond Tat 7.5 μg and square Tat 30 μg). Anti-Tat IgM: Tat 7.5 μg, n=21; Tat 30 μg, n=30. Anti-Tat IgG: Tat 7.5 μg, n=30; Tat 30 μg, n=40. Anti-Tat IgA: Tat 7.5 μg, n=8; Tat 30 μg, n=27 subjects, respectively. (D) Anti-Tat IgM, IgG or IgA titres at 48 weeks after the first immunization from subjects positive for anti-Tat Ab. Anti-Tat IgM: Tat 7.5 μg, n=6; Tat 30 μg, n=22. Anti-Tat IgG: Tat 7.5 μg, n=7; Tat 30 μg, n=21. Anti-Tat IgA: Tat 7.5 μg, n=5; Tat 30 μg, n=14 subjects, respectively.

FIG. 2. Anti-Tat cellular immune responses. (A) Percentage of subjects showing anti-Tat specific production of IFN-γ, IL-2 or IL-4, respectively, measured at baseline (white bar) and up to week 48 after the first immunization (left diagonal lines bar) and stratified by Tat dose (Tat 7.5, n=37; Tat 30 µg, n=39 subjects, respectively). (B) Percentage of subjects showing anti-Tat CD4+ or CD8+ lymphoproliferative responses measured at baseline and up to week 48 and stratified by Tat dose (Tat 7.5 µg, n=32; Tat 30 µg, n=36). The analysis was performed using the McNemar's test: *p<0.05, **p<0.01.

FIG. 3. Expression of activation markers on CD8+ T Cells after Tat immunization. Changes from baseline of CD8+ T cells (gating on CD8+ T cells) expressing (A) CD38, (B) HLA-DR, or (C) both CD38 and HLA-DR. Results are shown according to Tat dose and time after the first immunization. Data are presented as the mean % changes (±standard error) at week 8, 12, 20, 48, 60 and 72. White bars: Tat 7.5 µg, n=28 up to week 20, n=15 at week 48, n=9 at week 60 and n=8 at week 72; left diagonal lines bars: Tat 30 µg, n=27 up to week 20, n=21 at week 48, n=9 at week 60 and n=10 at week 72, respectively. The t-Test for paired data was used for the analyses: *p<0.05.

FIG. 4. Expression of activation markers on CD4+ T Cells after Tat immunization. Changes from baseline of CD4+ T cells (gating on CD4+ T cells) expressing (A) CD38, (B) HLA-DR, or (C) both CD38 and HLA-DR. Results are shown according to Tat dose and time after the first immunization. Data are presented as the mean % changes (±standard error) at week 8, 12, 20, 48, 60 and 72. White bars: Tat 7.5 µg, n=28 up to week 20, n=15 at week 48, n=9 at week 60 and n=8 at week 72; left diagonal lines bars: Tat 30 µg, n=27 up to week 20, n=21 at week 48, n=9 at week 60 and n=10 at week 72, respectively. The t-Test for paired data was used for the analyses: *p<0.05.

FIG. 5. Production of β2-microglobulin and neopterin after Tat immunization. Changes from baseline, according to Tat dose, of (A) β2-microglobulin serum levels (mg/L) and (B) Neopterin (nmol/L). White bars: Tat 7.5 µg; left diagonal lines bars: Tat 30 µg. Data are presented as the mean changes (±standard error) at 4, 16 and 24 weeks (Tat 7.5 µg, n=37, Tat 30 µg, n=40 subjects, respectively). The t-Test for paired data was used for the analyses: *p<0.05.

FIG. 6. Production of total Ig after Tat immunization. Total IgM (A), IgG (B) and IgA (C) serum levels (mg/dL) are shown. White bars: Tat 7.5 µg, n=37; left diagonal lines bars: Tat 30 µg, n=40. Data are presented as the mean changes (±standard error). The t-Test for paired data was used for the analyses: *p<0.05.

FIG. 7. CD25 and FOXP3 expression on CD4+ T Cells after Tat immunization.

(A) Changes from baseline of CD4+ lymphocytes expressing CD25 are shown according to Tat dose and time after the first immunization (Tat 7.5 µg, n=44 up to week 20, n=27 at week 48, n=12 at week 60, n=19 at week 72, n=10 at week 84; Tat 30 µg, n=39 up to week 20, n=31 at week 48, n=10 at week 60, n=20 at week 72, n=15 at week 84, respectively). (B) Changes from baseline of the percentage of CD4+CD25+ lymphocytes expressing FOXP3+ (Tat 7.5 µg, n=43 up to week 20, n=26 at week 48, n=12 at week 60, n=19 at week 72, n=10 at week 84; Tat 30 µg, n=34 up to week 20, n=26 at week 48, n=9 at week 60, n=16 at week 72, n=12 at week 84, respectively). (C) Changes from baseline of the percentage of CD4+ T cells expressing CD25+FOXP3+ (Tat 7.5 µg, n=43 up to week 20, n=26 at week 48, n=12 at week 60, n=19 at week 72, n=10 at week 84; Tat 30 µg, n=34 up to week 20, n=26 at week 48, n=9 at week 60, n=16 at week 72, n=12 at week 84, respectively). (D) Changes from baseline of the absolute number of CD4+ lymphocytes expressing CD25+FOXP3+ (Tat 7.5 µg, n=39 up to week 20, n=24 at week 48, n=11 at week 60, n=15 at week 72, n=9 at week 84; Tat 30 µg, n=33 up to week 26, n=31 at week 48, n=8 at week 60, n=14 at week 72, n=11 at week 84, respectively). White bars: Tat 7.5 µg; left diagonal lines bars: Tat 30 µg. Data are presented as the mean changes (±standard error) evaluated at 8, 12, 20, 48, 60, 72 and 84 weeks after the first immunization. The t-Test for paired data was used for the analyses: *p<0.05.

FIG. 8. Evaluation of PBMC viability, CD4+ T cell and B cell counts after Tat immunization. (A) Changes from baseline of in vitro PBMC viability, stratified by Tat dose. White bars: Tat 7.5 µg, n=44 up to week 20, n=33 at week 48, n=14 at week 60, n=22 at week 72 and n=11 at week 84; left diagonal lines bars: Tat 30 µg, n=46 up to week 20 n=38 at week 48, n=15 at week 60, n=24 at week 72 and n=15 at week 84, respectively. (B) Changes from baseline of CD4+ T cells/µL (data from clinical sites), stratified by Tat dose. White bars: Tat 7.5 µg, n=47 up to week 20, n=34 at week 48, n=13 at week 60, n=19 at week 72 and n=11 at week 84; left diagonal lines bars: Tat 30 µg, n=45 up to week 20 n=36 at week 48, n=12 at week 60, n=21 at week 72 and n=13 at week 84, respectively. (C) Changes from baseline of B cells/A, stratified by Tat dose. White bars: Tat 7.5 µg, n=44 up to week 20, n=34 at week 48, n=13 at week 60, n=17 at week 72 and n=9 at week 84; left diagonal lines bars: Tat 30 µg, n=45 up to week 20 n=36 at week 48, n=12 at week 60, n=18 at week 72 and n=10 at week 84, respectively. The t-Test for paired data was used for the analyses: *p<0.05.

FIG. 9. Evaluation of the percentage of CD4+, CD8+, NK and B pells in all Tat-immunized Subjects. Changes from baseline of CD4+, CD8+, NK and B cells (percentage) for all immunized subjects (n=92 up to week 20, n=70 at week 48, n=25 at week 60, n=40 at week 72 and n=24 at week 84). The t-Test for paired data was used for the analyses: *p<0.05.

FIG. 10. Effect of Tat immunization on naïve, central and effector memory CD4+ and CD8+ T cells. Percentage of naïve (CD45RA+/CD62L+), effector RA+ (CD45RA+/CD62L−, Temra) or RA-(CD45RA−/CD62L−, Temro) and central memory (CD45RA−/CD62L+, Tcm) CD4+ (A) or CD8+ (B) T cells at baseline and at week 8, 12, 20, 48, 60 and 72 after the first immunization for subjects immunized with both Tat doses (n=35 up to week 20, n=17 at week 48, n=9 at week 60 and n=8 at week 72). Asterisk indicates significant changes from baseline. The t-Test for paired data was used for the analyses: *p<0.05.

FIG. 11. Cellular immune responses against Env or recall antigens after Tat immunization.

Percentage of responders at baseline (white bar) and up to week 48 (left diagonal lines bar) are stratified by Tat dose. Percentage of subjects showing (A) anti-Env production of IFN-γ, IL-2 and IL-4 (Tat 7.5 µg, n=34; Tat 30 µg, n=35) and (B) CD4+ or CD8+ lymphoproliferative responses (Tat 7.5 µg, n=32; Tat 30 µg, n=35); (C) anti-*Candida* cytokines production (Tat 7.5 µg, n=34; Tat 30 µg, n=35), and (D) CD4+ or CD8+ lymphoproliferative responses (Tat 7.5 µg, n=32; Tat 30 µg, n=34); (E) anti-CEF (Cytomegalovirus, Epstein-Barr and Flu viruses) production of IFN-γ, IL-2 and IL-4 (Tat 7.5 µg, n=36; Tat 30 µg, n=38), and (F) CD4+ or CD8+ lymphoproliferative responses (Tat 7.5 µg, n=32; Tat 30 µg, n=34). The analysis was performed using the McNemar's test: *p<0.05.

FIG. 12. Proviral HIV DNA. Total HIV DNA (A), Integrated DNA (B) and 2-LTR circles (C) are shown in subjects immunized with Tat (n=4) and subjects enrolled in OBS study (n=3). Data are presented as median values (copies/µg). White bars and left diagonal lines bars indicate the median values at baseline and at week 72, respectively.

Figure 13:
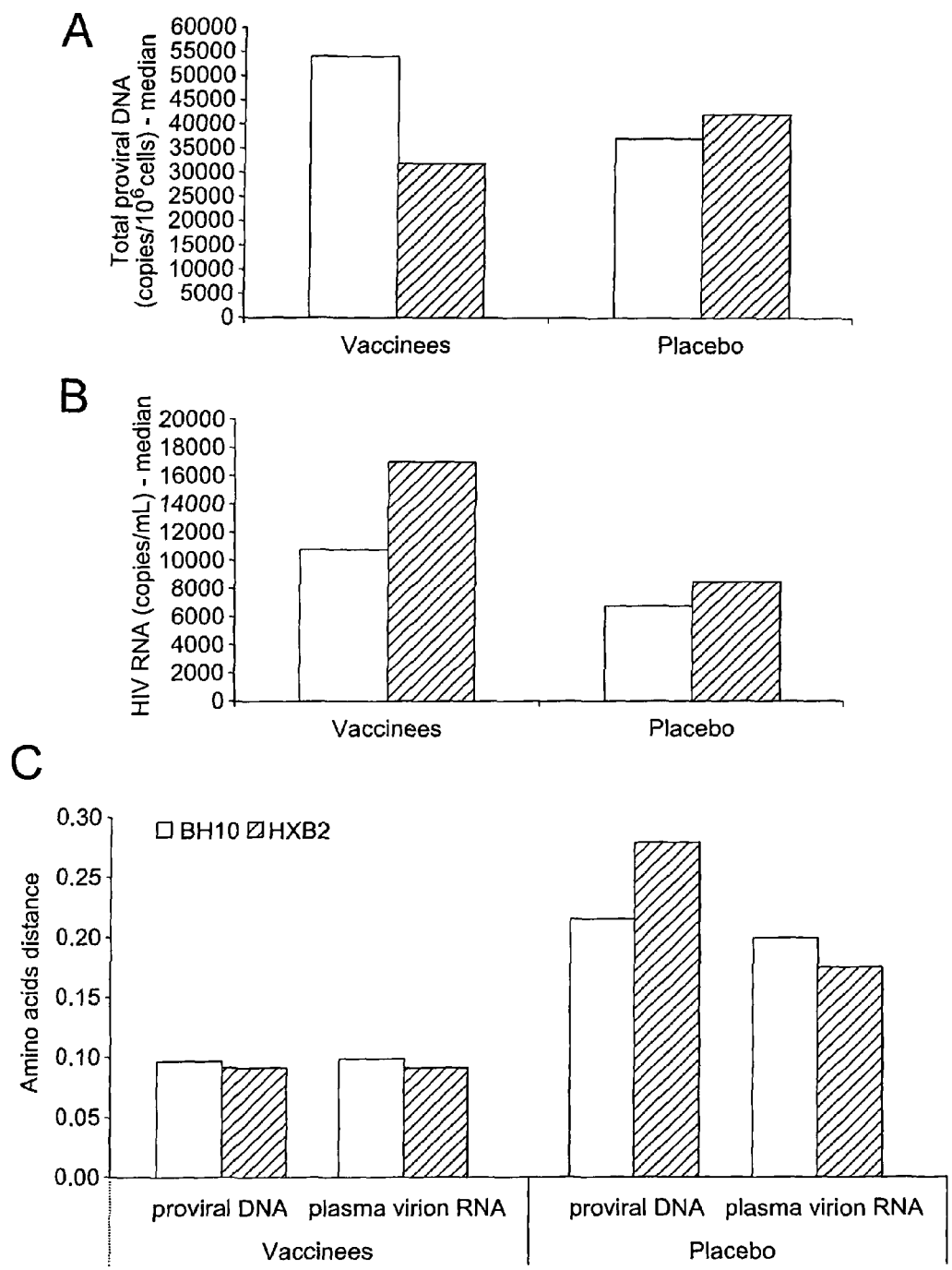
FIG. 13 shows proviral HIV DNA, plasma viral RNA and Tat sequences in patients undergoing a clinical trial where Tat was administered.
Figure 14:
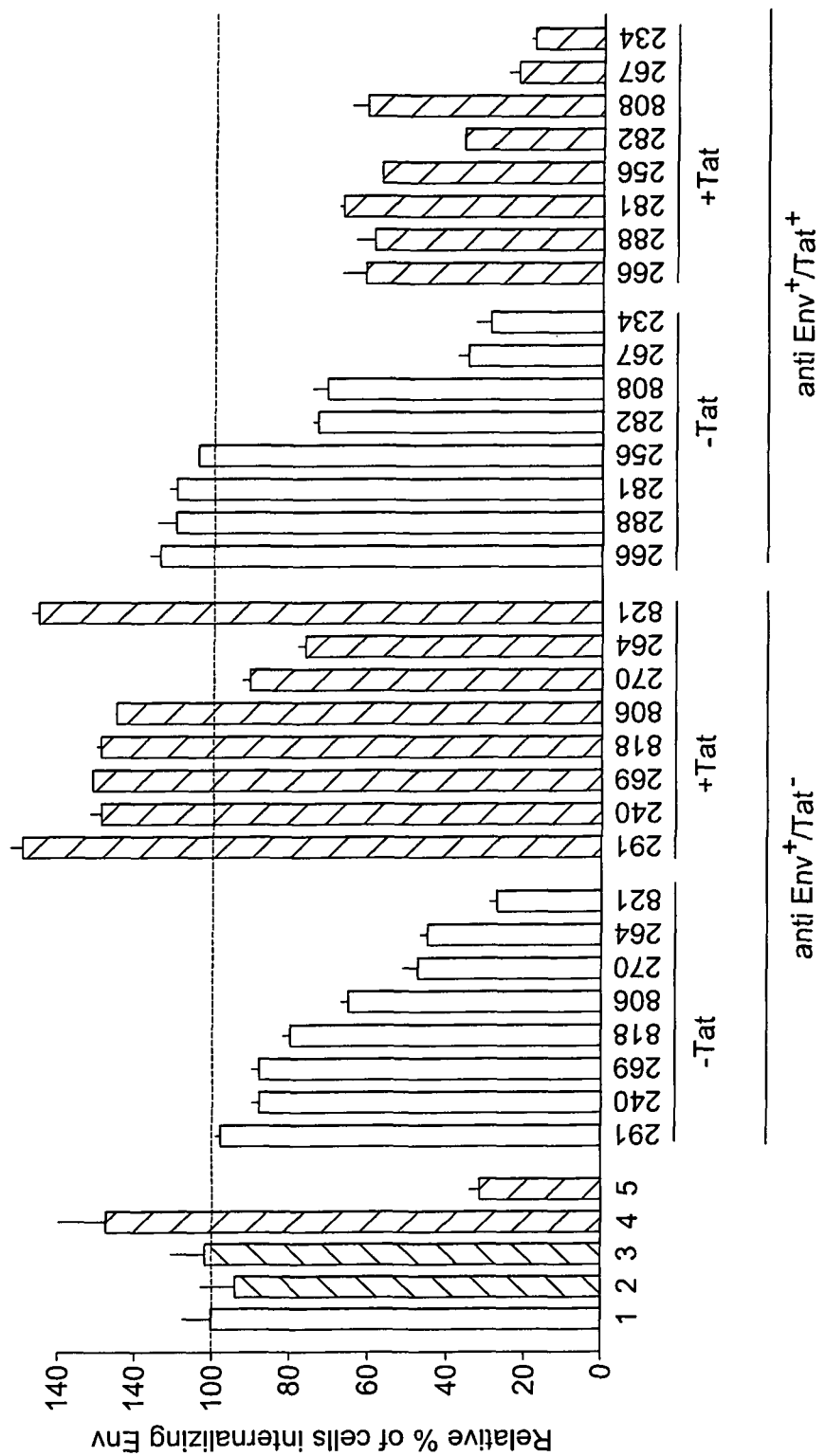
FIG. 14 shows neutralization of the entry of the Tat and Env complex in dendritic cells by sera from HIV-infected individuals negative or positive for anti-Tat antibodies.

FIG. 13. Proviral HIV DNA, plasma viral RNA and Tat sequences. Total HIV DNA (A) and plasma viral RNA (B) of asymptomatic HIV positive subjects enrolled in the ISS T-001 clinical trial. Subjects immunized with Tat, n=9; Placebos, n=7. Data are presented as median values. White bars and left diagonal lines bars indicate the median values at baseline and at week 16, respectively. Panel (C) represents the changes of the genetic distance from baseline of the HIV-1 Tat sequences obtained from proviral DNA and plasma viral RNA of vaccinees and placebos. The levels of genetic diversity of both the proviral DNA and circulating virus were compared to the prototypical HIV sequences (BH10 and BXB2), according to the Eigen's model. Genetic distance resulted significantly lower in vaccinees as compared to placebo recipients (p<0.05, t-test).

FIG. 14. Neutralization of the Tat and Env complex by sera from HIV-infected individuals negative or positive for anti-Tat antibodies. Neutralization of the Tat and Env complex by sera from HIV-infected individuals negative or positive for anti-Tat antibodies (Ab). Effect of sera from HIV-infected subjects on trimeric ΔV2Env entry in MDDC in the presence or absence of Tat (intra-cyto Env staining at FACS). The bars represent the percentage of entry of Env incubated with Tat and/or with donors' sera as compared to entry of Env alone incubated in buffer. Data are expressed as mean and SD of experiments performed in duplicate or triplicate. Env (0.4 μM) was incubated in the presence or absence of an equimolar Tat concentration in the presence of sera diluted in PBS buffer (1:30) or the anti-Tat Mab 4373 (6 μM). Bar 1, Env alone in PBS buffer; Bar 2, as bar 1 plus a pool of sera from 6 HIV-negative donors; Bar 3, as bar 2 plus MAb 4373; Bar 4, as bar 2 plus Tat; Bar 5, as bar 3 plus Tat; − Tat, Env pre-incubated in buffer; + Tat, Env pre-incubated with Tat; anti-Env[+]/Tat[−], sera positive for anti-Env Ab and negative for anti-Tat Ab; Env[+]/Tat[+], sera positive for anti-Env and anti-Tat Ab; the codes of the anti-Tat Ab negative or positive sera are indicated at the bottom of the bars.

Tables

TABLE 1

Baseline characteristics of the study participants in ISS T-002

| | ISS T-002<br>(n = 100)[a] |
|---|---|
| Age (yr) | |
| Mean ± s.d.[b] | 41 ± 7 |
| Range | 23-54 |
| Sex (%) | |
| Male | 81 |
| Female | 19 |
| CD4[+] nadir (cells/μL) | |
| Mean ± s.d. | 339 ± 124 |
| Range | 82-846 |
| HIV RNA (copies/mL) | <50 |
| Time since diagnosis of HIV (yr) | |
| Mean ± s.d. | 9 ± 6 |
| Range | 1-25 |

TABLE 1-continued

Baseline characteristics of the study participants in ISS T-002

| | ISS T-002<br>(n = 100)[a] |
|---|---|
| Time since HAART initiation (yr)[c] | |
| Mean ± s.d. | 6 ± 4 |
| Range | 0-19 |
| Current HAART regimen (%) | |
| Includes PI | 26 |
| Includes NNRTI | 64 |
| Includes NRTI | 10 |

[a]Number of evaluable individuals.
[b]Standard deviation.
[c]Based on 96 individuals.

TABLE 2

Baseline characteristics of study participants in ISS OBS T-002

| | ISS OBS T-002<br>(n = 88)[a] |
|---|---|
| Age (yr)[b] | |
| Mean ± s.d. | 44 ± 8 |
| Range | 26-65 |
| Sex (%) | |
| Male | 75.0 |
| Female | 25.0 |
| CD4[+] nadir (cells/μL) | |
| Mean ± s.d. | 206 ± 140 |
| Range | 2-612 |
| Time since diagnosis of HIV (yr)[c] | 10 ± 7 |
| Range | 1-23 |
| Time since ART initiation (yr) | 6 ± 5 |
| Range | 0-21 |
| Current antiretroviral regimen (%)[d] | |
| Includes PI | 38 |
| Includes NNRTI | 56 |
| Includes NRTI | 6 |

[a]Number of individuals.
[b]Based on 87 individuals
[c]Based on 77 individuals
[d]Based on 87 individuals

TABLE 3

Tat-specific cellular immune responses in subjects with a positive response after immunization with Tat.

| | Tat 7.5 µg[b] | | | Tat 30 µg[c] | | |
|---|---|---|---|---|---|---|
| Responders | n | Baseline | Up to week 48 | n | Baseline | Up to week 48 |
| IFN-γ | | | | | | |
| Peak[a](SFC/10[6]cells) | 10 | 26 (10-46) | 107 (58-188)** | 7 | 14 (12-46) | 50 (42-152) |
| IL-2 | | | | | | |
| Peak[a](SFC/10[6] cells) | 14 | 7 (0-28) | 49 (26-104)* | 14 | 11 (4-22) | 34 (26-38)** |
| IL-4 | | | | | | |
| Peak[a](SFC/10[6] cells) | 6 | 3 (0-10) | 42 (36-46) | 6 | 1 (0-2) | 34 (10-58)* |
| CD4 Proliferation | | | | | | |
| Peak[a](fold increase) | 23 | 1.9 (1.4-2.9) | 2.5 (2.1-4.5)** | 27 | 2.2 (1.6-3.2) | 3.4 (2.2-5.6)** |
| CD8 Proliferation | | | | | | |
| Peak[a](fold increase) | 20 | 2.1 (1.4-3.5) | 4.5 (2.6-8.5)** | 27 | 2.7 (1.6-6.5) | 5.9 (2.5-8.4)** |

[a]Median (interquartile range) of peak of responses, weeks 8, 12, 20, 48.
[b]Total subject tested for cytokines: 37; for proliferation: 39.
[c]Total subjects tested for proliferation: 32; for proliferation: 36.
*P < 0.05, **P < 0.01

The median intensity, with interquartile range of peak of responses, is shown for subjects with at least a positive cellular response at any given time point after the first immunization and up to week 48. Pre-post vaccination median change was evaluated by the Wilcoxon signed-rank test. IFN-γ, IL-2, IL-4 production by PBMC and CD4+ or CD8+ lymphoproliferative responses were measured at baseline and up to week 48 after the first immunization. Results are stratified by Tat doses, (7.5 and 30 µg). n indicates the number of responders.

TABLE 4

Tat-specific cellular immune responses in ISS OBS T-002 for subjects with a positive response (responders) after 48 weeks of follow-up.

| | | Total Subjects[b] | |
|---|---|---|---|
| Responders | n | Baseline | Up to week 48 |
| IFN-γ | | | |
| Peak[a] (SFC/10[6] cells) | 13 | 36 (14-62) | 96 (40-136)** |
| IL-2 | | | |
| Peak[a] (SFC/10[6] cells) | 28 | 8 (1-15) | 41 (17-69)** |
| IL-4 | | | |
| Peak[a] (SFC/10[6] cells) | 17 | 0 (0-8) | 28 (16-68)** |
| CD4 Proliferation | | | |
| Peak[a] (fold increase) | 30 | 1.7 (1.3-2.5) | 3.1 (2.7-4.7)** |
| CD8 Proliferation | | | |
| Peak[a] (fold increase) | 35 | 1.5 (1.1-2.9) | 3.0 (2.4-7.0)** |

[a]Median (interquartile range) of peak of responses, weeks 12, 24, 36, 48
[b]Subject tested for cytokines: 84; for proliferation: 67
*P < 0.05,
**P < 0.01

TABLE 5

Immune activation markers and T-reg at baseline in study participants.

| | n | Mean ± s.e. |
|---|---|---|
| FOXP3+ on CD4+CD25+ T cells (%) | 77 | 30.5 ± 1.4 |
| CD25+FOXP3+ on CD4+ T cells (%) | 77 | 2.8 ± 0.2 |
| CD25+ on CD4+ T cells (%) | 83 | 9.0 ± 0.3 |
| CD38+HLA-DR− on CD8+ T cells (%) | 55 | 31.0 ± 1.5 |
| HLA-DR+CD38− on CD8+ T cells (%) | 55 | 7.4 ± 0.8 |
| CD38+HLA-DR+ on CD8+ T cells (%) | 55 | 7.8 ± 0.7 |
| CD38+ HLA-DR− on CD4+ T cells (%) | 54 | 50.7 ± 1.7 |
| HLA-DR+CD38− on CD4+ T cells (%) | 54 | 5.0 ± 0.5 |
| CD38+HLA-DR+ on CD4+T cells (%) | 54 | 4.0 ± 0.4 |
| β2-microglobulin (mg/L) | 79 | 1.8 ± 0.1 |
| Neopterin (nmol/L) | 79 | 7.4 ± 1.0 |
| Total IgM (mg/dL) | 79 | 76 ± 5 |
| Total IgG (mg/dL) | 79 | 1029 ± 31 |
| Total IgA (mg/dL) | 79 | 200 ± 11 |

Mean values (± standard error) of phenotypic and biochemical immune activation markers and T-regs of the study participants at baseline. n indicates the number of individuals tested for each parameter.

TABLE 6

Immune activation markers and T-regs at baseline in Subjects of ISS OBS T-002.

| | n | Mean ± s.e. |
|---|---|---|
| FOXP3+ on CD4+CD25+ T cells (%) | 30 | 33.6 ± 2.1 |
| CD25+FOXP3+ on CD4+ T cells (%) | 30 | 2.8 ± 0.2 |
| CD25+ on CD4+ T cells (%) | 33 | 9.8 ± 0.4 |
| CD38+HLA-DR− on CD8+ T cells (%) | 16 | 32.8 ± 2.8 |
| HLA-DR+CD38− on CD8+ T cells (%) | 16 | 14.4 ± 1.6 |
| CD38+HLA-DR+ on CD8+ T cells (%) | 16 | 16.7 ± 2.6 |
| CD38+ HLA-DR− on CD4+ T cells (%) | 16 | 51.6 ± 4.1 |
| HLA-DR+CD38− on CD4+ T cells (%) | 16 | 6.6 ± 1.1 |
| CD38+HLA-DR+ on CD4+T cells (%) | 16 | 4.6 ± 1.0 |
| β2-microglobulin (mg/L) | 29 | 1.9 ± 0.1 |
| Neopterin (nmol/L) | 29 | 5.9 ± 0.3 |
| Total IgM (mg/dL) | 29 | 113 ± 12 |
| Total IgG (mg/dL) | 29 | 1283 ± 50 |
| Total IgA (mg/dL) | 29 | 276 ± 28 | n indicates the number of individuals tested for each parameter.

TABLE 7

Inverse correlation between baseline values and changes after Tat immunization of immune activation markers and T-regs.

| ISS T-002 | n | Pearson correlation coefficient | p-value |
|---|---|---|---|
| FOXP3$^+$ on CD4$^+$CD25$^+$ T cells (%) | 58 | r = −0.7 | <0.0001 |
| CD25$^+$FOXP3$^+$ on CD4$^+$ T cells (%) | 54 | r = −0.6 | <0.0001 |
| CD25$^+$ on CD4$^+$ T cells (%) | 54 | r = −0.6 | <0.0001 |
| CD38$^+$HLA-DR$^-$ on CD8$^+$ T cells (%) | 36 | r = −0.3 | 0.0508 |
| CD38$^-$HLA-DR$^+$ on CD8$^+$ T cells (%) | 36 | r = −0.5 | 0.0034 |
| CD38$^+$HLA-DR$^+$ on CD8$^+$ T cells (%) | 36 | r = −0.6 | 0.0003 |
| CD38$^+$ HLA-DR$^-$ on CD4$^+$ T cells (%) | 35 | r = −0.2 | 0.0867 |
| HLA-DR$^+$CD38$^-$ on CD4$^+$ T cells (%) | 35 | r = −0.6 | <0.0001 |
| CD38$^+$HLA-DR$^+$ on CD4$^+$T cells (%) | 35 | r = −0.9 | <0.0001 |
| β2-microglobulin (mg/L) | 79 | r = −0.3 | 0.0016 |
| Neopterin (nmol/L) | 79 | r = −0.9 | <0.0001 |
| Total IgM (mg/dL) | 79 | r = −0.1 | 0.4729 |
| Total IgG (mg/dL) | 79 | r = −0.4 | <0.0001 |
| Total IgA (mg/dL) | 79 | r = 0.0 | 0.9685 |

The relationship between baseline values and changes at week 48 (or week 24 for β2-microglobulin, neopterin and total Ig) was evaluated by the Pearson correlation coefficient (r) after cumulating both Tat doses. n indicates the number of individuals evaluated for each parameter.

TABLE 8

Cellular immune responses against Env or recall antigens after Tat immunization.

(a) Env

| Responders | Tat 7.5 μg[b] | | | Tat 30 μg[c] | | |
|---|---|---|---|---|---|---|
| | n | Baseline | Up to week 48 | n | Baseline | Up to week 48 |
| IFN-γ | | | | | | |
| Peak[a](SFC/10$^6$ cells) | 22 | 47 (8-184) | 379 (86-546)** | 23 | 60 (12-226) | 250 (82-998)** |
| IL-2 | | | | | | |
| Peak[a](SFC/10$^6$ cells) | 21 | 40 (18-76) | 78 (52-160)** | 22 | 26 (14-50) | 50 (40-114)** |
| IL-4 | | | | | | |
| Peak[a](SFC/10$^6$ cells) | 21 | 52 (16-100) | 104 (46-444)** | 19 | 24 (8-64) | 78 (26-132) |
| CD4 Proliferation | | | | | | |
| Peak[a](fold increase) | 15 | 1.5 (0.8-2.2) | 2.4 (2.1-4.7)** | 24 | 1.4 (0.7-3.0) | 3.1 (2.1-4.4)** |
| CD8 Proliferation | | | | | | |
| Peak[a](fold increase) | 19 | 1.8 (1.0-2.9) | 3.3 (2.7-7.4)** | 21 | 2.3 (1.1-5.0) | 5.1 (2.8-6.7)* |

[a]Median (interquartile range) of peak of responses, weeks 8, 12, 20, 48.
[b]Total subject tested for cytokines: 34; for proliferation: 35.
[c]Total subjects tested for cytokines: 32; for proliferation: 35.
*P < 0.05, **P < 0.01

(b) Candida

| Responders | Tat 7.5 μg[b] | | | Tat 30 μg[c] | | |
|---|---|---|---|---|---|---|
| | n | Baseline | Up to week 48 | n | Baseline | Up to week 48 |
| IFN-γ | | | | | | |
| Peak[a](SFC/10$^6$ cells) | 7 | 24 (0-70) | 82 (46-160)* | 8 | 82 (4-195) | 199 (66-305) |
| IL-2 | | | | | | |
| Peak[a](SFC/10$^6$ cells) | 28 | 98 (32-181) | 153 (101-346)** | 31 | 76 (56-116) | 152 (96-276)** |
| IL-4 | | | | | | |
| Peak[a](SFC/10$^6$ cells) | 13 | 8 (0-34) | 66 (36-124)** | 15 | 8 (2-14) | 66 (60-280)** |
| CD4 Proliferation | | | | | | |
| Peak[a](fold increase) | 21 | 1.6 (1.3-2.3) | 4.5 (2.2-5.7)** | 26 | 1.7 (1.2-3.1) | 3.8 (2.8-4.9)** |
| CD8 Proliferation | | | | | | |
| Peak[a](fold increase) | 19 | 1.8 (1.3-5.0) | 4.9 (2.8-9.9)* | 20 | 1.4 (1.2-3.7) | 5.6 (4.0-8.3)** |

[a]Median (interquartile range) of peak of responses, weeks 8, 12, 20, 48.
[b]Total subject tested for cytokines: 34; for proliferation: 35.
[c]Total subjects tested for cytokines: 32; for proliferation: 34.
P < 0.05, P < 0.01

TABLE 8-continued

Cellular immune responses against Env or recall antigens after Tat immunization.

(c) CEF

| | Tat 7.5 μg[b] | | | Tat 30 μg[c] | | |
| --- | --- | --- | --- | --- | --- | --- |
| Responders | n | Baseline | Up to week 48 | n | Baseline | Up to week 48 |
| IFN-γ | | | | | | |
| Peak[a](SFC/$10^6$ cells) | 34 | 744 (332-1162) | 1311 (788-1730)** | 38 | 1135 (332-1662) | 1975 (1098-3954)** |
| IL-2 | | | | | | |
| Peak[a](SFC/$10^6$ cells) | 35 | 278 (132-510) | 518 (348-650)** | 36 | 274 (141-737) | 751 (502-1101)** |
| IL-4 | | | | | | |
| Peak[a](SFC/$10^6$ cells) | 29 | 298 (140-736) | 728 (454-1132)** | 32 | 447 (99-642) | 648 (470-946)** |
| CD4 Proliferation | | | | | | |
| Peak[a](fold increase) | 4 | 0.9 (0.8-1.2) | 4.2 (3.4-4.9) | 9 | 0.7 (0.7-1.1) | 2.8 (2.6-3.0)** |
| CD8 Proliferation | | | | | | |
| Peak[a](fold increase) | 6 | 1.9 (1.4-2.7) | 2.7 (2.0-3.2) | 12 | 1.0 (0.7-1.1) | 3.0 (2.2-4.2)** |

[a]Median (interquartile range) of peak of responses, weeks 8, 12, 20, 48.
[b]Total subject tested for cytokines: 36; for proliferation: 38.
[c]Total subjects tested for cytokines: 32; for proliferation: 34.
**P < 0.01

IFN-γ, IL-2, IL-4 production by PBMC, and CD4 or CD8 lymphoproliferative responses to Env (a), *Candida* (b) and CEF (c) were measured at baseline and up to week 48 after the first immunization, respectively. Results are stratified by Tat doses, (7.5 and 30 μg). n indicates the number of responders for cytokines production and CD4 or CD8 T cell proliferation, respectively. The median intensity with interquartile range of peak of responses is shown. Pre-post vaccination median change was evaluated by Wilcoxon signed-rank test.

TABLE 9

Cellular immune responses against Env or recall antigens in subjects of ISS OBS T-002.

| | Total Subjects[b] | | |
| --- | --- | --- | --- |
| Responders | n | Baseline | Up to week 48 |
| (a) Env | | | |
| IFN-γ | | | |
| Peak[a](SFC/$10^6$ cells) | 39 | 132 (94-278) | 168 (82-310) |
| IL-2 | | | |
| Peak[a](SFC/$10^6$ cells) | 38 | 51 (24-104) | 61 (46-96) |
| IL-4 | | | |
| Peak[a](SFC/$10^6$ cells) | 57 | 144 (74-370) | 150 (76-272) |
| CD4 Proliferation | | | |
| Peak[a](fold increase) | 16 | 0.3 (0.2-0.5) | 2.3 (2.0-4.3)** |
| CD8 Proliferation | | | |
| Peak[a](fold increase) | 23 | 0.7 (0.5-1.0) | 4.3 (2.6-7.1)** |

[a]Median (interquartile range) of peak of responses, weeks 12, 24, 36, 48
[b]Subject tested for cytokines: 70; for proliferation: 64
*P < 0.05,
**P < 0.01

(b) Candida

| | | | |
| --- | --- | --- | --- |
| IFN-γ | | | |
| Peak[a](SFC/$10^6$ cells) | 24 | 43 (4-101) | 48 (24-168)* |
| IL-2 | | | |
| Peak[a](SFC/$10^6$ cells) | 53 | 142 (76-270) | 154 (100-266) |
| IL-4 | | | |
| Peak[a](SFC/$10^6$ cells) | 323 | 15 (1-57) | 64 (39-122)** |
| CD4 Proliferation | | | |
| Peak[a](fold increase) | 33 | 1.4 (1.0-3.2) | 3.0 (2.4-5.1)** |
| CD8 Proliferation | | | |
| Peak[a](fold increase) | 25 | 1.3 (0.8-1.9) | 3.7 (2.7-7.2)** |

[a]Median (interquartile range) of peak of responses, weeks 12, 24, 36, 48
[b]Subject tested for cytokines: 73; for proliferation: 64
*P < 0.05,
**P < 0.01

(c) CEF

| | | | |
| --- | --- | --- | --- |
| IFN-γ | | | |
| Peak[a](SFC/$10^6$ cells) | 69 | 844 (238-1406) | 1248 (454-2212)** |
| IL-2 | | | |
| Peak[a](SFC/$10^6$ cells) | 68 | 101 (50-469) | 519 (287-760)** |
| IL-4 | | | |
| Peak[a](SFC/$10^6$ cells) | 72 | 109 (30-215) | 474 (195-995)** |
| CD4 Proliferation | | | |
| Peak[a](fold increase) | 8 | 1.3 (1.1-1.7) | 3.0 (2.1-5.4)** |
| CD8 Proliferation | | | |
| Peak[a](fold increase) | 19 | 1.6 (1.0-2.3) | 2.8 (2.2-3.9)* |

[a]Median (interquartile range) of peak of responses, weeks 12, 24, 36, 48
[b]Subject tested for cytokines: 75; for proliferation: 64
*P < 0.05,
**P < 0.01

TABLE 10

Qualitative comparison of the results of the ISS T-002 Clinical Trial and the ISS OBS T-002 Observational Study up to 48 weeks of follow-up.

|  | ISS T-002[a] | ISS OBS T-002[c] |
|---|---|---|
| (a) Activation markers, T-regs, cell viability and lymphocyte phenotype. | | |
| *Activation markers* | | |
| *Phenotypic (%)* | | |
| CD38+HLA-DR− on CD8+ T cells | −(*) | −(*) |
| HLA-DR+CD38− on CD8+ T cells | +(*) | −(*) |
| CD38+HLA-DR+ on CD8+ T cells | +(*) | −(*) |
| CD38+ HLA-DR− on CD4+ T cells | +(*) | −(*) |
| HLA-DR+CD38− on CD4+ T cells | +(*) | −(*) |
| CD38+HLA-DR+ on CD4+T cells | −(*) | −(*) |
| CD25+ on CD4+ T cells | +/−(*) | + |
| *Biochemical* | | |
| β2-microglobulin (mg/L) | −(*) | +/− |
| Neopterin (nmol/L) | − | + |
| Total IgM (mg/dL) | +/− | − |
| Total IgG (mg/dL) | −(*) | + |
| Total IgA (mg/dL) | +(*) | +(*) |
| *T-regs* | | |
| FOXP3+ on CD4+CD25+ T cells (%) | +(*) | −(*) |
| CD25+FOXP3+ on CD4+ T cells (%) | +(*) | −(*) |
| CD25+FOXP3+ on CD4+ T cells (cells/μL) | +(*) | − |
| Cell viability (%) | +(*) | +(*) |
| *Lymphocyte cell counts (cells/μL)* | | |
| CD4+ T cell counts | +(*) | +/− |
| B cell counts | +(*) | − |
| *Lymphocyte Phenotype (%)* | | |
| CD4+ T cell | +(*) | + |
| CD8+ T cell | −(*) | − |
| NK | −(*) | +/− |
| B | +(*) | = |
| CD4/CD8 ratio | +(*) | + |
| (b) Central and effector memory T cell phenotype and cellular immune responses. | | |
| *T cell phenotype (%)* | | |
| CD4+ naïve | − | +/− |
| CD4+ Tcm | +(*) | − |
| CD4+ Temro | − | +/− |
| CD4+ Temra | − | +/− |
| CD8+ naïve | + | +/− |
| CD8+ Tcm | +(*) | − |
| CD8+ Temro | − | +/− |
| CD8+ Temra | −(*) | +/− |
| *Anti-Tat (% responders)* | | |
| γIFN production | + | +(*) |
| IL-2 production | +(*) | + |
| IL-4 production | + | +(*) |
| CD4+ proliferation | +(*) | + |
| CD8+ proliferation | +(*) | +(*) |
| *Anti-Env (% responders)* | | |
| γIFN production | +(*) | + |
| IL-2 production | +(*) | − |
| IL-4 production | + | = |
| CD4+ proliferation | +(*) | +(*) |
| CD8+ proliferation | +(*) | +(*) |
| *Anti-Candida (% responders)* | | |
| γIFN production | + | + |
| IL-2 production | +(*) | − |
| IL-4 production | + | +(*) |
| CD4+ proliferation | +(*) | +(*) |
| CD8+ proliferation | +(*) | +(*) |
| *Anti-CEF (% responders)* | | |
| γIFN production | + | +(*) |
| IL-2 production | + | +(*) |
| IL-4 production | = | +(*) |
| CD4+ proliferation | +(*) | + |
| CD8+ proliferation | +(*) | + |

[a] Subjects enrolled in the clinical trial;
[c] all evaluable subjects enrolled in the observational study.

Shown are the qualitative changes from baseline of the different study populations for all evaluated parameters.
+, increase;
−, decrease;
+/−, fluctuations (higher and lower levels as compared to baseline at different time points);
= stable;
(*), statistically significant in at least one time point.

TABLE 11

Reactivation of *Toxoplasma gondii* infection in ISS T-002 and in OBS study.

| ISS T-002 | IgG ≥150 (IU/mL) at baseline | n | 25th Pctl | Median | 75th Pctl |
|---|---|---|---|---|---|
| Vaccinees | w0 | 6 | 323 | 623 | 2614 |
|  | w4-w0 | 6 | −512 | −66 | −22 |
|  | w24-w0 | 6 | −565 | −248* | −89 |
|  | w48-w0 | 4 | −914 | −385 | −77 |
|  | w72-w0 | 3 | −507 | −60 | 155 |
| OBS T-002 | w0 | 4 | 196 | 273 | 442 |
|  | w24-w0 | 3 | −197 | −48 | 46 |
|  | w48-w0 | 4 | −37 | −12 | 56 |
|  | w72-w0 | — | | | |

Median values with interquartile range of IgG anti-*Toxoplasma gondii* in vaccinees at Tat 30 μg dose and OBS subjects. Median changes from baseline were evaluated using Wilcoxon signed-rank test (*p<0.05). n indicates the number of individuals tested at each time point.

REFERENCE LIST

1. J. H. Arnsten, R. Freeman, A. A. Howard, M. Floris-Moore, Y. Lo, R. S. Klein, Decreased bone mineral density and increased fracture risk in aging men with or at risk for HIV infection. *AIDS* 21, 617-623 (2007).
2. J. V. Baker, G. Peng, J. Rapkin, D. I. Abrams, M. J. Silverberg, R. D. MacArthur, W. P. Cavert, W. K. Henry, J. D. Neaton, CD4+ count and risk of non-AIDS diseases following initial treatment for HIV infection. *AIDS* 22, 841-848 (2008).
3. M. Battegay, R. Nuesch, B. Hirschel, G. R. Kaufmann, Immunological recovery and antiretroviral therapy in HIV-1 infection. *Lancet Infect. Dis.* 6, 280-287 (2006).
4. A. Burgi, S. Brodine, S. Wegner, M. Milazzo, M. R. Wallace, K. Spooner, D. L. Blazes, B. K. Agan, A. Armstrong, S. Fraser, N. F. Crum, Incidence and risk factors for the occurrence of non-AIDS-defining cancers among human immunodeficiency virus-infected individuals. *Cancer* 104, 1505-1511 (2005).
5. A. A. Byrnes, D. M. Harris, S. F. Atabani, B. P. Sabundayo, S. J. Langan, J. B. Margolick, C. L. Karp, Immune activation and IL-12 production during acute/early HIV infection in the absence and presence of highly active, antiretroviral therapy. *J. Leukoc. Biol.* 84, 1447-1453 (2008).
6. J. Chehimi, L. Azzoni, M. Farabaugh, S. A. Creer, C. Tomescu, A. Hancock, A. Mackiewicz, L. D'Alessandro, S. Ghanekar, A. S. Foulkes, K. Mounzer, J. Kostman, L. J. Montaner, Baseline viral load and immune activation determine the extent of reconstitution of innate immune effectors in HIV-1-infected subjects undergoing antiretroviral treatment. *J. Immunol.* 179, 2642-2650 (2007).
7. S. G. Deeks, A. N. Phillips, HIV infection, antiretroviral treatment, ageing, and non-AIDS related morbidity. *BMJ* 338, a3172 (2009).
8. L. Desquilbet, L. P. Jacobson, L. P. Fried, J. P. Phair, B. D. Jamieson, M. Holloway, J. B. Margolick, HIV-1 infection is associated with an earlier occurrence of a phenotype related to frailty. *J. Gerontol. A Biol. Sci. Med. Sci.* 62, 1279-1286 (2007).
9. R. B. Effros, C. V. Fletcher, K. Gebo, J. B. Halter, W. R. Hazzard, F. M. Horne, R. E. Huebner, E. N. Janoff, A. C. Justice, D. Kuritzkes, S. G. Nayfield, S. F. Plaeger, K. E. Schmader, J. R. Ashworth, C. Campanelli, C. P. Clayton, B. Rada, N. F. Woolard, K. P. High, Aging and infectious diseases: workshop on HIV infection and aging: what is known and future research directions. *Clin. Infect. Dis.* 47, 542-553 (2008).
10. L. Gil, G. Martinez, I. Gonzalez, A. Tarinas, A. Alvarez, A. Giuliani, R. Molina, R. Tapanes, J. Perez, O, S. Leon, Contribution to characterisation of oxidative stress in HIV/AIDS patients. *Pharmacol. Res.* 47, 217-224 (2003).
11. D. K. Glencross, G. Janossy, L. M. Coetzee, D. Lawrie, L. E. Scott, I. Sanne, J. A. McIntyre, W. Stevens, CD8/CD38 activation yields important clinical information of effective antiretroviral therapy: findings from the first year of the CIPRA-SA cohort. *Cytometry B Clin. Cytom.* 74 Suppl 1, S131-S140 (2008).
12. S. K. Grinspoon, C. Grunfeld, D. P. Kotler, J. S. Currier, J. D. Lundgren, M. P. Dube, S. E. Lipshultz, P. Y. Hsue, K. Squires, M. Schambelan, P. W. Wilson, K. E. Yarasheski, C. M. Hadigan, J. H. Stein, R. H. Eckel, State of the science conference: Initiative to decrease cardiovascular risk and increase quality of care for patients living with HIV/AIDS: executive summary. *Circulation* 118, 198-210 (2008).
13. M. D. Hazenberg, S. A. Otto, B. H. van Benthem, M. T. Roos, R. A. Coutinho, J. M. Lange, D. Hamann, M. Prins, F. Miedema, Persistent immune activation in HIV-1 infection is associated with progression to AIDS. *AIDS* 17, 1881-1888 (2003).
14. P. Y. Hsue, K. Giri, S. Erickson, J. S. MacGregor, N. Younes, A. Shergill, D. D. Waters, Clinical features of acute coronary syndromes in patients with human immunodeficiency virus infection. *Circulation* 109, 316-319 (2004).
15. P. W. Hunt, J. N. Martin, E. Sinclair, B. Bredt, E. Hagos, H. Lampiris, S. G. Deeks, T cell activation is associated with lower CD4+ T cell gains in human immunodeficiency virus-infected patients with sustained viral suppression during antiretroviral therapy. *J. Infect. Dis.* 187, 1534-1543 (2003).
16. P. W. Hunt, Role of immune activation in HIV pathogenesis. *Curr. HIV/AIDS Rep.* 4, 42-47 (2007).
17. C. F. Kelley, C. M. Kitchen, P. W. Hunt, B. Rodriguez, F. M. Hecht, M. Kitahata, H. M. Crane, J. Willig, M. Mugavero, M. Saag, J. N. Martin, S. G. Deeks, Incomplete peripheral CD4+ cell count restoration in HIV-infected patients receiving long-term antiretroviral treatment. *Clin. Infect. Dis.* 48, 787-794 (2009).
18. G. D. Kirk, C. Merlo, P, O'Driscoll, S. H. Mehta, N. Galai, D. Vlahov, J. Samet, E. A. Engels, HIV infection is associated with an increased risk for lung cancer, independent of smoking. *Clin. Infect. Dis.* 45, 103-110 (2007).
19. A. Monforte, D. Abrams, C. Pradier, R. Weber, P. Reiss, F. Bonnet, O. Kirk, M. Law, W. S. De, N. Friis-Moller, A. N. Phillips, C. A. Sabin, J. D. Lundgren, HIV-induced immunodeficiency and mortality from AIDS-defining and non-AIDS-defining malignancies. *AIDS* 22, 2143-2153 (2008).
20. M. C. Odden, R. Scherzer, P. Bacchetti, L. A. Szczech, S. Sidney, C. Grunfeld, M. G. Shlipak, Cystatin C level as a marker of kidney function in human immunodeficiency virus infection: the FRAM study. *Arch. Intern. Med.* 167, 2213-2219 (2007).
21. D. E. Smith, B. D. Walker, D. A. Cooper, E. S. Rosenberg, J. M. Kaldor, Is antiretroviral treatment of primary HIV infection clinically justified on the basis of current evidence? *AIDS* 18, 709-718 (2004).
22. H. Valdez, E. Connick, K. Y. Smith, M. M. Lederman, R. J. Bosch, R. S. Kim, C. M. St, D. R. Kuritzkes, H. Kessler, L. Fox, M. Blanchard-Vargas, A. Landay, Limited immune restoration after 3 years' suppression of HIV-1 replication in patients with moderately advanced disease. *AIDS* 16, 1859-1866 (2002).
23. R. Weber, C. A. Sabin, N. Friis-Moller, P. Reiss, W. M. El-Sadr, O. Kirk, F. Dabis, M. G. Law, C. Pradier, W. S. De, B. Akerlund, G. Calvo, A. Monforte, M. Rickenbach, B. Ledergerber, A. N. Phillips, J. D. Lundgren, Liver-related deaths in persons infected with the human immunodeficiency virus: the D:A:D study. *Arch. Intern. Med.* 166, 1632-1641 (2006).
24. Zhu T, Muthui D, Holte S, Nickle D, Feng F et al. (2002) Evidence for human immunodeficiency virus type 1 replication in vivo in CD14(+) monocytes and its potential role as a source of virus in patients on highly active antiretroviral therapy. *J Virol* 76: 707-716.
25. Lambotte O, Taoufik Y, de Goer M G, Wallon C, Goujard C et al. (2000) Detection of infectious HIV in circulating monocytes from patients on prolonged highly active antiretroviral therapy. *J Acquir Immune Defic Syndr* 23: 114-119.
26. Kelly J, Beddall M H, Yu D, Iyer S R, Marsh J W et al. (2008) Human macrophages support persistent transcription from unintegrated HIV-1 DNA. *Virology* 372: 300-312.
27. Wu Y, Marsh J W (2001) Selective transcription and modulation of resting T cell activity by preintegrated HIV DNA. *Science* 293: 1503-1506.
28. Lassen K G, Bailey J R Siliciano R F (2004) Analysis of human immunodeficiency virus type 1 transcriptional elongation in resting CD4+ T cells in vivo. *J Virol* 78: 9105-9114.
29. Lassen K G, Ramyar I O C, Bailey J R, Zhou Y Siliciano R F (2006) Nuclear retention of multiply spliced HIV-1 RNA in resting CD4+ T cells. *PLoS Pathog* 2: e68.
30. Furtado M R, Callaway D S, Phair J P, Kunstman K J, Stanton J L et al. (1999) Persistence of HIV-1 transcription in peripheral-blood mononuclear cells in patients receiving potent antiretroviral therapy. *N Engl J Med* 340: 1614-1622.
31. Zhang L, Ramratnam B, Tenner-Racz K, He Y, Vesanen M et al. (1999) Quantifying residual HIV-1 replication in patients receiving combination antiretroviral therapy. *N Engl J Med* 340: 1605-1613.

32. Natarajan V, Bosche M, Metcalf J A, Ward D J, Lane H C et al. (1999) HIV-1 replication in patients with undetectable plasma virus receiving HAART. Highly active antiretroviral therapy. Lancet 353: 119-120.

33. Wu Y, Marsh J W (2003) Early transcription from nonintegrated DNA in human immunodeficiency virus infection. J Virol 77: 10376-10382.

34. Deeks S G (2009) Immune dysfunction, inflammation, and accelerated aging in patients on antiretroviral therapy. Top HIV Med 17: 118-123.

35. Margolis D. M. Eradication therapies for HIV infection: time to begin again. *AIDS Res Hum Retroviruses*. [Epub ahead of print] (2011).

36. N. Chomont, M. El-Far, P. Ancuta, L. Trautmann, F. A. Procopio, B. Yassine-Diab, G. Boucher, M. R. Boulassel, G. Ghattas, J. M. Brenchley, T. W. Schacker, B. J. Hill, D. C. Douek, J. P. Routy, E. K. Haddad, R. P. Sekaly. HIV reservoir size and persistence are driven by T cell survival and homeostatic proliferation. *Nat. Med.* 15:893-900 (2009).

37. M. J. Buzón, M. Massanella, J. M. Llibre, A. Esteve, V. Dahl, M. C. Puertas, J. M. Gatell, P. Domingo, R. Paredes, M. Sharkey, S. Palmer, M. Stevenson, B. Clotet, J. Blanco, J. Martinez-Picado. HIV-1 replication and immune dynamics are affected by raltegravir intensification of HAART-suppressed subjects. *Nat. Med.* 16:460-5 (2010).

38. Javier Martinez-Picado HIV-1 Replication and Immune Dynamics Are Impacted by Raltegravir Intensification of HAART-suppressed Patients. CROI 2010 Abstract 100LB.

39. E. H. Graf, A. M. Mexas, J, J. Yu, F. Shaheen, M. K. Liszewski, M. Di Mascio, S. A. Migueles, M. Connors, O'Doherty U. Elite Suppressors Harbor Low Levels of Integrated HIV DNA and High Levels of 2-LTR Circular HIV DNA Compared to HIV+ Patients On and Off HAART. PLoS Pathog. 7:e1001300 (2011).

40. D. D. Richman, D. M. Margolis, M. Delaney, W. C. Greene, D. Hazuda, R. J. Pomerantz, The challenge of finding a cure for HIV infection. *Science* 323, 1304-1307 (2009).

41. D. L. Birx, R. R. Redfield, K. Tencer, A. Fowler, D. S. Burke, G. Tosato, Induction of interleukin-6 during human immunodeficiency virus infection. *Blood* 76, 2303-2310 (1990).

42. D. Emilie, M. Peuchmaur, M. C. Maillot, M. C. Crevon, N. Brousse, J. F. Delfraissy, J. Dormont, P. Galanaud, Production of interleukins in human immunodeficiency virus-1-replicating lymph nodes. *J. Clin. Invest* 86, 148-159 (1990).

43. T. Matsuyama, N. Kobayashi, N. Yamamoto, Cytokines and HIV infection: is AIDS a tumor necrosis factor disease? *AIDS* 5, 1405-1417 (1991).

44. L. Weiss, N. Haeffner-Cavaillon, M. Laude, J. Gilquin, M. D. Kazatchkine, HIV infection is associated with the spontaneous production of interleukin-1 (IL-1) in vivo and with an abnormal release of IL-1 alpha in vitro. *AIDS* 3, 695-699 (1989).

45. M. W. Hull, V. D. Lima, R. S. Hogg, P. R. Harrigan, J. S. Montaner, Epidemiology of treatment failure: a focus on recent trends. *Curr. Opin. HIV AIDS* 4, 467-473 (2009).

46. P. W. Hunt, S. G. Deeks, D. R. Bangsberg, A. Moss, E. Sinclair, T. Liegler, M. Bates, G. Tsao, H. Lampiris, R. Hoh, J. N. Martin, The independent effect of drug resistance on T cell activation in HIV infection. *AIDS* 20, 691-699 (2006).

47. L. E. Jones, A. S. Perelson, Transient viremia, plasma viral load, and reservoir replenishment in HIV-infected patients on antiretroviral therapy. *J. Acquir. Immune. Defic. Syndr.* 45, 483-493 (2007).

48. R. E. Nettles, T. L. Kieffer, Update on HIV-1 viral load blips. *Curr. Opin. HIV AIDS* 1, 157-161 (2006).

49. S. Palmer, F. Maldarelli, A. Wiegand, B. Bernstein, G. J. Hanna, S. C. Brun, D. J. Kempf, J. W. Mellors, J. M. Coffin, M. S. King, Low-level viremia persists for at least 7 years in patients on suppressive antiretroviral therapy. *Proc. Natl. Acad. Sci. U.S.A* 105, 3879-3884 (2008).

50. G. Barillari, L. Buonaguro, V. Fiorelli, J. Hoffman, F. Michaels, R. C. Gallo, B. Ensoli, Effects of cytokines from activated immune cells on vascular cell growth and HIV-1 gene expression. Implications for AIDS-Kaposi's sarcoma pathogenesis. *J. Immunol.* 149, 3727-3734 (1992).

51. L. Buonaguro, G. Barillari, H. K. Chang, C. A. Bohan, V. Kao, R. Morgan, R. C. Gallo, B. Ensoli, Effects of the human immunodeficiency virus type 1 Tat protein on the expression of inflammatory cytokines. *J. Virol.* 66, 7159-7167 (1992).

52. L. Buonaguro, F. M. Buonaguro, G. Giraldo, B. Ensoli, The human immunodeficiency virus type 1 Tat protein transactivates tumor necrosis factor beta gene expression through a TAR-like structure. *J. Virol.* 68, 2677-2682 (1994).

53. H. K. Chang, R. C. Gallo, B. Ensoli, Regulation of Cellular Gene Expression and Function by the Human Immunodeficiency Virus Type 1 Tat Protein. *J. Biomed. Sci.* 2, 189-202 (1995).

54. L. Houzet, Z. Morichaud, M. Mougel, Fully-spliced HIV-1 RNAs are reverse transcribed with similar efficiencies as the genomic RNA in virions and cells, but more efficiently in AZT-treated cells. *Retrovirology.* 4, 30-2007).

55. C. Liang, J. Hu, R. S. Russell, M. Kameoka, M. A. Wainberg, Spliced human immunodeficiency virus type 1 RNA is reverse transcribed into cDNA within infected cells. AIDS *Res. Hum. Retroviruses* 20, 203-211 (2004).

56. S. G. Deeks, Immune dysfunction, inflammation, and accelerated aging in patients on antiretroviral therapy. *Top. HIV. Med.* 17, 118-123 (2009).

57. B. Ensoli, S. Bellino, A. Tripiciano, O. Longo, V. Francavilla, S. Marcotullio, A. Cafaro, O. Picconi, G. Paniccia, A. Scoglio, A. Arancio, C. Ariola, M. J. Ruiz Alvarez, M. Campagna, D. Scaramuzzi, C. Iori, R. Esposito, C. Mussini, F. Ghinelli, L. Sighinolfi, G. Palamara, A. Latini, G. Angarano, N. Ladisa, F. Soscia, V. S. Mercurio, A. Lazzarin, G. Tambussi, R. Visintini, F. Mazzotta, M. Di Pietro, M. Galli, S. Rusconi, G. Carosi, C. Torti, G. Di Perri, S. Bonora, F. Ensoli, E. Garaci. Therapeutic Immunization with HIV-1 Tat Reduces Immune Activation and Loss of Regulatory T-Cells and Improves Immune Function in Subjects on HAART. *PLoS ONE* 5:e13540 (2010).

58. Y. Ariumi, F. Serhan, P. Turelli, A. Telenti, Trono D. The integrase interactor 1 (INI1) proteins facilitate Tat-mediated human immunodeficiency virus type 1 transcription. *Retrovirology* 3:47 (2006).

59. Gathe, J., Diaz, R., Fatkenheuer, G., Zeinecker, J., Mak, C., Vilchez, R., Greaves, W., Kumar, S., Onyebuchi, C., and Dunkle, L. Phase 3 Trials of Vicriviroc in Treatment-experienced Subjects Demonstrate Safety but Not Significantly Superior Efficacy over Potent Background Regimens Alone. Abstract from the 17th Conference on Retroviruses and Opportunistic Infections. 2010. Ref Type: Generic 60. Timothy, W., Lalama, C., Tenorio, A., Landay, A., Ribaudo, H., Mckinnon, J., Gandhi, R., Mellors, J., Currier, J., and Gulick, R. Maraviroc Intensification for Suboptimal CD4+ Cell Response Despite Sustained Virologic Suppression: ACTG 5256 Abstract from the 17th Conference on Retroviruses and Opportunistic Infections. 2010.

61. Wilkin, T. and et al. Maraviroc intensification for suboptimal CD4+ cell response despite sustained virologic suppression: ACTG 5256. Abstract 285 CROI, San Francisco, Feb. 25-29. 2010.

62. M. A. Kolber, CD38+CD8+ T-cells negatively correlate with CD4 central memory cells in virally suppressed HIV-1-infected individuals. *AIDS* 22, 1937-1941 (2008).

63. S. J. Potter, C. Lacabaratz, O. Lambotte, S. Perez-Patrigeon, B. Vingert, M. Sinet, J. H. Colle, A. Urrutia, D. Scott-Algara, F. Boufassa, J. F. Delfraissy, J. Theze, A. Venet, L. A. Chakrabarti, Preserved central memory and activated effector memory CD4+ T-cell subsets in human immunodeficiency virus controllers: an ANRS EP36 study. *J. Virol.* 81, 13904-13915 (2007).

64. Wang F X, Xu Y, Sullivan J, Souder E, Argyris E G, Acheampong E A, Fisher J, Sierra M, Thomson M M, Najera R, Frank I, Kulkosky J, Pomerantz R J, Nunnari G. IL-7 is a potent and proviral strain-specific inducer of latent HIV-1 cellular reservoirs of infected individuals on virally suppressive HAART. *J Clin Invest.* 115:128-37 (2005).

65. H. Imamichi, G. Degray, D. M. Asmuth, M. A. Fischl, A. L. Landay, M. M. Lederman, I. Sereti. HIV-1 viruses detected during episodic blips following interleukin-7 administration are similar to the viruses present before and after interleukin-7 therapy. *AIDS* 25:159-64 (2011).

66. T. J. Fry, C. L. Mackall Interleukin-7: master regulator of peripheral T-cell homeostasis? *Trends Immunol.* 22:564-71 (2001).

67. R. Mazzucchelli, J. A. Hixon, R. Spolski, X. Chen, W. Q. Li, V. L. Hall, J. Willette-Brown, A. A. Hurwitz, W. J. Leonard, S. K. Durum. Development of regulatory T cells requires IL-7Ralpha stimulation by IL-7 or TSLP. *Blood* 112: 3283-3292 (2008).

68. B. Rethi, C. Fluur, A. Atlas, M. Krzyzowska, F. Mowafi, S. Grutzmeier, A. De Milito, R. Bellocco, K I Falk, E Rajnavölgyi, F. Chiodi. Loss of IL-7Ralpha is associated with CD4 T-cell depletion, high interleukin-7 levels and CD28 down-regulation in HIV infected patients. AIDS 19, 2077-2086, (2005).

69. S. A. Koesters, J. B. Alimonti, C. Wachihi, L. Matu, O. Anzala, J. Kimani, J. E. Embree, F. A. Plummer, K. R. IL-7Ralpha expression on CD4+ T lymphocytes decreases with HIV disease progression and inversely correlates with immune activation. Eur J. Immunol., 36:336-444 (2006).

70. Ho J, Moir S, Malaspina A, Howell M L, Wang W, DiPoto A C, O'Shea M A, Roby G A, Kwan R, Mican J M, Chun T W, Fauci A S. Two overrepresented B cell populations in HIV-infected individuals undergo apoptosis by different mechanisms. *Proc. Natl. Acad. Sci. USA.* 103:19436-41 (2006).

71. E. Faller, J. Kakal, R. Kumar, P. Macpherson. IL-7 and the HIV Tat protein act synergistically to down-regulate CD127 expression on CD8 T cells. *Int Immunol.* 21:203-16 (2009).

72. M. A. Curotto de Lafaille, J. J. Lafaille, Natural and adaptive foxp3+ regulatory T cells: more of the same or a division of labor? *Immunity.* 30, 626-635 (2009).

73. B. T. Rouse, P. P. Sarangi, S. Suvas, Regulatory T cells in virus infections. *Immunol. Rev.* 212, 272-286 (2006).

74. S. Abgrall, C. Rabaud, D. Costagliola; Clinical Epidemiology Group of the French Hospital Database on HIV., Incidence and risk factors for toxoplasmic encephalitis in HIV-infected patients before and during the HAART era. *Clin Infect Dis* 33: 1747-1755 (2001).

75. Bonnet F C. Lewden, T. May, L. Heripret, E. Jougla, S. Bevilacqua, D. Costagliola, D. Salmon, G. Chêrie, P. Morlat; Mortalité 2000 Study Group. Opportunistic Infections as causes of death in HIV-infected patients in the HAART era in France. Scand J Infect Dis 37: 482-487 (2005)

76. C. Hoffmann, M. Ernst, P. Meyer, E. Wolf, T. Rosenkranz, A. Plettenberg, A. Stoehr, H. A. Horst, K. Marienfeld, C. Lange. Evolving characteristics of toxoplasmosis in patients infected with human immunodeficiency virus-1: clinical course and *Toxoplasma gondii*-specific immune responses. *Clin Microbiol Infect.* 13:510-5 (2007).

77. Furco A, Carmagnat M, Chevret S, Garin Y J, Pavie J, De Castro N, Charron D, Derouin F, Rabian C, Molina J M. AIDS. Restoration of *Toxoplasma gondii*-specific immune responses in patients with AIDS starting HAART. 18; 22(16): 2087-96 (2008).

78. H. C. Chang, F. Samaniego, B. C. Nair, L. Buonaguro, B. Ensoli, HIV-1 Tat protein exits from cells via a leaderless secretory pathway and binds to extracellular matrix-associated heparan sulfate proteoglycans through its basic region. *AIDS* 11, 1421-1431 (1997).

79. B. Ensoli, G. Barillari, S. Z. Salahuddin, R. C. Gallo, F. Wong-Staal, Tat protein of HIV-1 stimulates growth of cells derived from Kaposi's sarcoma lesions of AIDS patients. *Nature* 345, 84-86 (1990).

80. B. Ensoli, L. Buonaguro, G. Barillari, V. Fiorelli, R. Gendelman, R. A. Morgan, P. Wingfield, R. C. Gallo, Release, uptake, and effects of extracellular human immunodeficiency virus type 1 Tat protein on cell growth and viral transactivation. *J. Virol.* 67, 277-287 (1993).

81. B. Ensoli, R. Gendelman, P. Markham, V. Fiorelli, S. Colombini, M. Raffeld, A. Cafaro, H. K. Chang, J. N. Brady, R. C. Gallo, Synergy between basic fibroblast growth factor and HIV-1 Tat protein in induction of Kaposi's sarcoma. *Nature* 371, 674-680 (1994).

82. G. Goldstein, HIV-1 Tat protein as a potential AIDS vaccine. *Nat. Med.* 2, 960-964 (1996).

83. F. Rayne, S. Debaisieux, H. Yezid, Y. L. Lin, C. Mettling, K. Konate, N. Chazal, S. T. Arold, M. Pugniere, F. Sanchez, A. Bonhoure, L. Briant, E. Loret, C. Roy, B. Beaumelle, Phosphatidylinositol-(4,5)-bisphosphate enables efficient secretion of HIV-1 Tat by infected T-cells. *EMBO J.* (2010).

84. E. Toschi, G. Barillari, C. Sgadari, I. Bacigalupo, A. Cereseto, D. Carlei, C. Palladino, C. Zietz, P. Leone, M. Sturzl, S. Butto, A. Cafaro, P. Monini, B. Ensoli, Activation of matrix-metalloproteinase-2 and membrane-type-1-matrix-metalloproteinase in endothelial cells and induction of vascular permeability in vivo by human immunodeficiency virus-1 Tat protein and basic fibroblast growth factor. *Mol. Biol. Cell* 12, 2934-2946 (2001).

85. Y. Wu, J. W. Marsh, Selective transcription and modulation of resting T cell activity by preintegrated HIV DNA. *Science* 293, 1503-1506 (2001).

86. M. C. Re, M. Vignoli, G. Furlini, D. Gibellini, V. Colangeli, F. Vitone, P. M. La, Antibodies against full-length Tat protein and some low-molecular-weight Tat-peptides correlate with low or undetectable viral load in HIV-1 seropositive patients. *J. Clin. Virol.* 21, 81-89 (2001).

87. P. Reiss, J. M. Lange, R. A. de, W. F. de, J. Dekker, C. Debouck, J. Goudsmit, Speed of progression to AIDS and degree of antibody response to accessory gene products of HIV-1. *J. Med. Virol.* 30, 163-168 (1990).

88. G. Rezza, V. Fiorelli, M. Dorrucci, M. Ciccozzi, A. Tripiciano, A. Scoglio, B. Collacchi, M. Ruiz-Alvarez, C. Giannetto, A. Caputo, L. Tomasoni, F. Castelli, M. Sciandra, A. Sinicco, F. Ensoli, S. Butto, B. Ensoli, The presence of anti-Tat antibodies is predictive of long-term nonprogression to AIDS or severe immunodeficiency: findings in a cohort of HIV-1 seroconverters. *J. Infect. Dis.* 191, 1321-1324 (2005).

89. T. C. Rodman, S. E. To, H. Hashish, K. Manchester, Epitopes for natural antibodies of human immunodeficiency virus (HIV)-negative (normal) and HIV-positive sera are coincident with two key functional sequences of HIV Tat protein. *Proc. Natl. Acad. Sci. U.S. A* 90, 7719-7723 (1993).

90. J. F. Zagury, A. Sill, W. Blattner, A. Lachgar, B. H. Le, M. Richardson, J. Rappaport, H. Hendel, B. Bizzini, A. Gringeri, M. Carcagno, M. Criscuolo, A. Burny, R. C. Gallo, D. Zagury, Antibodies to the HIV-1 Tat protein correlated with nonprogression to AIDS: a rationale for the use of Tat toxoid as an HIV-1 vaccine. *J. Hum. Virol.* 1, 282-292 (1998).

91. S. Butto, V. Fiorelli, A. Tripiciano, M. J. Ruiz-Alvarez, A. Scoglio, F. Ensoli, M. Ciccozzi, B. Collacchi, M. Sabbatucci, A. Cafaro, C. A. Guzman, A. Borsetti, A. Caputo, E. Vardas, M. Colvin, M. Lukwiya, G. Rezza, B. Ensoli, Sequence conservation and antibody cross-recognition of clade B human immunodeficiency virus (HIV) type 1 Tat protein in HIV-1-infected Italians, Ugandans, and South Africans. *J. Infect. Dis.* 188, 1171-1180 (2003).

92. P. Reiss, W. F. de, C. L. Kuiken, R. A. de, J. Dekker, C. A. Boucher, C. Debouck, J. M. Lange, J. Goudsmit, Contribution of antibody response to recombinant HIV-1 gene-encoded products nef, rev, tat, and protease in predicting development of AIDS in HIV-1-infected individuals. *J. Acquir. Immune. Defic. Syndr.* 4, 165-172 (1991).

93. E. Fanales-Belasio, S. Moretti, F. Nappi, G. Barillari, F. Micheletti, A. Cafaro, B. Ensoli, Native HIV-1 Tat protein targets monocyte-derived dendritic cells and enhances their maturation, function, and antigen-specific T cell responses. *J. Immunol.* 168, 197-206 (2002).

94. E. Fanales-Belasio, S. Moretti, V. Fiorelli, A. Tripiciano, M. R. Pavone Cossut, A. Scoglio, B. Collacchi, F. Nappi, I. Macchia, S. Bellino, V. Francavilla, A. Caputo, G. Barillari, M. Magnani, M. E. Laguardia, A. Cafaro, F. Titti, P. Monini, F. Ensoli, B. Ensoli, HIV-1 Tat addresses dendritic cells to induce a predominant Th1-type adaptive immune response that appears prevalent in the asymptomatic stage of infection. *J. Immunol.* 182, 2888-2897 (2009).

95. T. M. Allen, D. H. O'Connor, P. Jing, J. L. Dzuris, B. R. Mothe, T. U. Vogel, E. Dunphy, M. E. Liebl, C. Emerson, N. Wilson, K. J. Kunstman, X. Wang, D. B. Allison, A. L. Hughes, R. C. Desrosiers, J. D. Altman, S. M. Wolinsky, A. Sette, D. I. Watkins, Tat-specific cytotoxic T lymphocytes select for SIV escape variants during resolution of primary viraemia. *Nature* 407, 386-390 (2000).

96. D. H. O'Connor, T. M. Allen, T. U. Vogel, P. Jing, I. P. DeSouza, E. Dodds, E. J. Dunphy, C. Melsaether, B. Mothe, H. Yamamoto, H. Horton, N. Wilson, A. L. Hughes, D. I. Watkins, Acute phase cytotoxic T lymphocyte escape is a hallmark of simian immunodeficiency virus infection. *Nat. Med.* 8, 493-499 (2002).

97. M. C. Re, G. Furlini, M. Vignoli, E. Ramazzotti, G. Roderigo, R. De, V, G. Zauli, S. Lolli, S. Capitani, P. M. La, Effect of antibody to HIV-1 Tat protein on viral replication in vitro and progression of HIV-1 disease in vivo. *J. Acquir. Immune. Defic. Syndr. Hum. Retrovirol.* 10, 408-416 (1995).

98. C. A. van Baalen, O. Pontesilli, R. C. Huisman, A. M. Geretti, M. R. Klein, W. F. de, F. Miedema, R. A. Gruters, A. D. Osterhaus, Human immunodeficiency virus type 1 Rev- and Tat-specific cytotoxic T lymphocyte frequencies inversely correlate with rapid progression to AIDS. *J. Gen. Virol.* 78 (Pt 8), 1913-1918 (1997).

99. A. Venet, I. Bourgault, A. M. Aubertin, M. P. Kieny, J. P. Levy, Cytotoxic T lymphocyte response against multiple simian immunodeficiency virusA (SIV) proteins in SIV-infected macaques. *J. Immunol.* 148, 2899-2908 (1992).

100. B. Ensoli, V. Fiorelli, F. Ensoli, A. Cafaro, F. Titti, S. Butto, P. Monini, M. Magnani, A. Caputo, E. Garaci, Candidate HIV-1 Tat vaccine development: from basic science to clinical trials. *AIDS* 20, 2245-2261 (2006).

101. R. Gavioli, E. Gallerani, C. Fortini, M. Fabris, A. Bottoni, A. Canella, A. Bonaccorsi, M. Marastoni, F. Micheletti, A. Cafaro, P. Rimessi, A. Caputo, B. Ensoli, HIV-1 tat protein modulates the generation of cytotoxic T cell epitopes by modifying proteasome composition and enzymatic activity. *J. Immunol.* 173, 3838-3843 (2004).

102. R. Gavioli, S. Cellini, A. Castaldello, R. Voltan, E. Gallerani, F. Gagliardoni, C. Fortini, E. B. Cofano, C. Triulzi, A. Cafaro, I. Srivastava, S. Barnett, A. Caputo, B. Ensoli, The Tat protein broadens T cell responses directed to the HIV-1 antigens Gag and Env: implications for the design of new vaccination strategies against AIDS. *Vaccine* 26, 727-737 (2008).

103. A. L. Remoli, G. Marsili, E. Perrotti, E. Gallerani, R. Ilari, F. Nappi, A. Cafaro, B. Ensoli, R. Gavioli, A. Battistini, Intracellular HIV-1 Tat protein represses constitutive LMP2 transcription increasing proteasome activity by interfering with the binding of IRF-1 to STAT1. *Biochem. J.* 396, 371-380 (2006).

104. B. Lee, M. Sharron, C. Blanpain, B. J. Doranz, J. Vakili, P. Setoh, E. Berg, G. Liu, H. R. Guy, S. R. Durell, M. Parmentier, C. N. Chang, K. Price, M. Tsang, R. W. Doms, Epitope mapping of CCR5 reveals multiple conformational states and distinct but overlapping structures involved in chemokine and coreceptor function. *J. Biol. Chem.* 274, 9617-9626 (1999).

105. A. Borsetti, S. Baroncelli, M. T. Maggiorella, S. Moretti, E. Fanales-Belasio, L. Sernicola, A. Tripiciano, I. Macchia, Z. Michelini, R. Belli, S. Farcomeni, M. R. Pavone-Cossut, D. Negri, A. Caputo, S. Bellino, S. Butto, F. Titti, A. Cafaro, B. Ensoli, Containment of infection in tat vaccinated monkeys after rechallenge with a higher dose of SHIV89.6P(cy243). *Viral Immunol.* 22, 117-124 (2009).

106. A. Cafaro, A. Caputo, C. Fracasso, M. T. Maggiorella, D. Goletti, S. Baroncelli, M. Pace, L. Semicola, M. L. Koanga-Mogtomo, M. Betti, A. Borsetti, R. Belli, L. Akerblom, F. Corrias, S. Butto, J. Heeney, P. Verani, F. Titti, B. Ensoli, Control of SHIV-89.6P-infection of cynomolgus monkeys by HIV-1 Tat protein vaccine. *Nat. Med.* 5, 643-650 (1999).

107. A. Cafaro, A. Caputo, M. T. Maggiorella, S. Baroncelli, C. Fracasso, M. Pace, A. Borsetti, L. Sernicola, D. R.

Negri, H. P. ten, M. Betti, Z. Michelini, I. Macchia, E. Fanales-Belasio, R. Belli, F. Corrias, S. Butto, P. Verani, F. Titti, B. Ensoli, SHIV89.6P pathogenicity in cynomolgus monkeys and control of viral replication and disease onset by human immunodeficiency virus type 1 Tat vaccine. *J. Med. Primatol.* 29, 193-208 (2000).

108. A. Cafaro, F. Titti, C. Fracasso, M. T. Maggiorella, S. Baroncelli, A. Caputo, D. Goletti, A. Borsetti, M. Pace, E. Fanales-Belasio, B. Ridolfi, D. R. Negri, L. Semicola, R. Belli, F. Corrias, I. Macchia, P. Leone, Z. Michelini, H. P. ten, S. Butto, P. Verani, B. Ensoli, Vaccination with DNA containing tat coding sequences and unmethylated CpG motifs protects cynomolgus monkeys upon infection with simian/human immunodeficiency virus (SHIV89.6P). *Vaccine* 19, 2862-2877 (2001).

109. M. T. Maggiorella, S. Baroncelli, Z. Michelini, E. Fanales-Belasio, S. Moretti, L. Semicola, A. Cara, D. R. Negri, S. Butto, V. Fiorelli, A. Tripiciano, A. Scoglio, A. Caputo, A. Borsetti, B. Ridolfi, R. Bona, H. P. ten, I. Macchia, P. Leone, M. R. Pavone-Cossut, F. Nappi, M. Ciccozzi, J. Heeney, F. Titti, A. Cafaro, B. Ensoli, Long-term protection against SHIV89.6P replication in HIV-1 Tat vaccinated cynomolgus monkeys. *Vaccine* 22, 3258-3269 (2004).

110. A. Cafaro, S. Bellino, F. Titti, M. T. Maggiorella, L. Semicola, W. R. Wiseman, D. Venson, A. J. Karl., D. O'Connor, P. Monini, M. Robert-Guroff, B. Ensoli. Impact of Viral Dose and Major Histocompatibility Complex Class IB Haplotype on Viral Outcome in Tat-vaccinated MauritianCynomolgus Monkeys upon Challenge with SHIV89.6P *J. Virol.* 84: 8953-8 (2010).

111. Bellino, S., Francavilla, V., Tripiciano, A., Paniccia, G., Arancio, A., Fiorelli, V., Scoglio, A., Collacchi, B., Campagna, M., Lazzarin, A., Tambussi, G., Tassan, Din C., Visintini, R., Narciso, P., Antinori, A., D'Offizi, G., Giulianelli, M., Carta, M., Di, Carlo A., Palamara, G., Giuliani, M., Laguardia, M. E., Monini, P., Magnani, M., Ensoli, F., and Ensoli, B. Parallel conduction of the phase I preventive and therapeutic trials based on the Tat vaccine candidate. Reviews on Recent Clinical Trials 4, 195-204. 2009.

112. A. Caputo, R. Gavioli, S. Bellino, O. Longo, A. Tripiciano, V. Francavilla, C. Sgadari, G. Paniccia, F. Titti, A. Cafaro, F. Ferrantelli, P. Monini, F. Ensoli, B. Ensoli, HIV-1 Tat-based vaccines: an overview and perspectives in the field of HIV/AIDS vaccine development. *Int. Rev. Immunol.* 28, 285-334 (2009).

113. B. Ensoli, V. Fiorelli, F. Ensoli, A. Lazzarin, R. Visintini, P. Narciso, C. A. Di, P. Monini, M. Magnani, E. Garaci, The therapeutic phase I trial of the recombinant native HIV-1 Tat protein. *AIDS* 22, 2207-2209 (2008).

114. B. Ensoli, V. Fiorelli, F. Ensoli, A. Lazzarin, R. Visintini, P. Narciso, C. A. Di, A. Tripiciano, O. Longo, S. Bellino, V. Francavilla, G. Paniccia, A. Arancio, A. Scoglio, B. Collacchi, M. J. Ruiz Alvarez, G. Tambussi, D. C. Tassan, G. Palamara, A. Latini, A. Antinori, G. D'Offizi, M. Giuliani, M. Giulianelli, M. Carta, P. Monini, M. Magnani, E. Garaci, The preventive phase I trial with the HIV-1 Tat-based vaccine. *Vaccine* 28, 371-378 (2009).

115. O. Longo, A. Tripiciano, V. Fiorelli, S. Bellino, A. Scoglio, B. Collacchi, M. J. Alvarez, V. Francavilla, A. Arancio, G. Paniccia, A. Lazzarin, G. Tambussi, C. T. Din, R. Visintini, P. Narciso, A. Antinori, G. D'Offizi, M. Giulianelli, M. Carta, C. A. Di, G. Palamara, M. Giuliani, M. E. Laguardia, P. Monini, M. Magnani, F. Ensoli, B. Ensoli, Phase I therapeutic trial of the HIV-1 Tat protein and long term follow-up. *Vaccine* 27, 3306-3312 (2009).

116. T. H. Finkel, G. Tudor-Williams, N. K. Banda, M. F. Cotton, T. Curiel, C. Monks, T. W. Baba, R. M. Ruprecht, A. Kupfer, Apoptosis occurs predominantly in bystander cells and not in productively infected cells of HIV- and SIV-infected lymph nodes. *Nat. Med.* 1, 129-134 (1995).

117. M. L. Gougeon, Apoptosis as an HIV strategy to escape immune attack. *Nat. Rev. Immunol.* 3, 392-404 (2003).

118. N. Oyaizu, T. W. McCloskey, M. Coronesi, N. Chirmule, V. S. Kalyanaraman, S. Pahwa, Accelerated apoptosis in peripheral blood mononuclear cells (PBMCs) from human immunodeficiency virus type-1 infected patients and in CD4 cross-linked PBMCs from normal individuals. *Blood* 82, 3392-3400 (1993).

119. H. N. Ho, L. E. Hultin, R. T. Mitsuyasu, J. L. Matud, M. A. Hausner, D. Bockstoce, C. C. Chou, S. O'Rourke, J. M. Taylor, J. V. Giorgi, Circulating HIV-specific CD8+ cytotoxic T cells express CD38 and HLA-DR antigens. *J. Immunol.* 150, 3070-3079 (1993).

120. A. Saez-Cirion, C. Lacabaratz, O. Lambotte, P. Versmisse, A. Urrutia, F. Boufassa, F. Barre-Sinoussi, J. F. Delfraissy, M. Sinet, G. Pancino, A. Venet, HIV controllers exhibit potent CD8 T cell capacity to suppress HIV infection ex vivo and peculiar cytotoxic T lymphocyte activation phenotype. *Proc. Natl. Acad. Sci. U.S.A* 104, 6776-6781 (2007).

121. A. Savarino, F. Bottarel, L. Calosso, M. J. Feito, T. Bensi, M. Bragardo, J. M. Rojo, A. Pugliese, I. Abbate, M. R. Capobianchi, F. Dianzani, F. Malavasi, U. Dianzani, Effects of the human CD38 glycoprotein on the early stages of the HIV-1 replication cycle. *FASEB J.* 13, 2265-2276 (1999).

122. A. Biancotto, S. J. Iglehart, C. Vanpouille, C. E. Condack, A. Lisco, E. Ruecker, I. Hirsch, L. B. Margolis, J. C. Grivel, HIV-1 induced activation of CD4+ T cells creates new targets for HIV-1 infection in human lymphoid tissue ex vivo. *Blood* 111, 699-704 (2008).

123. J. Andersson, A. Boasso, J. Nilsson, R. Zhang, N. J. Shire, S. Lindback, G. M. Shearer, C. A. Chougnet, The prevalence of regulatory T cells in lymphoid tissue is correlated with viral load in HIV-infected patients. *J. Immunol.* 174, 3143-3147 (2005).

124. P. A. Apoil, B. Puissant, F. Roubinet, M. Abbal, P. Massip, A. Blancher, FOXP3 mRNA levels are decreased in peripheral blood CD4+ lymphocytes from HIV-positive patients. *J. Acquir. Immune. Defic. Syndr.* 39, 381-385 (2005).

125. M. P. Eggena, B. Barugahare, N. Jones, M. Okello, S. Mutalya, C. Kityo, P. Mugyenyi, H. Cao, Depletion of regulatory T cells in HIV infection is associated with immune activation. *J. Immunol.* 174, 4407-4414 (2005).

126. Y. Jiao, J. Fu, S. Xing, B. Fu, Z. Zhang, M. Shi, X. Wang, J. Zhang, L. Jin, F. Kang, H. Wu, F. S. Wang, The decrease of regulatory T cells correlates with excessive activation and apoptosis of CD8+ T cells in HIV-1-infected typical progressors, but not in long-term non-progressors. *Immunology* 128, e366-e375 (2009).

127. A. Mozos, M. Gamido, J. Carreras, M. Plana, A. Diaz, L. Alos, E. Campo, F. Garcia, A. Martinez, Redistribution of FOXP3-positive regulatory T cells from lymphoid tissues to peripheral blood in HIV-infected patients. *J. Acquir. Immune. Defic. Syndr.* 46, 529-537 (2007).

128. K. Oswald-Richter, S. M. Grill, N. Shariat, M. Leelawong, M. S. Sundrud, D. W. Haas, D. Unutmaz, HIV infection of naturally occurring and genetically reprogrammed human regulatory T-cells. *PLoS. Biol.* 2, E198 (2004).

129. J. D. Ahlers, I. M. Belyakov, Memories that last forever: strategies for optimizing vaccine T-cell memory. *Blood* 115, 1678-1689 (2010).

130. J. D. Miller, R. G. van der Most, R. S. Akondy, J. T. Glidewell, S. Albott, D. Masopust, K. Murali-Krishna, P. L. Mahar, S. Edupuganti, S. Lalor, S. Germon, R. C. Del, M. J. Mulligan, S. I. Staprans, J. D. Altman, M. B. Feinberg, R. Ahmed, Human effector and memory CD8+ T cell responses to smallpox and yellow fever vaccines. *Immunity.* 28, 710-722 (2008).

131. B. J. Luft, J. S. Remington. Toxoplasmic encephalitis in AIDS. *Clin Infect Dis.* 15: 211-22 (1992).

132. K. Schroecksnadel, M. Sarcletti, C. Winkler, B. Mumelter, G. Weiss, D. Fuchs, G. Kemmler, R. Zangerle, Quality of life and immune activation in patients with HIV-infection. *Brain Behav. Immun.* 22, 881-889 (2008).

133. Burtis, C. A. and Aswhood, E. R. Tietz Textbook of Clinical Chemistry, 2nd Edition W.B. Saunders Ed. (1994).

134. K. B. Mullis, F. A. Faloona, Specific synthesis of DNA in vitro via a polymerase-catalyzed chain reaction. *Methods Enzymol.* 155, 335-350 (1987).

135. J. W. Pollard, The in vivo isotopic labeling of proteins for polyacrylamide gel electrophoresis. *Methods Mol. Biol.* 32, 67-72 (1994).

136. S. E. Szabo, S. L. Monroe, S. Fiorino, J. Bitzan, K. Loper, Evaluation of an automated instrument for viability and concentration measurements of cryopreserved hematopoietic cells. *Lab Hematol.* 10, 109-111 (2004).

137. S. L. Welles, J. B. Jackson, B. Yen-Lieberman, L. Demeter, A. J. Japour, L. M. Smeaton, V. A. Johnson, D. R. Kuritzkes, R. T. D'Aquila, P. A. Reichelderfer, D. D. Richman, R. Reichman, M. Fischl, R. Dolin, R. W. Coombs, J. O. Kahn, C. McLaren, J. Todd, S. Kwok, C. S. Crumpacker, Prognostic value of plasma human immunodeficiency virus type 1 (HIV-1) RNA levels in patients with advanced HIV-1 disease and with little or no prior zidovudine therapy. AIDS Clinical Trials Group Protocol 116A/116B/117 Team. *J. Infect. Dis.* 174, 696-703 (1996).

138. S. Reigadas, M.-L. Andréola, L. Wittkop, O. Cosnefroy, G. Anies, P. Recordon-Pinson, R. Thiébaut, B. Masquelier, H. Fleury. Evolution of 2-long terminal repeat (2-LTR) episomal HIV-1 DNA in raltegravir-treated patients and in in vitro infected cells. *J Antimicrob Chemother.* 65:434-7 (2010).

139. R. T. Gandhi, L. Zheng, R. J. Bosch, E. S. Chan, D. M. Margolis, S. Read, B. Kallungal, S. Palmer, K. Medvik, M. M. Lederman, N. Alatrakchi, J. M. Jacobson, A. Wiegand, M. Kearney, J. M. Coffin, J. W. Mellors, Joseph J Eron, AIDS Clinical Trials Group A5244 team. The effect of raltegravir intensification on low-level residual viremia in HIV-infected patients on antiretroviral therapy: a randomized controlled trial. *Plos Med.* 7: e1000321 (2010).

140. C. Delaugerre, I. Charreau, J. Braun, M.-L. Néré, N. de Castro, P. Yeni, J. Ghosn, J. P. Aboulker, J. M. Molina, F. Simon, ANRS 138 study group. Time course of total HIV-1 DNA and 2-long-terminal repeat circles in patients with controlled plasma viremia switching to a raltegravir-containing regimen. *AIDS* 24:2391-5 (2010).

141. M. Eigen, R. Winkler-Oswatitsch, A. Dress. Statistical geometry in sequence space: a method of quantitative comparative sequence analysis. *Proc. Natl. Acad. Sci.* 1988 85:5913-7.

142. S. W. Barnett, S. Lu, I. Srivastava, S. Cherpelis, A. Gettie, J. Blanchard, S. Wang, I. Mboudjeka, L. Leung, Y. Lian, A. Fong, C. Buckner, A. Ly, S. Hilt, J. Ulmer, C. T. Wild, J. R. Mascola, L. Stamatatos. The ability of an oligomeric human immunodeficiency virus type 1 (HIV-1) envelope antigen to elicit neutralizing antibodies against primary HIV-1 isolates is improved following partial deletion of the second hypervariable region. *J Virol* 2001, 75:5526-5540.

143. I. K. Srivastava, L. Stamatatos, E. Kan, M. Vajdy, Y. Lian, S. Hilt, L. Martin, C. Vita, P. Zhu, K. H. Roux, L. C. Vojtech, D. Montefiori, J. Donnelly, J. B. Ulmer, S. W. Barnett. Purification, characterization, and immunogenicity of a soluble trimeric envelope protein containing a partial deletion of the V2 loop derived from SF162, an R5-tropic human immunodeficiency virus type 1 isolate. *J Virol* 2003a, 77:11244-11259.

Patent List

B. Ensoli, Novel Tat complexes, and vaccines comprising them. Priority date Mar. 11, 2004; PCT Mar. 11, 2005, No. PCT/EP2005/003043, Publication No. WO2005/090391.

The invention claimed is:

1. A method comprising:
administering native, biologically active Tat, or a molecule having the immunological properties of native, biologically active Tat, at least three times to an individual having a persistent HIV infection, which individual is on treatment with an antiretroviral therapy, thereby increasing percentage or counts of $CD4^+$ T cells, B cells, and/or $CD4^+CD25^+FOXP3^+$ regulatory T cells (T-regs), HLA-DR expression on $CD8^+CD38^+$ and/or $CD8^+CD38^-$ cells, and/or percentage of central memory $CD4^+$ and/or $CD8^+$ T cells in the individual; and/or decreasing percentage of terminally differentiated effector memory $CD4^+$ and/or $CD8^+$ T cells in the individual, and thereby providing durable control of HIV proviral load in the individual for at least one year.

2. The method of claim 1, wherein said administration reduces levels of inflammation and reactivation associated with chronic infection.

3. The method of claim 1, wherein said administration induces an anti-pathogen response, wherein said individual has a chronic infection of the pathogen.

4. The method of claim 3, wherein said pathogen is HIV or *Toxoplasma gondii*.

5. The method of claim 1, wherein said administration induces antibodies and/or cellular responses capable of reducing HIV in the individual.

6. The method of claim 1, wherein said administration partially or completely restores B cell and/or T cell responses against persistent infections, and/or the ability to respond to new infections, and/or reduces systemic immune activation.

7. The method of claim 1, wherein said administration causes a reduction in HIV DNA, an inhibition of the infection of new target cells, and/or a reduction in the number of infected cells replicating HIV.

8. A method comprising:
administering native, biologically active Tat, or a molecule having the immunological properties of native, biologically active Tat, at least three times to an individual having a persistent HIV infection, wherein the individual is on treatment with an antiretroviral therapy,
thereby increasing peripheral blood mononuclear cell viability in the individual, and thereby providing durable control of HIV proviral load in the individual for at least one year.

9. The method of claim 8, wherein said administration reduces levels of inflammation and reactivation associated with chronic infection in the individual.

10. The method of claim 8, wherein said administration induces a response to a pathogen, wherein said individual has a chronic infection of the pathogen.

11. The method of claim 10, wherein said pathogen is HIV or *Toxoplasma gondii*.

12. The method of claim 8, wherein said administration induces antibodies and/or cellular responses capable of reducing HIV in the individual.

13. The method of claim 8, wherein said administration partially or completely restores B cell and/or T cell responses against persistent infections in the individual and/or the ability of the individual to respond to new infections and/or reduces systemic immune activation in the individual.

14. The method of claim 8, wherein said administration reduces HIV DNA, infection of new target cells, and/or the number of infected cells replicating HIV in the individual.

15. A method comprising:
administering native, biologically active Tat, or a molecule having the immunological properties of native, biologically active Tat, at least three times to an individual having a persistent HIV infection, wherein the individual is on treatment with an antiretroviral therapy,
thereby preventing or reducing emergence of HIV quasispecies in the individual, and thereby providing durable control of HIV proviral load in the individual for at least one year.

16. The method of claim 15, wherein said administration reduces levels of inflammation and reactivation associated with chronic infection in the individual.

17. The method of claim 15, wherein said individual has a chronic infection of a pathogen and said administration induces a response to the pathogen.

18. The method of claim 17, wherein said pathogen is HIV or *Toxoplasma gondii*.

19. The method of claim 15, wherein said administration induces antibodies and/or cellular responses, thereby reducing HIV in the individual.

20. The method of claim 15, wherein said administration partially or completely restores B cell and/or T cell responses against persistent infections in the individual and/or the ability of the individual to respond to new infections and/or reduces systemic immune activation.

21. The method of claim 15, wherein said administration reduces viral DNA, infection of new target cells, and/or the number of infected cells replicating HIV in the individual.

22. A method comprising:
administering native, biologically active Tat, or a molecule having the immunological properties of native, biologically active Tat, at least three times to an individual having a persistent HIV infection, wherein the individual is on treatment with an antiretroviral therapy,
thereby decreasing HIV DNA, increasing HIV RNA, and/or blocking the emergence of HIV quasispecies, thereby purging the HIV virus reservoir in the individual, and thereby providing durable control of HIV proviral load in the individual for at least one year.

23. The method of claim 22, wherein said administration reduces levels of inflammation and reactivation associated with chronic infection in the individual.

24. The method of claim 22, wherein individual has a chronic infection of a pathogen and said administration induces a response to the pathogen in the individual.

25. The method of claim 24, wherein said pathogen is HIV or *Toxoplasma gondii*.

26. The method of claim 22, wherein said administration induces antibodies and/or cellular responses, thereby reducing HIV DNA, increasing HIV RNA, blocking the emergence of HIV quasispecies, and purging the HIV virus reservoir in the individual.

27. The method of claim 22, wherein said administration partially or completely restores B cell and/or T cell responses against persistent infections in the individual and/or the ability of the individual to respond to new infections and/or reduces systemic immune activation in the individual.

28. The method of claim 22, wherein said administration reduces HIV infection of new target cells, and/or the number of infected cells replicating HIV in the individual.

* * * * *